US007700586B2

(12) United States Patent
Li et al.

(10) Patent No.: US 7,700,586 B2
(45) Date of Patent: Apr. 20, 2010

(54) ARYLSULFONAMIDE DERIVATIVES FOR USE AS CCR3 ANTAGONISTS IN THE TREATMENT OF INFLAMMATORY AND IMMUNOLOGICAL DISORDERS

(75) Inventors: Yingfu Li, Nara-ken (JP); Akihiko Watanabe, Shizuoka-ken (JP); Timothy B. Lowinger, Guilford, CT (US); Kevin Bacon, Hyogo-ken (JP); Norihiro Kawamura, Nara-ken (JP); Takuya Shintani, Kyoto-fu (JP); Tetsuo Kikuchi, Nara-ken (JP); Toshiya Moriwaki, Nara-ken (JP); Klaus Urbahns, Hyogo-ken (JP); Keiko Fukushima, Saitama-ken (JP); Noriko Nunami, Nara-ken (JP); Takashi Yoshino, Shiga-ken (JP); Toshiki Murata, Nara-ken (JP); Megumi Yamauchi, Shiga-ken (JP); Hiroko Yoshino, Shiga-ken (JP)

(73) Assignee: Axikin Pharmaceuticals, Inc., San Diego, CA (US)

( * ) Notice: Subject to any disclaimer, the term of this patent is extended or adjusted under 35 U.S.C. 154(b) by 982 days.

(21) Appl. No.: 10/489,029
(22) PCT Filed: Sep. 4, 2002
(86) PCT No.: PCT/EP02/09873

§ 371 (c)(1),
(2), (4) Date: Oct. 21, 2004

(87) PCT Pub. No.: WO03/022277

PCT Pub. Date: Mar. 20, 2003

(65) Prior Publication Data
US 2005/0070582 A1 Mar. 31, 2005

(30) Foreign Application Priority Data
Sep. 7, 2001 (JP) ............................. 2001-272327

(51) Int. Cl.
A61K 31/55 (2006.01)
A01N 43/62 (2006.01)
A61K 31/497 (2006.01)
C07D 243/08 (2006.01)
C07D 241/04 (2006.01)
C07D 295/00 (2006.01)

(52) U.S. Cl. ............. 514/218; 514/252.12; 514/252.13; 514/253.12; 514/254.01; 514/254.05; 514/254.09; 514/254.1; 540/575; 544/359; 544/360; 544/366; 544/372; 544/373; 544/374; 544/379; 544/383

(58) Field of Classification Search ............. 514/218, 514/252.12, 253.12, 254.05, 254.09, 252.13, 514/254.01, 254.1; 540/575; 544/383, 360, 544/366, 373, 379, 372, 374, 359
See application file for complete search history.

(56) References Cited

U.S. PATENT DOCUMENTS 2,275,354 A   3/1942 Ewins et al. ................. 260/295
3,819,639 A   6/1974 Delarge et al. ........ 260/294.8 F
6,153,757 A * 11/2000 Zook et al. .................. 546/301
7,173,025 B1 * 2/2007 Stocker et al. .............. 514/218
2005/0070582 A1   3/2005 Li et al.

FOREIGN PATENT DOCUMENTS

| WO | WO 99/55324 A1 | 11/1999 |
| WO | WO 00/42003 A1 | 7/2000 |
| WO | WO 00/76513 | 12/2000 |
| WO | WO 00/76514 | 12/2000 |
| WO | WO 01/32604 A1 | 5/2001 |
| WO | WO 03/022277 A1 | 3/2003 |

OTHER PUBLICATIONS

Brauniger et al., Reactions with 2,4-dinitrofluorobenzene, especially with aromatic amines. I. Reaction conditions and synthetic compounds, Pharmazie, 12, 335-48 (1957).*
White J R, et al., Identification of potent, selective non-peptide CC chemokine receptor-3 antagonist that inhibits eotaxin-, eotaxin-2-, and monocyte chemotactic protein-4-induced eosinophil migration, The Journal of biological chemistry, (Nov. 24, 2000) vol. 275, No. 47, pp. 36626-36631.*
White J R, et al., Identification of potent, selective non-peptide CC chemokine receptor-3 antagonist that inhibits eotaxin-, eotaxin-2-, and monocyte chemotactic protein-4-induced eosinophil migration, The Journal of biological chemistry, (Nov. 24, 2000) vol. 275, No. 47, pp. 36626-36631.*
International Search Report of International Application No. PCT/EP02/09873 having a Publication No. WO 03/022277.
Saari et al., "Synthesis and Evaluation of Some Nitrobenzenesulfonamides Containing Nitroisopropyl and (Ureidooxy)methyl Groups as Novel Hypoxic Cell Selective Cytotoxic Agents," *J. Med. Chem.* 1991, 34, 3132-3138.
Chemcats Database, Ambinter Stock Screening Collection, Order Nos. 7J-012, 7J-005 and 7J-004.
Mastrukova et al., "The Application of the Hammett Equation to the Theory of Tautomeric Equilibrium-II," *Tetrahedron*, 1963, vol. 19, pp. 357-372.
J. Delarge, "Nouveaux Anti-inflammatoires Derives de la Pyridine," *Ann. Pharm. Fr.*, 1973, vol. 31, No. 6, pp. 467-474. (English summary at p. 474).
"Chemokine CCR3 Antagonists," *Exp. Opin. Ther. Patents*, 2000, vol. 10(9), pp. 1455-1459.
Alaaeddine et al., "Production of the Chemokine RANTES by Articular Chrondrocytes and Role in Cartilage Degradation," *Arthritis & Rheumatism*, vol. 44, No. 7, pp. 1633-1643 (2001).
Ancuta et al., CD16+ monocyte-derived macrophages activate resting T cells for HIV infection by producing CCR3 and CCR4 ligands, *J. Immunol.*, vol. 176, pp. 5760-5771 (2006).

(Continued)

*Primary Examiner*—James O Wilson
*Assistant Examiner*—Erich A Leeser
(74) *Attorney, Agent, or Firm*—Jones Day

(57) ABSTRACT

The present invention relates to a sulfonamide derivative which is useful as an active ingredient of pharmaceutical preparations. The sulfonamide derivatives of the present invention have CCR3 (CC type chemokine receptor) antagonistic activity, and can be used for the prophylaxis and treatment of diseases associated with CCR3 activity, in particular for the treatment of asthma, atopic dermatitis, allergic rhinitis and other inflammatory/immunological disorders.

19 Claims, No Drawings

OTHER PUBLICATIONS

Aust et al., "Grave's disease is associated with an altered CXCR3 and CCR5 expression in thyroid-derived compared to peripheral blood lymphocytes," *Clin. Exp. Immunol.*, vol. 127, pp. 479-485 (2001).

Bhattacharya, et al., "Increased expression of eotaxin-3 distinguishes between eosinophilic esophagitis and gastroesophageal reflux disease," *Human Pathology*, vol. 38, pp. 1744-1753 (2007).

Blanchard et al., "Eotaxin-3 and a uniquely conserved gene-expression profile in eosinophilic esophagitis," *J. Clin. Invest.*, vol. 116, No. 2, pp. 536-547 (2006).

Bullock et al., "Interplay of adaptive Th2 immunity with eotaxin-3/C-C chemokine receptor 3 in eosinophilic esophagitis," *J. Pediatric Gastroenterology and Nutrition*, vol. 45, pp. 22-31 (2007).

Cheadle et al., "Eotaxin-2 and colorectal cancer: a potential target for immune therapy," *Human Cancer Biol.*, vol. 13, No. 19, pp. 5719-5728 (2007).

Chi et al., "C-Reactive protein enhances expression of chemokine receptors on mast cells," *The FASEB Journal*, vol. 16, No. 4, p. A690, abstract 514.2 (2002).

Dol et al., "Angiotensin AT1 receptor antagonist irbesartan decreases lesion size, chemokine expression, and macrophage accumulation in apolipoprotein E-deficient mice," *J. Cardiovascular Pharmacology*, vol. 38, pp. 395-405 (2001).

Elsner et al., "Human Eotaxin Represents a Potential Activator of the Respiratory Burst of Human Eosinophils," Eur. J. Immunol., vol. 26, pp. 1919-1925 (1996).

Foster et al., "Elemental signals regulating eosinophil accumulation in the lung," *Immunol. Rev.*, vol. 179, pp. 173-181 (2001).

Gerber et al., "Functional expression of the eotaxin receptor CCR3 in T lymphocytes co-localizing with eosinophils," *Current Biology*, vol. 7, pp. 836-843 (1997).

Haley et al., "Overexpression of Eotaxin and the CCR3 Receptor in Human Atherosclerosis: Using Genomic Technology to Identify a Potential Novel Pathway of Vascular Inflammation," *Circulation*, vol. 102, pp. 2185-2189 (2000).

Hogoboam et al., "Collagen Deposition in Non-Fibrotic Lung Granuloma Model after Nitric Oxide Inhibition," *Am. J. Pathology*, vol. 153, No. 6, pp. 1861-1872 (1998).

Hsu et al., "Production of the chemokine eotaxin-1 in osteoarthritis and its role in cartilage degradation," *J. Cellular Biochem.*, vol. 93, pp. 929-939 (2004).

Huaux et al., "Role of eotaxin-1 (CCL11) and CC chemokine receptor 3 (CCR3) in bleomycin-induced lung injury and fibrosis," vol. 167, No. 6, pp. 1485-1496 (2005).

Hunt et al., "Newly identified genetic risk variants for celiac disease related to the immune response," *Nature Genetics*, vol. 40, No. 4, pp. 395-402 (2008).

Jahnz-Royk et al., "Eotaxin in serum of patients with asthma or chronic obstructive pulmonary disease: relationship with eosophil cationic protein and lung function," *Mediators of Inflam.*, vol. 9, pp. 175-179 (2000).

Johrer et al., "Up-regulation of functional chemokine receptor CCR3 in human renal cell carcinoma," *Human Cancer Biol.*, vol. 11, No. 7, pp. 2459-2465 (2005).

Joubert et al., "CCR3 expression and function in asthmatic airway smooth muscle cells," *J. Immunol.*, vol. 175, pp. 2702-2708 (2005).

Katschke et al., "Differential Expression of Chemokine Receptors on Peripheral Blood, Synovial Fluid, and Synovial Tissue Monocytes/Macrophages in Rheumatoid Arthritis," *Arthritis & Rheumatism*, vol. 44, No. 5, pp. 1022-1032 (2001).

Kouno et al. "Up-regulation of CC chemokine, CCL3L1, and receptors, CCR3, CCR5 in human glioblastoma that promotes cell growth," *J. Neuro-Oncology*, vol. 70, pp. 301-307 (2004).

Lamkhioued et al., "Increased expression of eotaxin in bronchoaveolar lavage and airways of asthmatics contributes to the chemotaxis of eosinophils to the site of inflammation," *J. Immunol.*, vol. 159, pp. 4593-4601 (1997).

Li et al., "Mast Cells/Basophils in the Peripheral Blood of Allergic Individuals Who Are HIV-1 Susceptible Due to Their Surface Expression of CD4 and the Chemokine Receptors CCR3, CCR5 and CXCR4," *Blood*, vol. 97, No. 11, pp. 3484-3487 (2001).

Marone et al., "Human Mast Cells and Basophils in HIV-1 Infection," *Trends Immunol.*, vol. 22, No. 5., 229-232 (2001).

Marone et al., "Are Mast Cells MASTers in HIV-1 Infection?, " *Int. Arch. Allergy Immunol.*, vol. 125, pp. 89-95 (2001).

Matsukura et al., "Expression of RANTES by normal airway epithelial cells after influenza virus A infection," *Am. J. Respir. Cell and Mol. Biol.*, vol. 18, pp. 255-264 (1998).

Nissinen et al., "CCR3, CCR5 interleukin 4, and interferon-gamma expression on synovial and peripheral T cells and monocytes in rheumatoid arthritis," *J. Rheumatol.*, vol. 30, No. 9, pp. 1928-1934 (2003).

Ohagen et al., "Genetic and functional analysis of full-length human immunodeficiency virus type 1 *env* genes derived from brain and blood or patients with AIDS," *J. Virology*, vol. 77, No. 22, pp. 12336-12345. (2003).

Oliviera et al., "Stem cell factor and IgE-stimulated murine mast cells produce chemokines (CCL2, CCL17, CCL22) and express chemokine receptors," *Inflamm. Res.*, vol. 50, pp. 168-174 (2001).

Park et al., "CD4 Receptor-Dependent Entry of Human Immunodeficiency Virus Type-I *env*-Pseudotypes into CCR5-, CCR3- and CXCR4-Expressing Human Alveolar Macrophages Is Preferrentially Mediated by the CCR5 Coreceptor," *Am. J. Respir. Cell Mol. Biol.*, vol. 20, pp. 864-871 (1999).

Rothenberg et al., "Targeted Disruption of the Chemokine Eotaxin Partially Reduces Antigen-induced Tissue Eosophilia," *J. Exp. Med.*, vol. 185, pp. 785-790 (1997).

Ruth et al., "Expression and Participation of Eotaxin During Mycobacterial (Type 1) and Schistosomal (Type 2) Antigen-Elicited Granuloma Formation," *J. Immunology*, vol. 161, No. 8, pp. 4276-4282 (1998).

Sabroe et al., *J. Immunol.*, "Cloning and Characterization of the Guinea Pig Eosinophil Eotaxin Receptor, C-C Chemokine Receptor-3: Blockade Using a Monoclonal Antibody In Vivo," vol. 161, pp. 6139-6147 (1998).

Saito et al., "Selective regulation of chemokine production in human epithelial cells," *J. Infect. Dis.*, vol. 175, pp. 479-504 (1997).

Sallusto et al., "Selective Expression of the Eotaxin Receptor CCR3 by Human T Helper 2 Cells," *Science*, vol. 277, pp. 2005-2007 (1997).

Silva et al., "Differential expression of chemokines and chemokine receptors in inflammatory periapical diseases," *Oral Microbiol. Immunol.*, vol. 20, pp. 310-316 (2005).

Simchen et al. "Expression and Regulation of Regulated on Activation, Normal T Cells Expressed and Secreted in Thyroid Tissue of Patients with Graves' Disease and Thyroid Autonomy and in Thyroid-Derived Cell Populations," *J. Clinical Endocrinology & Metabolism*, vol. 85, No. 2, 4758-64 (2000).

Stellato et al., "Cutting Edge: Expression of the C-C Chemokine Receptor CCR3 in Human Airway Epithelial Cells," *J. Immunology*, 1457-60 (2001).

Sugasawa et al., "Prognostic significance of expression of CCL5/RANTES receptors in patients with gastric cancer," *J. Sergical Oncology*. vol. 97, pp. 447-450 (2008).

Teixeira et al., "Increased serum levels of CCL11/eotaxin in schizophrenia," *Progress in Neuro-pharmacology & Biol. Psych.*, vol. 32, pp. 710-714. (2008).

Uguccioni et al., "High Expression of the Chemokine Receptor CCR3 in Human Blood Basophils," *J. Clin. Invest.*, vol. 100, pp. 1137-1143 (1997).

Weeraratna et al., "Alterations in immunological and neurological gene expression patterns in Alzheimer's disease tissues," *Exp. Cell. Res.*, vol. 313, pp. 450-461 (2007).

White et al., "Identification of potent, selective, non-peptide CC chemokine receptor-3 antagonist that inhibits eotaxin-, eotaxin-2-, and monocyte chemotactic protein-4-induced eosinophil migration," *J. Bio. Chem.*, vol. 275, No. 47, pp. 36626-36631 (2000).

Xia et al., "Chemokines/Chemokine Receptors in the Central Nervous System and Alzheimer's Disease," *J. Neurovirology*, vol. 5, pp. 32-41 (1999).

Xia et al., "Expression of the chemokine receptor CXCR3 on neurons and the elevated expression of its ligand IP-10 in reactive astrocytes: in vitro ERK1/2 activation and role in Alzheimer's disease," *J. Immunol.*, 108, 227-35 (2000).

Xia et al., "Immunihistochemical Study of the β Chemokine Receptors of CCR3 and CCR5 and Their Ligands in Normal and Alzheimer's Diseases Brains," *Am. J. Pathology*, vol. 153, No. 1, pp. 31-36 1998.

Ying et al., "Enhanced expression of eotaxin and CCR3 mRNA and protein in atopic asthma. Association with airway hyperresponsiveness and predominant colocalization of eotaxin mRNA to bronchial epithelial and endothelial cells," *Eur. J. Immunol*, vol. 27, 3507-3516 (1997).

Bertrand et al. "CCR3 Blockade as a new therapy for asthma," *Expert Opinion on Investigational Drugs* 9(1):4352 (2000).

International Search Report of International Application No. PCT/EP2004/002496 having a Publication No. WO 2004/084898.

"NAEP's asthma bulletin board," http://www.asthma.co.za/news01.htm, accessed Aug. 5, 2008.

Ponath, P. "Chemokine receptor antagonists: novel therapeutics for inflammation and AIDS," *Expert Opinion on Investigational Drugs* 7(1): 1-18 (1998).

Office Action dated Aug. 19, 2008 in U.S. Appl. No. 10/550,482.

International Search Report of International Application No. PCT/EP02/09873 having a Publication No. WO 03/022277 (published Mar. 20, 2003).

Chemcats Database, Ambinter Stock Screening Collection, Order Nos. 7J-012, 7J-005 and 7J-004 (published Jan. 1, 2004).

* cited by examiner

ARYLSULFONAMIDE DERIVATIVES FOR USE AS CCR3 ANTAGONISTS IN THE TREATMENT OF INFLAMMATORY AND IMMUNOLOGICAL DISORDERS

TECHNICAL FIELD

The present invention relates to a sulfonamide derivative which is useful as an active ingredient of pharmaceutical preparations. The sulfonamide derivatives of the present invention have CCR3 (CC type chemokine receptor 3) antagonistic activity, and can be used for the prophylaxis and treatment of diseases associated with CCR3 activity, in particular for the treatment of asthma, atopic dermatitis, allergic rhinitis and other inflammatory/immunological disorders.

BACKGROUND ART

Chemokines are chemotactic cytokines of which major functions are migration of inflammatory cells that express relevant chemokine receptors on their surfaces to sites of inflammation, and activation of inflammatory cells. There are two classes of chemokines, C-X-C (.alpha.) and C-C (i), depending on whether the first two cysteines are separated by a single amino acid (C-X-C) or are adjacent (C-C).

One of the C-C family of chemokines, eotaxin, is an 8.4 kDa (74 amino acid) polypeptide and binds with high affinity solely to the receptor CCR3. In vitro and in vivo eotaxin causes chemotaxis of inflammatory cells expressing CCR3 [Elsner J., Hochstetter R., Kimming D. and Kapp A.: Human eotaxin represents a potent activator of the respiratory burst of human eosinophils. Eur. J. Immunol., 26: 1919-1925, 1996.].

The chemokine receptor CCR3 is a G protein-coupled, seven transmembrane domain receptor (GPCR) which binds to known ligands, in addition to eotaxin, including eotaxin-2 (CCL24), RANTES (CCL5), MCP-3 (CCL7) and MCP-4 (CCL13). CCR3 is expressed on inflammatory cells relevant to the chronic asthma pathology. Such inflammatory cells include Eosinophils [Sabroe I., Conroy D. M., Gerard N. P., Li Y., Collins P. D., Post T. W., Jose P. J., Williams T. J., Gerard C. J., Ponath P. D. J. Immunol. 161: 6139-6147, 1998], basophils [Uguccioni M., Mackay C. R., Ochensberger B., Loetscher P., Rhis S., LaRosa G. J., Rao P., Ponath P. D., Baggiolini M., Dahinden C. A. J. Clin. Invest. 100: 1137-1143, 1997], Th2 cells [Sallusto F., Mackay C. R., Lanzavecchia A. Science. 277: 2005-2007, 1997), alveolar macrophages [Park I. W., Koziel H., Hatch W., Li X., Du B., Groopman J. E. Am. J. Respir. Cell Mol. Biol. 20:864-71, 1999] and mast cells [Oliveira S. H. and Lukacs N. W. Inflamm. Res. 50: 168-174, 2001]. Very recently, it was reported that BEAS-2B, an epithelial cell line, stimulated with TNF-α and IFN-γ, expressed CCR3 [Stellato C., Brummet M. E., Plitt J. R., Shahabuddin S., Baroody F. M., Liu M., Ponath P. D., and Beck L. A. J. Immunol., 166: 1457-1461, 2001.].

In animal models, eotaxin-knockout mice showed decreased eosinophilia after antigen challenge [Rothenberg M. E., MacLean J. A., Pearlman E., Luster A. D. and Leder P. J. Exp. Med., 185: 785-790, 1997] and in IL5-/eotaxin-double knock-out mice there is no eosinophilia or AHR in response to antigen challenge [Foster P. S., Mould A. W., Yang M., Mackenzie J., Mattes J., Hogan S. P., Mahalingam S., Mckenzie A. N. J., Rothenberg M. E., Young I. G., Matthaei K. L. and Webb D. C. Immunol. Rev., 179, 173-181, 2001]. Clinically, expression of eotaxin and CCR3 mRNA and protein is observed in the lung tissues of atopic asthmatics and is associated with AHR, reduced $FEV_1$ and lung eosinophilia [Ying S., Robin D. S., Meng Q., Rottman J., Kennedy R., Ringler D. J., Mackay C. R., Daugherty B. L., Springer M. S., Durham S. R., Williams T. J. and Kay A. B.: Enhanced expression of eotaxin and CCR3 mRNA and protein in atopic asthma. Association with airway hyperresponsiveness and predominant colocalization of eotaxin mRNA to bronchial epithelial and endothelial cells. Eur. J. Immunol., 27, 3507-3516, 1997; Lamkhioued Renzi P. M., AbiYounes S., GarciaZepada E. A., Allakhverdi Z., Ghaffar O., Rothenberg M. D., Luster A. D. and Hamid Q.: Increased expressions of eotaxin in bronchoalveolar lavage and airways of asthmatics contributes to the chemotaxis of eosinophils to the site of inflammation. J. Immunol., 159: 4593-4601, 1997; Jahnz-Royk K., Plusa T. and Mierzejewska J.: Eotaxin in serum of patients with asthma or chronic obstructive pulmonary disease: relationship with eosinophil cationic protein and lung function. Mediators of Inflammation, 9: 175-179, 2000]. In addition, in allergic rhinitis, CCR3-expressing Th2 lymphocytes co-localize with eosinophils in nasal polyps in close proximity to eotaxin-expressing cells [Gerber B. O., Zanni M. P., Uguccioni M., Loetscher M., Mackay C. R., Pichler W. J., Yawalkar N., Baggiolini M. and Moser B.: Functional expression of the eotaxin receptor CCR3 in T lymphocytes co-localizing with eosinophils. CURRENT BIOLOGY 7: 836-843, 1997]. Moreover, viral infections (RSV, influenza virus) which are known risk factors in asthma, result in increased eotaxin expression in lung tissue which is correlated with tissue eosinophilia [Matsukura S., Kokubo F., Kubo H., Tomita T., Tokunaga H., Kadokura M., Yamamoto T., Kuroiwa Y., Ohno T., Suzaki H. and Adachi M.: Expression of RANTES by normal airway epithelial cells after influenza virus A infection. Am. J. Respir. Cell and Mol. Biol., 18: 255-264, 1998; Saito T., Deskin R. W., Casola A., Haeberle H., Olszewska B., Ernest P. B., Alam R., Ogra P. L. and Garofalo R.: Selective regulation of chemokine production in human epithelial cells. J. Infec. Dis., 175: 497-504, 1997].

Thus the binding of CCR3 and related chemokine including eotaxin has been implicated as being important mediators of inflammatory and immunoregulatory disorders and diseases, including asthma, rhinitis, and allergic diseases, as well as autoimmune pathologies such as rheumatoid arthritis, Grave's disease, and athero-sclerosis. It is also implicated that binding of CCR3 and related chemokine is an important factor of virus infections including HIV [(Marone G, de Paulis A, Florio G, Petraroli A, Rossi F, Triggiani M.: Int Arch Allergy Immunol 2001 June;125(2)/89-95), (Li Y et al.,: Blood 2001 Jun. 1; 97(11):3484-90), and (Marone G, Florio G, Petraroli A, Triggiani M, de Paulis A: Trends Immunol 2001 May;22 (5):229-32)], lung granuloma (Ruth J H, Lukacs N W, Warmington K S, Polak T J, Burdick M, Kunkel S L, Strieter R M, Chensue S W:J Immunol 1998 Oct. 15;161 (8):4276-82), and Alzheimer's diseases (Xia M Q, Qin S X, Wu L J, Mackay C R, and Hyman B T: Am J Pathol 1998 July;153 (1):31-37).

Therefore, CCR3 is an important target and antagonism of CCR3 is likely to be effective in the treatment of such inflammatory and immunoregulatory disorders and diseases.

WO 00/76514 and WO 00/76513 disclose cyclopentyl modulators of chemokine receptors including CCR3 activity represented by the general formula:

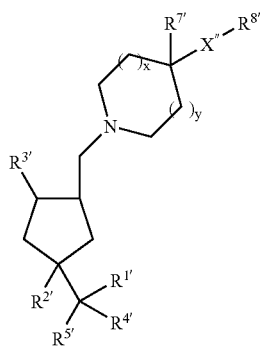

wherein
X″, x, y, R¹·, R²·, R³·, R⁴·, R⁵·, R⁶, R⁷, and R⁸, are defined in the application.

Other applications also disclose CCR3 modulators.

However, none of the reference and other reference discloses simple sulfonamide derivatives having CCR3 antagonistic activity.

The development of a compound having effective CCR3 antagonistic activity and can be used for the prophylaxis and treatment of diseases associated with CCR3 activity has been desired.

SUMMARY OF THE INVENTION

As the result of extensive studies on chemical modification of sulfonamide derivatives, the present inventors have found that the compounds of the structure related to the present invention have unexpectedly excellent CCR3 antagonistic activity. The present invention has been accomplished based on these findings.

This invention is to provide novel sulfonamide derivatives shown by the following formula (I), its tautomeric and stereoisomeric form, and the salts thereof.

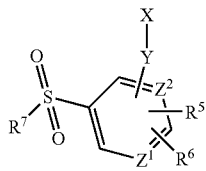

X represents phenyl, which is substituted by 0 to 5 substituents independently selected from the group consisting of $R^1, R^2, R^3, R^4$ and $R^0$ or pyridine, which is substituted by 0 to 5 substituents independently selected from the group consisting of $R^1, R^2, R^3$ and $R^4$
wherein
$R^1$ is hydrogen, halogen, hydroxy, straight- or branched-$C_{1-6}$ alkyl optionally substituted by mono, di or tri halogen, straight- or branched-$C_{1-6}$ alkoxy, straight- or branched-$C_{1-6}$ alkoxy carbonyl, amino, straight- or branched-$C_{1-6}$ alkylamino, di(straight- or branched-$C_{1-6}$ alkyl)amino, straight- or branched-$C_{1-6}$ alkanoyl, nitro, or phenyl,
$R^2$ is hydrogen, halogen, straight- or branched-$C_{1-6}$ alkyl optionally substituted by mono, di or tri halogen, straight- or branched-$C_{1-6}$ alkoxy, or cyano, or
$R^1$ and $R^2$ together form benzene ring or $C_{5-8}$ cycloalkyl fused to the adjacent phenyl or pyridine,
$R^3$ is hydrogen, halogen, or straight- or branched-$C_{1-6}$ alkyl,
$R^4$ is hydrogen, halogen, or straight- or branched-$C_{1-6}$ alkyl,
$R^0$ is hydrogen, halogen, or straight- or branched-$C_{1-6}$ alkyl,
Y represents O, NH, NCH₃ S, S(O), or SO₂;
$Z^1$ represents CH or N;
$Z^2$ represents CH or N
with the proviso that both $Z^1$ and $Z^2$ cannot be N at the same time;
$R^5$ represents hydrogen, halogen, hydroxy, straight- or branched-$C_{1-6}$ alkyl optionally substituted by mono, di or tri halogen or hydroxy, straight- or branched-$C_{1-6}$ alkoxy, straight- or branched-$C_{1-6}$ alkoxycarbonyl, amino, straight- or branched-$C_{1-6}$ alkanoylamino, phenyl-$(CH_2)_q$-carbonylamino (wherein q represents an integer selected from 0 to 6), straight- or branched-$C_{1-6}$ alkylbenzoylamino, naphthylcarbonylamino, thenoylamino, nitro, cyano, carboxy, straight- or branched-$C_{1-6}$ alkyl sulfonyl, oxazolidinonyl, or substituents represented by the formula, —SO₂—NR⁵¹R⁵², or —CO—NR⁵¹R⁵²,
wherein
$R^{51}$ and $R^{52}$ are independently selected from the group consisting of hydrogen, straight- or branched-$C_{1-6}$ alkyl optionally substituted by cyano or carbamoyl and tetrazolyl optionally substituted by $C_{1-6}$ alkylnitrile, or
$R^{51}$ and $R^{52}$ may form, together with the adjacent N, a saturated 5 to 8 membered ring optionally interrupted by NH,
$R^6$ represents hydrogen, halogen, straight or branched $C_{1-6}$ alkyl optionally substituted by mono di or tri halogen, or straight or branched $C_{1-6}$ alkoxy, or
$R^5$ and $R^6$ may form a pyrrol ring fused to adjacent phenyl, or pyridine; and
$R^7$ represents

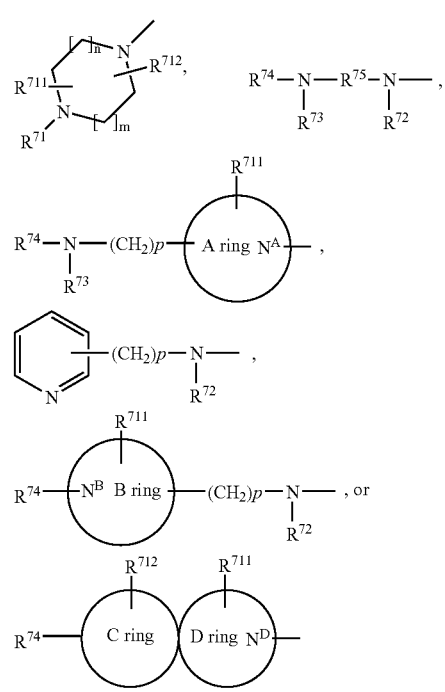

wherein
n represents an integer selected from 1 to 3, m represents an integer selected from 0 to 3,
$R^{71}$ is hydrogen, $C_{3-8}$ cycloalkyl optionally interrupted by NH, N—CH₃ or O, straight- or branched $C_{1-6}$ allkoxycarbonyl, phenyl optionally substituted by straight- or branched $C_{1-6}$ alkyl, benzyl, formyl, or
straight- or branched $C_{1-6}$ alkyl
wherein the alkyl is optionally substituted by hydroxy, straight- or branched-$C_{1-6}$ alkoxy, hydroxy straight- or branched-$C_{1-6}$ alkoxy, carboxy, straight- or branched-$C_{1-6}$ alkoxycarbonyl, straight- or branched-$C_{1-6}$ alkylthio, di(straight- or branched-$C_{1-6}$ alkyl) amino, mono, di or tri halogen, or $C_{3-8}$ cycloalkyl optionally interrupted by NH or O, $R^{711}$ and $R^{712}$ are independently selected from the group consisting of hydrogen, halogen, hydroxy, carboxy, cyano, straight-or branched $C_{1-6}$ alkyl optionally substituted by hydroxy, carboxy, or mono, di or tri halogen, carbamoyl, di (straight-or branched $C_{1-6}$ alkyl)amino carbonyl, and —$NR^{711a}R^{711b}$ wherein
$R^{711a}$ and $R^{711b}$ are independently selected from the group consisting of hydrogen, straight- or branched-$C_{1-6}$ alkyl, straight- or branched-$C_{1-6}$ alkanoyl, and straight- or branched-$C_{1-6}$ alkylsulfonyl, or $R^{71}$ and $R^{711}$ may form, together with the adjacent N atom, a 5 to 8 membered saturated ring;

$R^{72}$ is hydrogen, or straight- or branched-$C_{1-6}$ alkyl;

$R^{73}$ is hydrogen, or straight- or branched-$C_{1-6}$ alkyl, $R^{74}$ is hydrogen, or straight- or branched-$C_{1-6}$ alkyl optionally substituted by phenyl, or $R^{73}$ and $R^{74}$ may form, together with adjacent N atom, a 5 to 8 membered saturated ring optionally substituted by $C_{1-6}$ alkyl and optionally interrupted by NH or O;

$R^{75}$ is straight- or branched-$C_{1-6}$ alkylene or a 3 to 8 membered saturated or unsaturated ring;

p represents an integer selected from 0 to 4;

A ring represents a 3 to 8 membered saturated ring, in which the nitrogen atom $N^A$ is the only hetero atom;

B ring represents a 3 to 8 membered saturated ring, in which the nitrogen atom $N^B$ is the only hetero atom; and C ring and D ring together form a 7 to 12 membered diazabicyclic ring.

A 7 to 12 membered diazabicyclic ring stands for a saturated bicyclic ring system consisting of 5 to 10 carbon atoms and 1 to 2 nitrogen atoms, wherein said bicyclic ring system does not exhibit a spiro ring connection. Preferred are 8 to 10 membered ring systems.

This invention is also to provide a method for treating or preventing a CCR3 related disorder or disease in a human or animal subject, comprising administering to said subject a therapeutically effective amount of the sulfonamide derivative shown in the formula (I), its tautomeric or stereoisomeric form, or a physiologically acceptable salt thereof.

Further this invention is to provide a use of the sulfonamide derivative shown in the formula (I), its tautomeric or stereoisomeric form, or a physiologically acceptable salt thereof in the preparation of a medicament for treating or preventing a CCR3 related disorder or disease.

The compounds of the present invention surprisingly show excellent CCR3 antagonistic activity. They are, therefore suitable for the production of medicament or medical composition, which may be useful to treat CCR3 related diseases.

More specifically, since the compounds of the present invention antagonise CCR3, they are useful for treatment and prophylaxis of diseases as follows:

asthma, rhinitis, and allergic diseases, and autoimmune pathologies such as rheumatoid arthritis, Grave's disease, and atherosclerosis.

Therefore, CCR3 is an important target and antagonism of CCR3 is likely to be effective in the treatment and prophylaxis of such inflammatory and immunoregulatory disorders and diseases.

The compounds of the present invention are also useful for treatment and prophylaxis of diseases like virus infections including HIV, lung granuloma, and Alzheimer's diseases, since the diseases also relate to CCR3.

In another embodiment, the compounds of formula (I) are those wherein:

X, Y, $Z^1$, $Z^2$, $R^1$, $R^2$, $R^3$, $R^4$, $R^0$ and $R^7$ are as defined above,
$R^5$ is chloro, iodo, nitro, or cyano, and
$R^6$ is hydrogen.

In another embodiment, the compounds of formula (I) are those wherein:

X, Y, $Z^1$ and $Z^2$ are as defined above,
$R^1$ is halogen, or straight- or branched-$C_{1-6}$ alkyl optionally substituted by mono, di or tri halogen;
$R^2$ is halogen, or straight- or branched-$C_{1-6}$ alkyl optionally substituted by mono, di or tri halogen;
$R^3$ is hydrogen;
$R^4$ is hydrogen;
$R^0$ is hydrogen;
$R^5$ is halogen, nitro, or cyano;
$R^6$ is hydrogen; and
$R^7$ represents

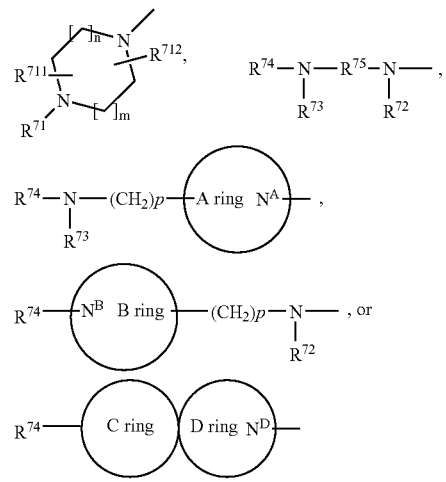

wherein
n represents an integer selected from 1 to 3, m represents an integer selected from 0 to 3, $R^{71}$ is hydrogen, straight- or branched $C_{1-6}$ alkyl optionally substituted by hydroxy or hydroxy straight- or branched-$C_{1-6}$ alkoxy, $C_{3-8}$ cycloalkyl, straight- or branched $C_{1-6}$ alkoxycarbonyl, phenyl optionally substituted by straight- or branched $C_{1-6}$ alkyl, benzyl, or formyl, $R^{711}$ and $R^{712}$ are independently selected from the group consisting of hydrogen, halogen, carboxy, or straighter branched $C_{1-6}$ alkyl, or $R^{71}$ and $R^{711}$ may form, together with the adjacent N atom, a 5 to 8 membered saturated ring;

$R^{72}$ is hydrogen, or straight- or branched-$C_{1-6}$ alkyl, $R^{73}$ is hydrogen, or straight- or branched-$C_{1-6}$ alkyl, $R^{74}$ is hydrogen, or straight- or branched-$C_{1-6}$ alkyl, or $R^{73}$ and $R^{74}$ may form, together with adjacent N atom, a 5 to 8 membered saturated ring optionally interrupted by NH or O;

$R^{75}$ is straight- or branched-$C_{1-6}$ alkylene or a 3 to 8 membered saturated or unsaturated ring;

p represents an integer selected from 0 to 4;

A ring represents a 3 to 8 membered saturated ring, in which the nitrogen atom $N^A$ is the only hetero atom;

B ring represents a 3 to 8 membered saturated ring, in which the nitrogen atom $N^B$ is the only hetero atom; and C ring and D ring together form a 7 to 12 membered diazabicyclic ring.

In another embodiment, the compounds of formula (I) are those wherein:

X, Y, $Z^1$ and $Z^2$ are as defined above, $R^1$ and $R^2$ are identical or different and represent chloro, or methyl;

$R^3$ is hydrogen or fluoro;

$R^4$ is hydrogen;

$R^0$ is hydrogen;

$R^5$ is chloro, iodo, nitro, or cyano;

$R^6$ is hydrogen; and $R^7$ represents

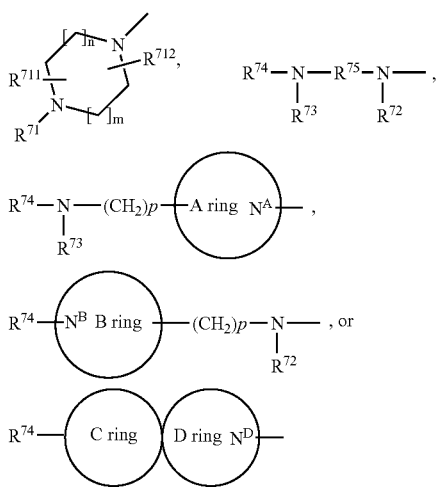

wherein n represents an integer selected from 1 to 3, m represents an integer selected from 0 to 3, $R^{71}$ is hydrogen, straight- or branched $C_1$alkyl optionally substituted by hydroxy or hydroxy straight- or branched-$C_{1-6}$ alkoxy, $C_{3-8}$ cycloalkl, straight- or branched $C_{1-6}$ alkoxycarbonyl, phenyl optionally substituted by straight- or branched $C_{1-6}$ alkyl, benzyl, or formyl, $R^{711}$ and $R^{712}$ are independently selected from the group consisting of hydrogen, halogen, carboxy, or straight- or branched $C_{1-6}$ alkyl, or $R^{71}$ and $R^{711}$ may form, together with the adjacent N atom, a 5 to 8 membered saturated ring;

$R^{72}$ is hydrogen, or straight- or branched-$C_{1-6}$ alkyl;

$R^{73}$ is hydrogen, or straight- or branched-$C_{1-6}$ alkyl, $R^{74}$ is hydrogen, or straight- or branched-$C_{1-6}$ alkyl, or $R^{73}$ and $R^{74}$ may form, together with adjacent N atom, a 5 to 8 membered saturated ring optionally interrupted by NH or O;

$R^{75}$ is straight- or branched-$C_{1-6}$ alkylene or a 3 to 8 membered saturated or unsaturated ring;

p represents an integer selected from 0 to 4;

A ring represents a 3 to 8 membered saturated ring, in which the nitrogen atom $N^A$ is the only hetero atom;

B ring represents a 3 to 8 membered saturated ring, in which the nitrogen atom $N^B$ is the only hetero atom; and C ring and D ring together form a 7 to 12 membered diazabicyclic ring.

In another embodiment, the compounds of formula (I) are those wherein:

X, Y, $Z^1$ and $Z^2$ are as defined above, $R^1$ is hydrogen, fluoro, chloro, bromo, methyl, isopropyl, butyl, tert-butyl, trifluoromethyl, methoxy, amino, dimethylamino, acetyl, or nitro;

$R^2$ is hydrogen, fluoro, chloro, methyl, isopropyl, tert-butyl, trifluoromethyl, methoxy, or cyano;

$R^3$ is hydrogen or fluoro;

$R^4$ is hydrogen;

$R^0$ is hydrogen;

$R^5$ is chloro, iodo, nitro, or cyano;

$R^6$ is hydrogen; and $R^7$ represents

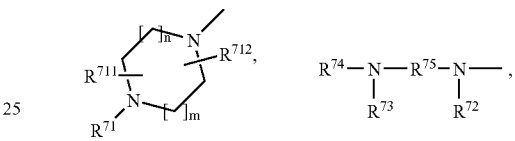

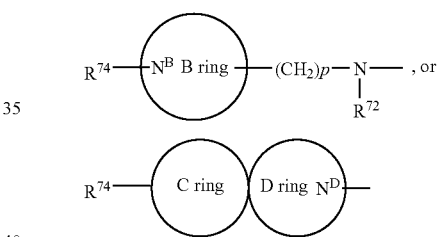

wherein n represents an integer 1, m represents an integer selected from 1 or 2, $R^{71}$ represents hydrogen, methyl, ethyl or isopropyl;

$R^{711}$ represents hydrogen, methyl, or carboxy $R^{712}$ represents hydrogen or methyl, or $R^{71}$ and $R^{711}$ may form, together with the adjacent N atom, a 5 membered saturated ring;

$R^{72}$ is hydrogen, methyl, or ethyl;

$R^{73}$ is hydrogen, or methyl, $R^{74}$ is hydrogen, methyl, or ethyl, or $R^{73}$ and $R^{74}$ may form, together with adjacent N atom, piperidino, morpholino, or pyrrolidino;

$R^{75}$ is phenyl;

p represents an integer selected from 0 to 4;

A ring represents piperidino, or pyrrolidino;

B ring represents pyrrolidino; and

C ring and D ring together form a 7 to 12 membered diazabicyclic ring.

Yet other preferred compounds of formula (I) represent formula (I-2) and are those

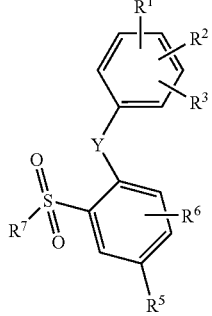
(I-2)

wherein
$R^1$ is hydrogen, halogen, straight- or branched-$C_{1-6}$ alkyl optionally substituted by mono, di or tri halogen, straight- or branched-$C_{1-6}$ alkoxy, straight- or branched-$C_{1-6}$ alkoxy carbonyl, amino, straight- or branched-$C_{1-6}$ alkylamino, di(straight- or branched-$C_{1-6}$ alkyl)amino, straight- or branched-$C_{1-6}$ alkanoyl, or nitro, $R^2$ is hydrogen, halogen, straight- or branched-$C_{1-6}$ alkyl optionally substituted by mono, di or tri halogen, straight- or branched-$C_{1-6}$ alkoxy, or cyano, or $R^1$ and $R^2$ may form benzene ring or $C_{3-8}$ cycloalkyl fused to the adjacent phenyl;

$R^3$ is hydrogen or halogen,

Y represents O, NH, NCH$_3$, S, S(O), or SO$_2$;

$R^5$ is hydrogen, halogen, hydroxy, straight- or branched-$C_{1-6}$ alkyl optionally substituted by mono, di, or tri halogen or hydroxy, straight- or branched-$C_{1-6}$ alkoxy, straight- or branched-$C_{1-6}$ alkoxycarbonyl, amino, straight- or branched-$C_{1-6}$ alkanoylamino, phenyl-(CH$_2$)$_q$-carbonylamino (wherein q represents an integer selected from 0 to 6), straight- or branched-$C_{1-6}$ alkylbenzoylamino, naphthylcarbonylamino, thenoylamino, nitro, cyano, carboxy, straight- or branched-$C_{1-6}$ alkyl sulfonyl, oxazolidinonyl, or substituents represented by the formula, —SO$_2$—NR$^{51}$R$^{52}$, or —CO—NR$^{51}$R$^{52}$, wherein
$R^{51}$ and $R^{52}$ are identical or different and represent hydrogen, straight- or branched-$C_{1-6}$ alkyl optionally substituted by cyano or carbamoyl, tetrazolyl optionally substituted by $C_{1-6}$ alkylnitrile, or $R^{51}$ and $R^{52}$ may form, together with the adjacent N, a saturated 5 to 8 membered ring optionally interrupted by NH, $R^6$ is hydrogen, halogen, straight or branched $C_{1-6}$ alkyl optionally substituted by mono, di or tri halogen, or straight or branched $C_{1-6}$ alkoxy, or $R^5$ and $R^6$ may form a pyrrol ring fused to adjacent phenyl; and $R^7$ represents

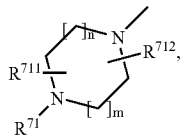 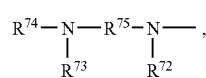

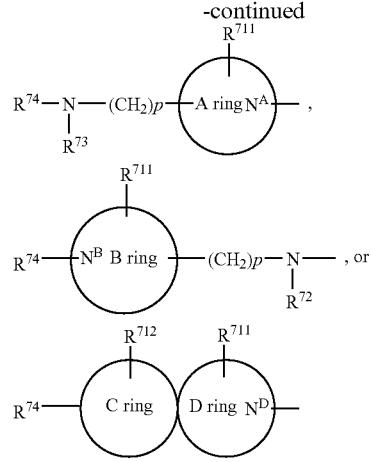

wherein
n represents an integer selected from 1 to 3, m represents an integer selected from 0 to 3, $R^{71}$ is hydrogen, straight- or branched $C_{1-6}$ alkyl optionally substituted by hydroxy or hydroxy straight- or branched-$C_{1-6}$ alkoxy, $C_{3-8}$ cycloalkyl, straight- or branched $C_{1-6}$ alkoxycarbonyl, phenyl optionally substituted by straight- or branched $C_{1-6}$ alkyl, benzyl, or formyl, $R^{711}$ and $R^{712}$ are independently selected from the group consisting of hydrogen, halogen, hydroxy, carboxy, cyano, straight-or branched $C_{1-6}$ alkyl optionally substituted by hydroxy, carboxy, or mono, di or tri halogen, carbamoyl, di (straight-or branched $C_{1-6}$ alkyl) amino carbonyl, or —NR$^{711a}$R$^{711b}$ wherein
$R^{711a}$ and $R^{711b}$ are independently selected from the group consisting of hydrogen, straight- or branched-$C_{1-6}$ alkyl, straight- or branched-$C_{1-6}$ alkanoyl, or straight- or branched-$C_{1-6}$ alkylsulfonyl, or $R^{71}$ and $R^{711}$ may form, together with the adjacent N atom, a 5 to 8 membered saturated ring;

$R^{72}$ is hydrogen, or straight- or branched-$C_{1-6}$ alkyl;

$R^{73}$ is hydrogen, or straight- or branched-$C_{1-6}$ alkyl, $R^{74}$ is hydrogen, or straight- or branched-$C_{1-6}$ alkyl, or $R^{73}$ and $R^{74}$ may form, together with adjacent N atom, a 5 to 8 membered saturated ring optionally interrupted by NH or O;

$R^{75}$ is straight- or branched-$C_{1-6}$ alkylene or a 3 to 8 membered saturated or unsaturated ring;

p represents an integer selected from 0 to 4;

A ring represents a 3 to 8 membered saturated ring, in which the nitrogen atom N$^A$ is the only hetero atom;

B ring represents a 3 to 8 membered saturated ring, in which the nitrogen atom N$^B$ is the only hetero atom; and C ring and D ring together form a 7 to 12 membered diazabicyclic ring.

Yet other preferred compounds of formula (I-2) are those wherein:

$R^1$ is hydrogen, halogen, straight- or branched-$C_{1-6}$ allyl optionally substituted by mono, di or tri halogen, straight- or branched-$C_{1-6}$ alkoxy, straight- or branched-$C_{1-6}$ alkoxy carbonyl, amino, straight- or branched-$C_{1-6}$ alkylamino, di(straight- or branched-$C_{1-6}$ alkyl)amino, straight- or branched-$C_{1-6}$ alkanoyl, or nitro, $R^2$ is hydrogen, halogen, straight- or branched-$C_{1-6}$ alkyl optionally substituted by mono, di or tri halogen, straight- or branched-$C_{1-6}$ alkoxy, or cyano, or $R^1$ and $R^2$ may form benzene ring or $C_{5-8}$ cycloalkyl fused to the adjacent phenyl;

$R^3$ is hydrogen or halogen,

Y represents O, NH, $NCH_3$, S, S(O), or $SO_2$;

$R^5$ is chloro, iodo, nitro, or cyano;

$R^6$ is hydrogen; and $R^7$ represents

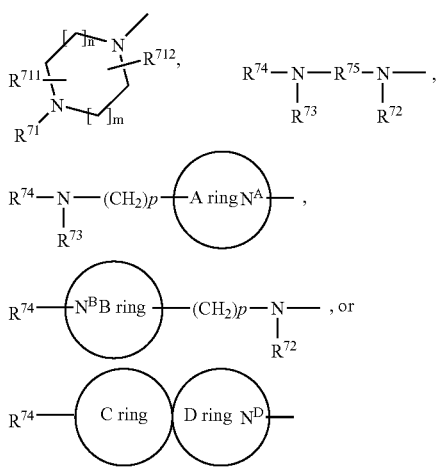

wherein n represents an integer selected from 1 to 3, m represents an integer selected from 0 to 3, $R^{71}$ is hydrogen, straight- or branched $C_{1-6}$ alkyl optionally substituted by hydroxy or hydroxy straight- or branched-$C_{1-6}$ alkoxy, $C_{3-8}$ cycloalkyl, straight- or branched $C_{1-6}$ alkoxycarbonyl, phenyl optionally substituted by straight- or branched $C_{1-6}$ alkyl, benzyl, or formyl, $R^{711}$ and $R^{712}$ are independently selected from the group consisting of hydrogen, halogen, carboxy, or straight-or branched $C_{1-6}$ alkyl, or $R^{71}$ and $R^{711}$ may form, together with the adjacent N atom, a 5 to 8 membered saturated ring;

$R^{72}$ is hydrogen, or straight- or branched-$C_{1-6}$ alkyl;

$R^{73}$ is hydrogen, or straight- or branched-$C_{1-6}$ alkyl, $R^{74}$ is hydrogen, or straight- or branched-$C_{1-6}$ alky, or $R^{73}$ and $R^{74}$ may form with adjacent N atom, a 5 to 8 membered saturated ring optionally interrupted by NH or O;

$R^{75}$ is straight- or branched-$C_{1-6}$ alkylene or a 3 to 8 membered saturated or unsaturated ring;

p represents an integer selected from 0 to 4;

A ring represents a 3 to 8 membered saturated ring, in which the nitrogen atom $N^A$ is the only hetero atom;

B ring represents a 3 to 8 membered saturated ring, in which the nitrogen atom $N^B$ is the only hetero atom; and C ring and D ring together form a 7 to 12 membered diazabicyclic ring.

In another embodiment, the compounds of formula (I-2) are those wherein:

$R^1$ is hydrogen, halogen, or straight- or branched-$C_{1-6}$ alkyl optionally substituted by mono, di or tri halogen;

$R^2$ is hydrogen, halogen, or straight- or branched-$C_{1-6}$ alkyl optionally substituted by mono, di or tri halogen;

$R^3$ is hydrogen or halogen,

Y is O, NH, $NCH_3$, S, S(O), or $SO_2$;

$R^5$ is halogen, nitro, or cyano;

$R^6$ is hydrogen; and $R^7$ represents

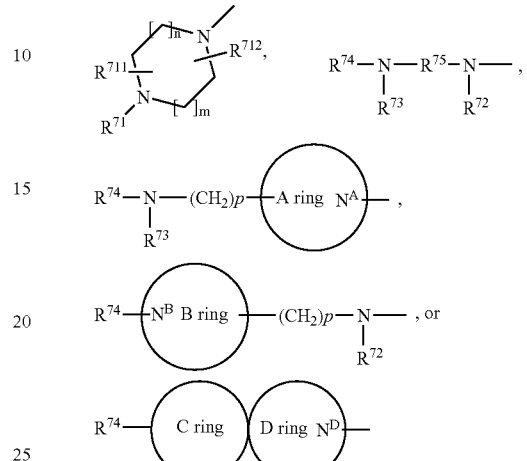

wherein n represents an integer selected from 1 to 3, m represents an integer selected from 0 to 3, $R^{71}$ is hydrogen, straight- or branched $C_{1-6}$ alkyl optionally substituted by hydroxy or hydroxy straight- or branched-$C_{1-6}$ alkoxy, $C_{3-8}$ cycloalkyl, straight- or branched $C_{1-6}$ alkoxycarbonyl, phenyl optionally substituted by straight- or branched $C_{1-6}$ alkyl, benzyl, or formyl, $R^{711}$ represents hydrogen, methyl, or carboxy, $R^{712}$ represents hydrogen or methyl, or $R^{71}$ and $R^{711}$ may form, together with the adjacent N atom, a 5 to 8 membered saturated ring;

$R^{72}$ is hydrogen, or straight- or branched-$C_{1-6}$ alkyl;

$R^{73}$ is hydrogen, or straight- or branched-$C_{1-6}$ alkyl, $R^{74}$ is hydrogen, or straight- or branched-$C_{1-6}$ alkyl, or $R^{73}$ and $R^{74}$ may form with adjacent N atom, a 5 to 8 membered saturated ring optionally interrupted by NH or O;

$R^{75}$ is straight- or branched-$C_1$ alkylene or a 3 to 8 membered saturated or unsaturated ring;

p represents an integer selected from 0 to 4;

A ring represents a 3 to 8 membered saturated ring, in which the nitrogen atom $N^A$ is the only hetero atom;

B ring represents a 3 to 8 membered saturated ring, in which the nitrogen atom $N^B$ is the only hetero atom; and C ring and D ring together form a 7 to 12 membered diazabicyclic ring.

In another embodiment, the compounds of formula (I-2) are those wherein:

$R^1$, $R^2$ and $R^3$ are identical or different and represent hydrogen, chloro, or methyl;

Y is O, NH, $NCH_3$, S, S(O), or $SO_2$;

$R^5$ is chloro, iodo, nitro, or cyano;

$R^6$ is hydrogen; and $R^7$ represents

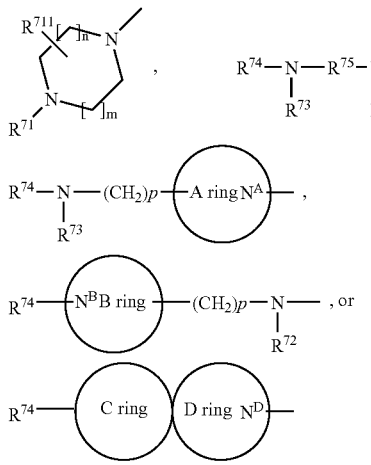

wherein
n represents an integer selected from 1 to 3,
m represents an integer selected from 1 to 3,
$R^{71}$ is hydrogen, straight- or branched $C_{1-6}$ alkyl optionally substituted by hydroxy or hydroxy straight- or branched-$C_{1-6}$ alkoxy, $C_{3-8}$ cycloalkyl, straight- or branched $C_1$ alkoxycarbonyl, phenyl optionally substituted by straight- or branched $C_{1-6}$ alkyl, benzyl, or formyl,
$R^{711}$ represents hydrogen, methyl, or carboxy or
$R^{71}$ and $R^{711}$ may form, together with the adjacent N atom, a 5 to 8 membered saturated ring;
$R^{72}$ is hydrogen, or straight- or branched-$C_{1-6}$ alkyl;
$R^{73}$ is hydrogen, or straight- or branched-$C_{1-6}$ alkyl;
$R^{74}$ is hydrogen, or straight- or branched-$C_{1-6}$ alkyl; or
$R^{73}$ and $R^{74}$ may form, together with adjacent N atom, a 5 to 8 membered saturated ring optionally interrupted by NH or O;
$R^{75}$ is straight- or branched-$C_{1-6}$ alkylene or a 3 to 8 membered saturated or unsaturated ring;
p represents an integer selected from 0 to 4;
A ring represents a 3 to 8 membered saturated ring, in which the nitrogen atom $N^A$ is the only hetero atom;
B ring represents a 3 to 8 membered saturated ring, in which the nitrogen atom $N^B$ is the only hetero atom; and
C ring and D ring together form a 7 to 12 membered diazabicyclic ring.

In another embodiment, the compounds of formula (I-2) are those wherein
$R^1$ is halogen, or straight- or branched-$C_{1-6}$ alkyl optionally substituted by mono, di or tri halogen;
$R^2$ is halogen, or straight- or branched-$C_{1-6}$ alkyl optionally substituted by mono, di or tri halogen;
$R^3$ is hydrogen or fluoro;
Y is O, NH, $NCH_3$, S, S(O), or $SO_2$;
$R^5$ is hydrogen, fluoro, chloro, bromo, iodo, trifluoromethyl, hydroxy, methoxy, amino, acetylamino, isobutylcarbonylamino, tert-butylcarbonylamino, benzoylamino, benzylcarbonylamino, phenethylcarbonylamino, methylbenzoylamino, naphthylcarbonylamino, thenoylamino, nitro, cyano, methylsulfonyl, dimethyaminosulfonyl, piperazinosulfonyl, dimethyaminocarbonyl, or piperazinocarbonyl;
$R^6$ is hydrogen, methyl, or methoxy; or
$R^5$ and $R^6$ may form a pyrrol ring fused to adjacent phenyl; and
$R^7$ represents

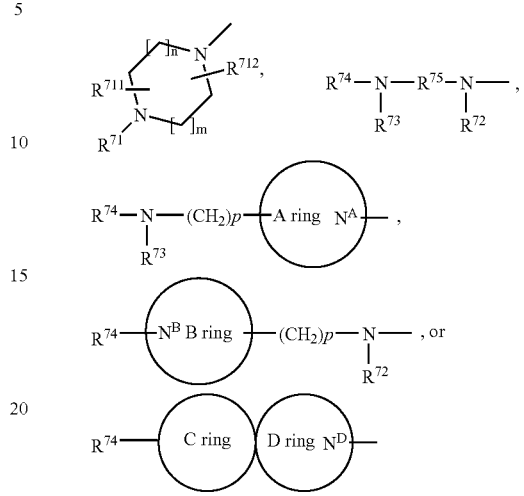

wherein
n represents an integer 1,
m represents an integer 1 or 2,
$R^{71}$ is hydrogen, methyl, ethyl, isopropyl, sec-butyl, branched pentyl, hydroxyethyl, hydroxyethoxyethyl, cyclopentyl, cyclohexyl, tert-butoxycarbonyl, phenyl, tolyl, benzyl, or formyl,
$R^{711}$ represents hydrogen, methyl, or carboxy,
$R^{712}$ represents hydrogen or methyl, or
$R^{71}$ and $R^{711}$ may form, together with the adjacent N atom, a 5 membered saturated ring;
$R^{72}$ is hydrogen, methyl, or ethyl;
$R^{73}$ is hydrogen, or methyl,
$R^{74}$ is hydrogen, methyl, or ethyl, or
$R^{73}$ and $R^{74}$ may form, together with adjacent N atom, piperidino, morpholino, or pyrrolidino;
$R^{75}$ is phenyl;
p represents an integer selected from 0 to 4;
A ring represents piperidino, or pyrrolidino;
B ring represents pyrrolidino; and
C ring and D ring together form a 7 to 12 membered diazabicyclic ring.

In another embodiment, the compounds of formula (I-2) are those wherein;
$R^1$ is hydrogen, fluoro, chloro, bromo, methyl, isopropyl, butyl, tert-butyl, trifluoromethyl, methoxy, amino, dimethylamino, acetyl, or nitro;
$R^2$ is hydrogen, fluoro, chloro, methyl, isopropyl, tert-butyl, trifluoromethyl, methoxy, or cyano;
$R^3$ is hydrogen or fluoro;
Y is O, NH, $NCH_3$, S, S(O), or $SO_2$;
$R^5$ is hydrogen, fluoro, chloro, bromo, iodo, trifluoromethyl, hydroxy, methoxy, amino, acetylamino, isobutylcarbonylamino, tert-butylcarbonylamino, benzoylamino, benzylcarbonylamino, phenethylcarbonylamino, methylbenzoylamino, naphthylcarbonylamino, thenoylamino, nitro, cyano, methylsulfonyl, dimethylaminosulfonyl, piperazinosulfonyl, dimethylaminocarbonyl, or piperazinocarbonyl;
$R^6$ is hydrogen, methyl, or methoxy; or
$R^5$ and $R^6$ may form a pyrrol ring fused to adjacent phenyl, and $R^7$ represents

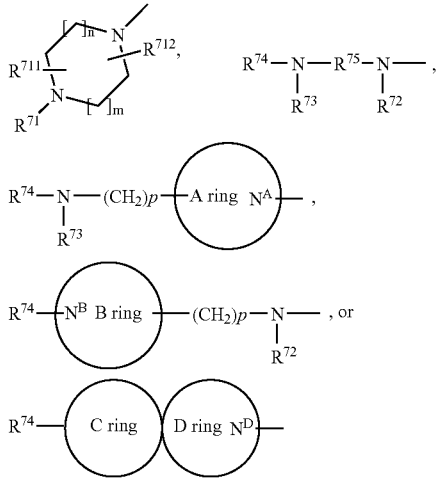

wherein n represents an integer 1, m represents an integer 1 or 2, $R^{71}$ represents hydrogen, methyl, ethyl, isopropyl, sec-butyl, branched pentyl, hydroxyethyl, hydroxyethoxyethyl, cyclopentyl, cyclohexyl, tert-butoxycarbonyl, phenyl, tolyl, benzyl, or formyl, $R^{711}$ represents hydrogen, methyl, or carboxy $R^{712}$ represents hydrogen or methyl, or $R^{71}$ and $R^{711}$ may form, together with the adjacent N atom, a 5 membered saturated ring;

$R^{72}$ is hydrogen, methyl, or ethyl, $R^{73}$ is hydrogen, or methyl, $R^{74}$ is hydrogen, methyl, or ethyl, or $R^{73}$ and $R^{74}$ may form, together with adjacent N atom, piperidino, morpholino, or pyrrolidino;

$R^{75}$ is phenyl;

p represents an integer selected from 0 to 4;

A ring represents piperidino, or pyrrolidino;

B ring represents pyrrolidino; and

C ring and D ring together form a 7 to 12 membered diazabicyclic ring.

In another embodiment, the compounds of formula (I-2) are those wherein;

$R^1$ is chloro, bromo, or methyl;

$R^2$ is hydrogen, chloro, bromo, or methyl;

$R^3$ is hydrogen or fluoro;

Y represents O, S, or S(O);

$R^5$ represents hydrogen, chloro, nitro, or cyano;

$R^6$ represents hydrogen;

$R^7$ represents

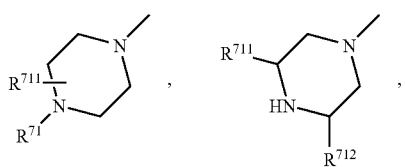

-continued

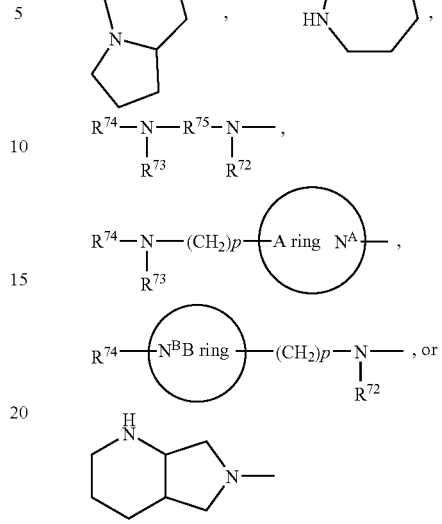

wherein $R^{71}$ represents hydrogen, methyl, ethyl or isopropyl;

$R^{711}$ represents hydrogen, methyl, or carboxy;

$R^{712}$ represents hydrogen or methyl;

$R^{72}$ is hydrogen, methyl, or ethyl;

$R^{73}$ is hydrogen, methyl, or ethyl;

$R^{74}$ is hydrogen, methyl, or ethyl; or $R^{73}$ and $R^{74}$ may form, together with adjacent N atom, piperidino, or pyrrolidino, $R^{75}$ is phenyl;

p represents integer 0 or 1;

A ring represents piperidino, or pyrrolidino; and

B ring represents pyrrolidino.

The preferable compounds of the present invention are as follows:

1-{[2-(3,5-dimethylphenoxy)-5-nitrophenyl]sulfonyl}-4-ethylpiperazine,

1-{[2-(3,5-dichlorophenoxy)-5-nitrophenyl]sulfonyl}piperazine,

1-{[2-(3,5-dimethylphenoxy)-5-nitrophenyl]sulfonyl}-4-isopropylpiperazine, 4-(3,5-dimethylphenoxy)-3-(1-piperazinylsulfonyl)benzonitrile, 1-{[5-chloro-2-(3,5-dimethylphenoxy)phenyl]sulfonyl}-4-ethylpiperazine, 1-{[2-(3,5-dichlorophenoxy)-5-nitrophenyl]sulfonyl}-4-(1-pyrrolidinyl)piperidine, 4-(3,5-dichlorophenoxy)-3-{[4-(1-pyrrolidinyl)-1-piperidinyl]sulfonyl}benzonitrile, 4-(3,5-dichlorophenoxy)-3-(1-piperazinylsulfonyl)benzonitrile, 1-{[2-(3,5-dichlorophenoxy)-5-nitrophenyl]sulfonyl}-N,N-diethyl-3-pyrrolidinamine, (2S)-1-{[2-(3,5-dichlorophenoxy)-5-nitrophenyl]sulfonyl)-2-(1-pyrrolidinylmethyl)pylolidine, 3-[(4aR,7aR)-octahydro-6H-pyrrolo[3,4-b]pyridin-6-ylsulfonyl]-4-(3,5-dichlorophenoxy)benzonitrile, 4-[(3,5-dichlorophenyl)sulfanyl]-3-(1-piperazinylsulfonyl)benzonitrile, 4-[(3,5-dichlorophenyl)sulfinyl]-3-(1-piperazinylsulfonyl)benzonitrile, 1-{[2-(3,5-dibromophenoxy)-5-nitrophenyl]
   sulfonyl}piperazine,
1-{[2-(3,5-dichloro-2-fluorophenoxy)-5-nitropbenyl]
   sulfonyl}piperazine,
1-{[5-cyano-2-(3,5-dichlorophenoxy)phenyl]sulfonyl}-2-
   piperazinecarboxylic acid,
1-{[2-(3,5-dichlorophenoxy)-5-nitrophenyl]sulfonyl}-2-
   piperazinecarboxylic acid,
1-{[2-(3,5-dimethylphenoxy)-5-nitrophenyl]sulfonyl}-1,4-
   diazepane,
1-{[2-(3,5-dichlorophenoxy)-5-nitrophenyl]sulfonyl}-1,4-
   diazepane,
1-{[2-(3,5-dichlorophenoxy)-5-nitrophenyl]sulfonyl}-3,5-
   dimethylpiperazine,
3-(1,4-diazepan-1-ylsulfonyl)-4-(3,5-dichlorophenoxy) ben-
   zonitrile,
1'-{[2-(3,5-dichlorophenoxy)-5-nitrophenyl]sulfonyl}-1,3'-
   bipyrrolidine,
3-(1,3'-bipyrrolidin-1'-ylsulfonyl)-4-(3,5-dichlorophenoxy)
   benzonitrile,
1-({2-[(3,5-dichlorophenyl)sulfanyl]-5-
   nitrophenyl}sulfonyl)-4-(1-pyrrolidinyl)piperidine,
4-(3,5-dichlorophenoxy)-3-(hexahydropyrrolo[1,2-a]
   pyrazin-2(1H)-ylsulfonyl)benzonitrile, and
3-(1,4-diazepan-1-ylsulfonyl)-4-[(3,5-dichlorophenyl)sulfa-
   nyl]benzonitrile, and their tautomeric and stereoisomeric form, and physiologically acceptable salts thereof.

The compound of the formula (I) of the present invention can be prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (3rd Edition)" by Greene and Wuts, John Wiley and Sons, New York 1999.

The compound represented by the general formula (I-a) can be prepared by the Reaction A or A' below.

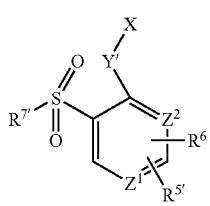

wherein
X, $Z^1$, $Z^2$ and $R^6$ are as defined above, Y' is O, NH, or S, $R^{5'}$ is nitro, $C_{1-6}$ alkyl, $C_{1-6}$ alkylsulfonyl, carboxy and $R^{7'}$ is the same as $R^7$ as defined above or protected $R^7$.

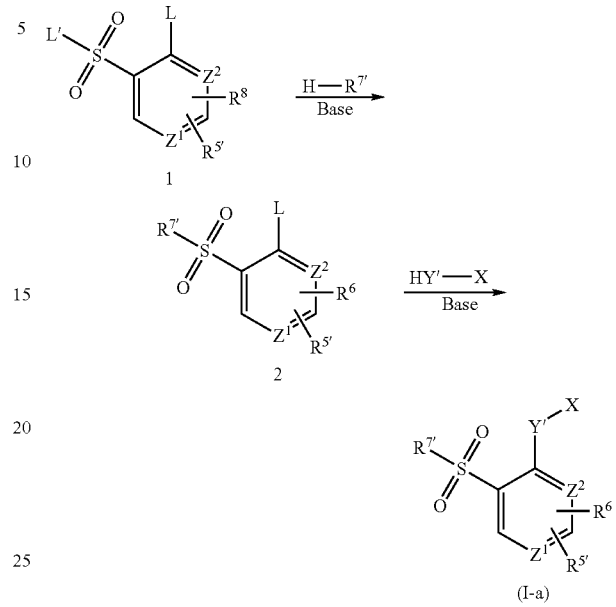

Compound 1 (wherein L and L' are identical or different and represent leaving group, such as halogen atom e.g., fluorine, chlorine, bromine, or iodine atom; $C_{6-10}$ arylsulfonyloxy group e.g., benzenesulfonyloxy, or p-toluenesulfonyloxy, and $C_{1-4}$ alkylsulfonyloxy group, e.g., trifluoromethanesulfonyloxy, methanesulfonyloxy and the like) and H—$R^{7'}$ can be reacted to obtain compound 2 in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; nitriles such as acetonitrile; amides such as N,N-dimethylformamide (DMF), N,N-dimethylacetamide and N-methylpyrrolidone; sulfoxides such as dimethyl sulfoxide, and others. Optionally, two or more of the solvents selected from the listed above can be mixed and used.

The reaction temperature is usually, but not limited to, about −10° C. to 200° C., and preferably about 10° C. to 80° C. The reaction may be carried out for, usually, 30 minutes to 48 hrs and preferably 1 hr to 24 hrs.

The reaction can be advantageously conducted in the presence of a base. The examples of the base include an alkali metal hydride such as sodium hydride or potassium hydride; alkali metal alkoxide such as sodium methoxide, sodium ethoxide and potassium tert-butoxide; alkali metal hydroxide such as sodium hydroxide and potassium hydroxide; carbonates such as sodium carbonate and potassium carbonate; alkali metal hydrogen carbonates such as sodium hydrogen carbonate and potassium hydrogen carbonate; organic amines such as pyridine, triethylamine and N,N-diisopropylethylamine, and others.

Then compound 2 and HY'—X (wherein X and Y' are the same as defined above) can be reacted in a similar manner as that of the reaction of A-1 and H—$R^{7'}$ to obtain the compound (I-a).

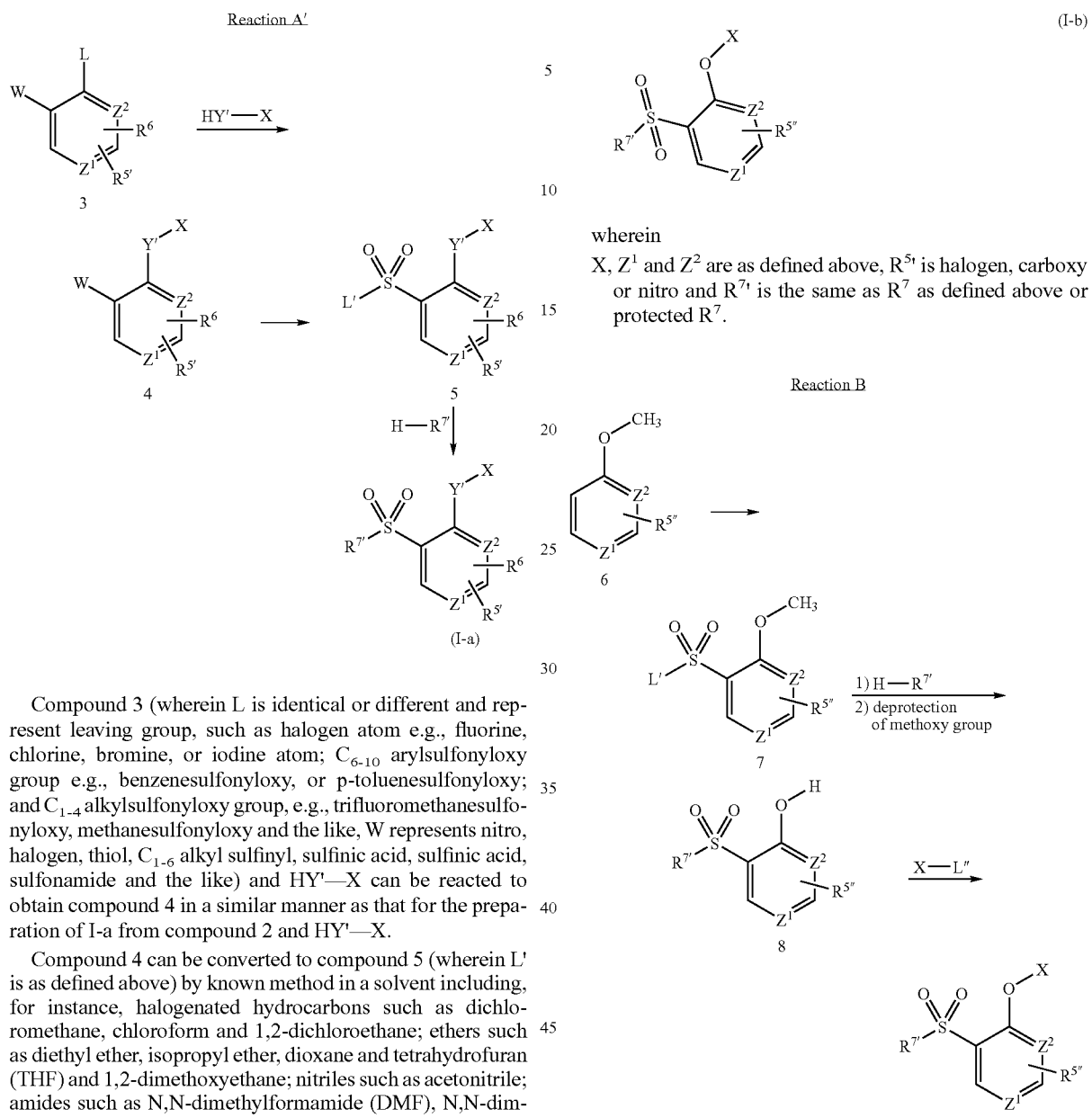

Compound 3 (wherein L is identical or different and represent leaving group, such as halogen atom e.g., fluorine, chlorine, bromine, or iodine atom; $C_{6-10}$ arylsulfonyloxy group e.g., benzenesulfonyloxy, or p-toluenesulfonyloxy; and $C_{1-4}$ alkylsulfonyloxy group, e.g., trifluoromethanesulfonyloxy, methanesulfonyloxy and the like, W represents nitro, halogen, thiol, $C_{1-6}$ alkyl sulfinyl, sulfinic acid, sulfinic acid, sulfonamide and the like) and HY'—X can be reacted to obtain compound 4 in a similar manner as that for the preparation of I-a from compound 2 and HY'—X.

Compound 4 can be converted to compound 5 (wherein L' is as defined above) by known method in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; nitriles such as acetonitrile; amides such as N,N-dimethylformamide (DMF), N,N-dimethylacetamide and N-methylpyrrolidone; sulfoxides such as dimethylsulfoxide (DMSO); organic acid such as acetic acid; inorganic acid such as HCl and $H_2SO_4$; water and others. Optionally, two or more of the solvents selected from the listed above can be mixed and used.

The reaction temperature is usually, but not limited to about −10° C. to 200° C., and preferably about 10° C. to 80° C. The reaction may be carried out for, usually, 30 minutes to 48 hrs and preferably 1 to 24 hrs.

Then compound 5 and H—R$^{7\prime}$ can be reacted to obtain (I-a) in a similar manner as that for the preparation of compound 2 from compound 1 and H—R$^{7\prime}$.

The compound (I-a) can be further reacted to modify R$^{7\prime}$, e.g. to deprotect, or to modify R$^{5\prime}$ to obtain the compound having amino, halogen, hydroxy, cyano, $C_{1-6}$ alkoxy or amide group.

Alternatively, the compound represented by the general formula (I-b) can be prepared by the Reaction B below.

wherein
X, $Z^1$ and $Z^2$ are as defined above, R$^{5\prime}$ is halogen, carboxy or nitro and R$^{7\prime}$ is the same as R$^7$ as defined above or protected R$^7$.

Reaction B is especially advantageous when R$^{5\prime\prime\prime}$ is Br.

First, compound 6 and sulfonic acid halide (e.g., chlorosulfonic acid) or equivalent thereof can be reacted to obtain compound 7 (wherein L' is as defined above) in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; nitriles such as acetonitrile; amides such as N,N-dimethylformamide (DMF), N,N-dimethylacetamide and N-methylpyrrolidone; sulfoxides such as dimethylsulfoxide (DMSO), and others. Optionally, two or more of the solvents selected from the listed above can be mixed and used.

The reaction temperature is usually, but not limited to, about −10° C. to 200° C., and preferably about 10° C. to 80°

C. The reaction may be carried out for, usually, 30 minutes to 48 hrs and preferably 1 to 24 hrs.

Compound 8 can be prepared from compound 7 in two steps; (step 1) the reaction with H—R$^{7\prime}$ and (step 2) deprotection of methoxy group. (step 1) The reaction of compound 7 and H—R$^{7\prime}$ can be performed in a similar manner as that for the preparation of compound 2 from compound 1 and H—R$^{7\prime}$.

(Step 2) The successive deprotection of methoxy group to obtain B-3 can be done by the reaction with Lewis acid such as, for example, BBr$_3$, in a solvent including, for instance, halogenated hydrocarbons such as dichloromethane, chloroform and 1,2-dichloroethane; nitrites such as acetonitrile; amides such as N,N-dimethylformamide (DMF), N,N-dimethylacetamide and N-methylpyrrolidone, and others. Optionally, two or more of the solvents selected from the listed above can be mixed and used.

The reaction temperature is usually, but not limited to about −10° C. to 200° C., and preferably about 10° C. to 80° C. The reaction may be carried out for, usually, 30 minutes to 48 hrs and preferably 1 to 24 hrs.

Then compound 8 can be reacted with X-L" (wherein X is defined as above, L" represents leaving group, such as boronic acid, halogen atom e.g., fluorine, chlorine, bromine, or iodine atom) to obtain the compound (I-b). The reaction can be performed in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitrites such as acetonitrile; amides such as N,N-dimethylformamide (DMF), N,N-dimethylacetamide and N-methylpyrrolidone; sulfoxides such as dimethyl sulfoxide, and others. Optionally, two or more of the solvents selected from the listed above can be mixed and used.

The reaction temperature is usually, but not limited to about −10° C. to 200° C., and preferably about 10° C. to 100° C. The reaction may be carried out for, usually, 30 minutes to 48 hrs and preferably 1 to 24 hrs. The reaction can be carried out in the presence of a catalyst, including for instance, cooper salts such as cooper(II) acetate, palladium salts such as palladium (II) acetate, and others. The reaction can be advantageously conducted in the presence of a base. The examples of the base include an alkali metal alkoxide such as sodium methoxide, sodium ethoxide and potassium tert-butoxide; alkali metal hydroxide such as sodium hydroxide and potassium hydroxide; carbonates such as cesium carbonate, sodium carbonate and potassium carbonate; alkali metal hydrogen carbonates such as sodium hydrogen carbonate and potassium hydrogen carbonate; organic amines such as pyridine, triethylamine and N,N-diisopropylethylamine, and others.

The compound (I-b) can be farther reacted to modify R$^{7\prime}$, e.g. to deprotect, or to modify R$^{5\prime\prime}$ to obtain the compound having amino, halogen, hydroxy, cyano, C$_{1-6}$ alkoxy or amide group.

The compound (I-c) below can be advantageously prepared by the Reaction C below.

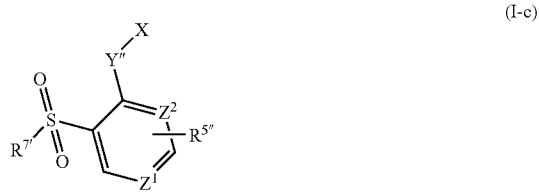

wherein

X, Z$^1$, Z$^2$ and R$^{5\prime\prime}$ are as defined above, Y" is NH or S, and R$^{7\prime}$ is the same as R$^7$ as defined above or protected R$^7$.

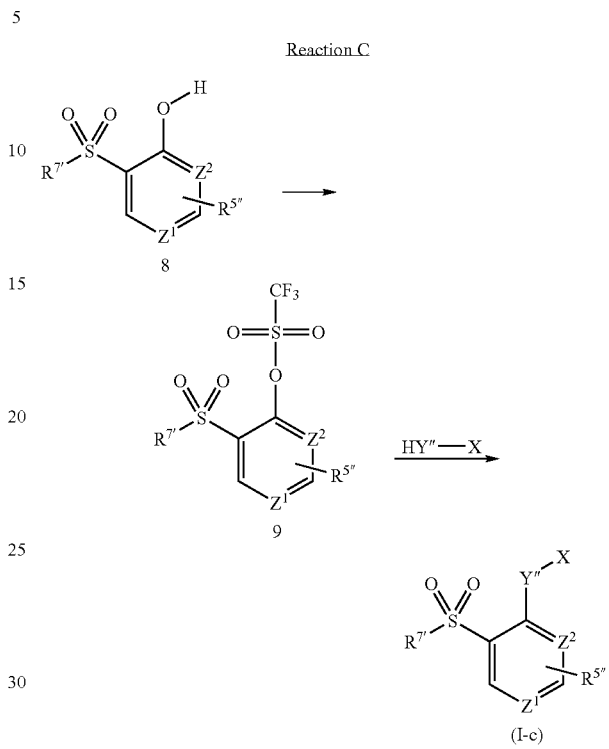

First, compound 8, which can be prepared as described in the Reaction B can be reacted with either trifluoromethanesulfonic anhydride or trifluoromethanesulfonic chloride to obtain compound 9. The reaction can be performed in a solvent including, for instance, halogenated hydrocarbons such as dichloromethane, chloroform and 1,2-dichloroethane; ethers such as diethyl ether, isopropyl ether, dioxane and tetrahydrofuran (THF) and 1,2-dimethoxyethane; aromatic hydrocarbons such as benzene, toluene and xylene; nitriles such as acetonitrile; amides such as N,N-dimethylformamide (DMF), N,N-dimethylacetamide and N-methylpyrrolidone; sulfoxides such as dimethyl sulfoxide, and others. Optionally, two or more of the solvents selected from the listed above can be mixed and used.

The reaction temperature is usually, but not limited to about −10° C. to 200° C., and preferably about 0° C. to 100° C. The reaction may be carried out for, usually, 30 minutes to 48 hrs and preferably 1 to 24 hrs. The reaction can be advantageously conducted in the presence of a base. The examples of the base include organic amines such as pyridine, triethylamine and N,N-diisopropylethylamine, and others.

Then compound 9 and HY"—X can be reacted to obtain compound (I-c) in a similar manner as that for I-a from compound 2 and HY'—X.

The compound (I-c) can be further reacted to modify R$^{7\prime}$, e.g. to deprotect, or to modif R$^{5\prime\prime}$ to obtain the compound having amino, halogen, hydroxy, cyano, C$_{1-6}$ alkoxy or amide group.

The compound (I-d) below can be prepared by the Reaction D below.

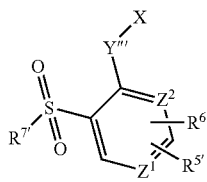

wherein
X, $Z^1$, $Z^2$, $R^5$ and $R^6$ are as defined above, Y''' is SO or $SO_2$ and $R^{7'}$ is the same as $R^7$ as defined above or protected $R^7$.

Reaction D

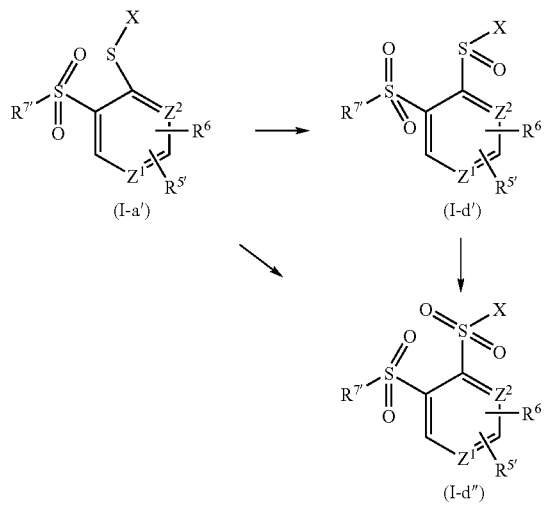

The sulfoxide compounds of the formula (I-d') can be prepared by oxidation of compound (I-a') using appropriate oxidant including but not limited to, peroxide, such as hydrogen peroxide, t-butyl peroxide; peracids such as meta-chloroperbenzoic acid and the like. The reaction can be performed in a solvent including, for instance, halogenated hydrocarbons such as dichloromethane, chloroform and 1,2-dichloroethane; aromatic hydrocarbons such as benzene, toluene and xylene; nitriles such as acetonitrile; amides such as N,N-dimethylformamide (DMF), N,N-dimethylacetamide and N-methylpyrrolidone, and others. Optionally, two or more of the solvents selected from the listed above can be mixed and used.

The reaction temperature is usually, but not limited to about −10° C. to 200° C., and preferably about 0° C. to 100° C. The reaction may be carried out for, usually, 30 minutes to 48 hrs and preferably 1 to 24 hrs.

The sulfone compounds of the formula (I-d'') can be prepared by oxidation of compound (I-a') with an oxidant such as, for example, sodium periodate ($NaIO_4$) or sodium hypochlorite (NaOCl) in the presence of catalyst such as, for instance, ruthenium (III) chloride.

The reaction can be performed in a solvent including, for instance, halogenated hydrocarbons such as dichloromethane, chloroform, carbon tetrachloride and 1,2-dichloroethane; aromatic hydrocarbons such as benzene, toluene and xylene; nitrites such as acetonitrile; amides such as N,N-dimethylformamide (DMF), N,N-dimethylacetamide and N-methylpyrrolidone; water and others. Optionally, two or more of the solvents selected from the listed above can be mixed and used. The reaction temperature is usually, but not limited to about −10° C. to 200° C., and preferably about 0° C. to 100° C. The reaction may be carried out for, usually, 30 minutes to 48 hrs and preferably 1 to 24 hrs.

The sulfone compounds of the formula (I-d'') can also be prepared by oxidation of compound (I-d') in a similar manner as that for the oxidation of compound (I-a').

The compound (I-d') and (I-d'') can be further reacted to modify $R^{7'}$, e.g., to deprotect, or to modify $R^{5'}$ to obtain the compound having amino, halogen, hydroxy, cyano, $C_{1-6}$ alkoxy or amide group.

When the compound shown by the formula (I) or a salt thereof has tautomeric isomers and/or stereoisomers (e.g, geometrical isomers and conformational isomers), each of their separated isomer and mixtures are also included in the scope of the present invention.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydroiodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris (hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Yet another embodiment of the present invention is pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically-acceptable excipients therefore. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

EXAMPLES

The present invention will be described in detail below in the form of examples, but they should by no means be construed as defining the metes and bounds of the present invention.

In the examples below, all quantitative data, if not stated otherwise, relate to percentages by weight.

$^1$H NMR spectra were recorded using either Bruker DRX-300 (300 MHz for $^1$H) spectrometer in $CDCl_3$. Chemical shifts are reported in parts per million (ppm) with tetramethylsilane (TMS) as an internal standard at zero ppm. Coupling constant (J) are given in hertz and the abbreviations s, d, t, q, m, and br refer to singlet, doublet, triplet, quartet, multiplet, and broad, respectively. Mass spectroscopy data were recorded on a FINNIGAN MAT 95. TLC was performed on a precoated silica gel plate (Merck silica gel 60 F-254). Silica gel (WAKO-gel C-200 (75-150 μm)) was used for all column chromatography separations.

All chemicals were reagent grade and were purchased from Sigma-Aldrich, Wako pure chemical industries, Ltd., Tokyo kasei kogyo Co., Ltd., Nacalai tesque, Inc., Watanabe Chemical Ind. Ltd., Maybridge plc, Lancaster Synthesis Ltd., Merck KgaA, Kanto Chemical Co., Ltd.

The effects of the present compounds were examined by the following assays and pharmacological tests.

[Determination of IC50 Values of Compounds in Receptor Binding Assay]

(1) Cell

Human CCR3-transformed K562 cells were used. The cloned CCR3 cDNA was constructed with pcDNA3 vector and transfected into a K562 cell line. The human CCR3-transformed K562 cells were maintained in RPMI-1640 (Cat.#22400-089, Life Technologies) supplemented with 10% FCS (Cat.#A-1115-L, Hyclone), 55 μM 2-mercaptoethanol (Cat.#21985-023, Life Technologies), 1 mM sodium pyruvate (Cat.#11360-070, Life Technologies), 100 units/ml of penicillin G and 100 μg/ml of streptomycin (Cat.#15140-122, Life Technologies), and 0.4 mg/ml of Geneticin (Cat.#10131-035, Life Technologies) (hereinafter called "culture medium"). Before the receptor binding assay, cells were pretreated with 5 mM sodium butyrate (Cat.#193-01522, Wako)-containing the culture medium ($2\times10^5$ cells/ml) for 20-24 hours to increase the expression of CCR3.

(2) Receptor Binding Assay (RBA)

Butyrate-pretreated cells, suspended in binding buffer (25 mM HEPES pH 7.6, 1 mM CaCl$_2$, 5 nM MgCl$_2$, 0.5% BSA, 0.1% NaN$_3$) at a cell density of $2\times10^6$ cells/ml, were added into 60 μl/well in the 96-well round bottom polypropylene plate (Cat.#3365, Costar). Compounds, diluted with the binding buffer (4-times higher concentration of the final concentration), were added into 30 μl/well in the polypropylene plate. [$^{125}$I]-labeled human eotaxin (Cat.#IM290, Amersham Pharmacia Biotech), diluted with the binding buffer at the concentration of 0.4 nM (final concentration; 0.1 nM), was added into 30 μl/well in the polypropylene plate. Total 120 μl/well of binding reaction mixture (60 μl/well of cell suspension, 30 μl/well of compound solution, and 30 μl/well of ($^{125}$I)-labeled eotaxin) were incubated in the polypropylene plate for 1 hour at room temperature after the incubation, 100 μl/well of the reaction mixture was transferred to a filtration plate (Cat.#MAFB-N0B, Millipore), and washed with the washing buffer (25 mM HEPES pH 7.6, 1 m CaCl$_2$, 5 mM MgCl$_2$, 0.5% BSA, 0.1% NaN$_3$, 0.5 M NaCl) twice. The 96-well filtration plate was pretreated with 100 μl/well of 0.5% polyethylenimine (Cat.#P-3143, Sigma) for 2-4 hours at room temperature and washed with the washing buffer twice before use. The non-specific binding was determined by parallel incubation in the presence of 500 nM of non-labeled eotaxin (Cat.#23209, Genzyme Techne). The radioactivities remained on the filter were measured by liquid scintillation counter (TopCount™, Packard) after an addition of 45 μl/well of scintillant (Microscint20, Cat.#6013621, Packard). The inhibition percent at each concentration of compound was calculated and IC50 values were determined from the inhibition curve.

[Determination of IC50 Values of Compounds in Calcium Mobilization assay] (IC$_{50}$ Ca2+)

(1) Cell

Human CCR3-transformed K562 cells were used. The human CCR3-transformed K562 cells were maintained in RPMI-1640 supplemented with 10% FCS, 55 μM 2-mercaptoethanol (Cat.921985-023, Life Technologies), 1 mM sodium pyruvate, 100 units/ml of penicillin G and 100 μg/ml of streptomycin and 0.4 mg/ml of Geneticin. Before the calcium mobilization assay, cells were pretreated with 5 mM sodium butyrate-containing the culture medium ($2\times10^5$ cells/ml) for 20-24 hours to increase the expression of CCR3.

(2) Calcium Mobilization Assay

Butyrate-pretreated cells were loaded with Fluo-3AM (Cat.#F-1242, Molecular Probes) in loading buffer (Hanks' solution Cat.#05906 Nissui, 20 mM HEPES pH 7.6, 0.1% BSA, 1 mM probenecid Cat.#P-8761 Sigma, 1 μM Fluo-3AM, 0.01% pluronic F-127 Cat.#P-6866 Molecular Probes) at a cell density of $1\times10^7$ cells/ml. Then, cells were washed with calcium assay buffer (Hanks' solution Cat.#05906 Nissui, 20 mM HEPES pH 7.6, 0.1% BSA, 1 mM Probenecid Cat.#P-8761 Sigma). The cell suspension ($3.3\times10^6$ cells/ml) was added into 60 μl/well in the 96-well clear bottom black plate (Cat.#3904, Costar). Compounds, diluted (5-times concentration of the final concentration) with the calcium assay buffer, were added into 20 μl/well in the plate 10 minutes before assay. Human recombinant eotaxin, diluted with the calcium assay buffer at the concentration of 50 nM (final concentration; 10 nM), was added into in a polypropylene plate (Cat.#3365, Costar). Mobilization of cytoplasmic calcium was measured by FDSS-6000 or FDSS-3000(Hamamatsu Photonics) over 60 sec after the stimulation with 10 nM eotaxin. The inhibition percent at the each concentration of compound was calculated, and IC50 values were determined from the inhibition curve.

[Determination of IC50 Values of Compounds in Chemotaxis Assay]

(1) Cell

Human CCR3-transformed L1.2 cells were used. Human CCR3-expressing L1.2 stable transformant was established by electroporation, referring to the methods described in J. Exp. Med. 183:2437-2448, 1996. The human CCR3-transformed L1.2 cells were maintained in RPMI-1640 supplemented with 10% FCS, 100 units/ml of penicillin G and 100 μg/ml of streptomycin, and 0.4 mg/ml of Geneticin. One day before the chemotaxis assay, cells were pretreated with 5 mM sodium butyrate-containing culture medium ($5\times10^5$ cells/ml) for 20-24 hours to increase the expression of CCR3.

(2) Chemotaxis Assay

Butyrate-pretreated cells were suspended in chemotaxis buffer (Hanks' solution Cat.#05906 Nissui, 20 mM HEPES pH 7.6, 0.1% human serum albumin Cat.#A-1887 Sigma) at a cell density of $1.1\times10^7$ cells/ml. A mixture of 90 μl of cell suspension and 10 μl of compound solution diluted with chemotaxis buffer (10-times concentration of the final concentration) were preincubated for 10 minutes at 37° C. The mixture of cells and compounds was added into the upper chamber of the 24-well chemotaxis chamber (Transwell™, Cat.#3421, Costar, pore size; 5 μm). 0.5 ml of 10 nM of human recombinant eotaxin(Cat.#23209, Genzyme Techne) solution, diluted with chemotaxis buffer, was added into the lower chamber of the chemotaxis plate. Then, chemotaxis was performed in CO$_2$ incubator at 37° C. for 4 hours. After 4 hrs incubation, migrated cells were counted using FACScan (Becton Dickinson). The inhibition percent at the each concentration of compound was calculated, and IC50 values were determined from the inhibition curve.

[Selectivity Test]

Selectivity test was done in calcium mobilization assay and in receptor binding assay by using CCR1, CCR2, CCR4, CCR5, CCR7, CCR8, CXCR1 and PAR-1 (peptidase activate receptor) stable transformants. Methods for the test are the same as that of CCR3. Only the difference is that different stable transformants were used for these selectivity tests.

[Determination of IC50 Values of Compounds in Chemotaxis Assay with the Use of Human Eosinophils]

Human eosinophils were purified from peripheral blood. Twenty five ml of heparinized blood was layered on 15 ml of Mono-Poly Resolving Medium (#16-980-49DN, ICN Biomedicals Co. Ltd, Japan) in 50 ml tube (#2335-050, Iwaki, Japan) gently and then centrifuged at 400G, for 20 min, at room temperature. After centrifugation, red blood cells were removed by hypotonic lysis. The polymorphonuclear leukocyte pellet was incubated with anti-human CD16 Microbeads (#130-045-701, Milteynyi Biotec GmbH, Germany) for 30 min at 4° C. After washing the cells, magnetically labeled neutrophils were then depleted by applying the cell suspension to BS columns (#130-041-304, Milteynyi Biotec GmbH, Germany) attached to VarioMACS (#130-090-282, Milteynyi Biotec GmbH, Germany).

Chemotaxis assay with the use of the obtained eosinophils was done by the same protocols as that using CCR3 stable transformants, L1.2 cells.

[Primate Chronic Asthma Model: Protocol]

Materials and Methods: The animals used in this study were wild caught, adult male cynomolgus monkeys (*Macaca fascicularis*) weighing 4.0 to 9.0 kg (Charles River BRF, Inc.). All animals studied demonstrated a naturally occurring respiratory sensitivity to inhaled *Ascaris suum* extract. Animals were housed individually in environmentally controlled rooms in open mesh cages and provided food twice daily and water ad libitum. Each animal was fasted for approximately 12 hours prior to the day of study. For each study the animals were anesthetized with ketamine hydrochloride (7 mg/kg, i.m.; Ketaset, Fort Dodge, Iowa) and xylazine (1.2 mg/kg, i.m.; Bayer Corp., Elkart, Ind.), incubated with a cuffed endotracheal tube (5.0 mm ID; Mallinckrodt Critical Care, Glen Falls, N.Y.) and seated in a specially designed support chair. Ketamine (5 mg/kg, i.m.) was used to supplement anesthesia as needed.

Study Protocol: Airway responsiveness (AR) to inhaled methachroline followed by bronchoalveolar lavage (BAL) to assess airway cellular composition (ACC) were determined 3 days before (day 0) and 3 days after (day 10) three alternate-day (days 3,5,7) inhalations of *Ascaris suum* extract. Animals were rested 6 to 8 weeks between studies to allow airway responsiveness and inflammation to return to baseline (pre-antigen) levels. Treatment studies were bracketed by vehicle control studies to assure that no changes in sensitivity to antigen occurred over time.

The test compounds dissolved in Ethanol:PEG400:Water (10:50:40 v/v) were administered under light anesthetisia Aerosol Delivery System and Inhalation Challenges: Aerosol inhalation challenges were administered by intermittent positive pressure breathing with a Bird Mark 7A respirator and micronebulizer (model 8158). Each challenge consisted of 30 breaths (maximum inspiratory pressure=20 cmH$_2$O). *Ascaris suum* extract (Greer Laboratories, Lenoir, N.C.) was diluted with PBS to a final threshold concentration previously determined for each animal and administered as an aerosol (particle size <2 μm). Methacholine (Sigma Chemical Co, St. Louis, Mo.) was dissolved in PBS at a concentration of 100 mg/ml and serial dilutions of 30, 10, 3, 1, 0.3 and 0.1 mg/ml were subsequently prepared for nebulization.

Measurement of Respiratory System Resistance (Rrs): The animal was connected to a Harvard Ventilator (Harvard Apparatus, S. Natick, Mass.) via the endotracheal tube and ventilated at a rate between 30-35 breaths per minute. Airflow was measured by a Fleisch (Hans Rudolph) pneumotachograph and thoracic pressure was measured by a validyne pressure transducer (as the difference between the pressure at the distal end of the endotracheal tube and room pressure). The pneumotachograph and validyne were connected to a pre-amplifier and then into an MI$^2$ respiratory analyzer (Malvern, Pa.). Using the primary signals of flow and pressure the analyzer computed airway resistance and compliance (as well as a number of other respiratory parameters).

Methacholine Dose Response Determinations: To assess airway responsiveness to inhaled methacholine, cumulative dose response curves were constructed by administering increasing concentrations of methacholine until increases in Rrs of between 100 and 200% were obtained. A vehicle control challenge was performed prior to the first dose of methacholine. Changes in Rrs were measured continuously over a 10 minute period post aerosol challenge. Aerosol challenges were separated by 5 to 10 minutes or until Rrs returned to baseline values.

Determination of PC$_{100}$ Values: The resistance obtained with PBS was set as zero. The percentage increase in resistance above zero at each dose of methacholine was entered into the computer and the program used an algorithm to determine the exact methacholine concentration which caused an increase in resistance of 100% above baseline (PC$_{100}$). Differences (day 10-day 0) in PC$_{100}$ values were calculated as logs (base 10) to normalize the data and account for the large variation in absolute values for the PC$_{100}$ between animals.

Bronchoalveolar Lavage. Following methacholine dose response determinations each monkey was placed in the supine position and a fiberoptic bronchoscope (Olympus Optical, model 3C-10, Lake Success, N.Y.) was guided past the carina and wedged into a fifth to seventh generation bronchus. A total of 15 ml of bicarbonate buffered saline (pH 7.4) was infused and gently aspirated through a channel in the bronchoscope. Collected samples were immediately centrifuged at 2000 rpm for 10 minutes at 4° C. The resulting pellets were resuspended in Ca++ and Mg++ free Hank's balanced salt solution. To avoid possible effects of the BAL procedure on lung cellular composition, BAL was performed on alternating right and left lungs. Total white cells per milliliter of BAL fluid was obtained using a Coulter counter (Coulter Corp., Miami, Fla.). BAL cell composition was determined by counting a minimum of 200 cells from a Wright's stained cytospin slide preparation.

Blood Samples: Blood samples were collected prior to and 30 minutes, 1 hr and 2 hr after the first dose of the test compounds (morning of day 2), immediately before each subsequent dose, and 30 minutes, 1 hr and 2 hr after the final dose (evening of day 9). Blood was collected from the femoral vein into EDTA, centrifuged at 1500 rpm for 15 minutes at 4° C. and the plasma stored at −70° C. until assayed for the test compounds.

Statistical Analysis: All data were evaluated statistically with the use of students t-test where a p value <0.05 was considered statistically significant.

Results of receptor binding assay (RBA), Ca$^{2+}$ mobilization assay (Ca$^{2+}$) are shown in Examples and tables of the Examples below. The data corresponds to the compounds as yielded by solid phase synthesis and thus to levels of purity of about 40 to 90%. For practical reasons, the compounds are grouped in three classes of activity as follows:

IC$_{50}$=A1 μM<B10 μM<C

The compounds of the present invention also show more than 100-fold selectivity against CCR1, CCR5, CCR7. CCR8 and CXCR1 in receptor binding assays.

The compounds of the present invention show dose-dependent inhibitory effect on eotaxin-induced chemotaxis of human eosinophils and strong activity in vivo assays.

Example 1-1

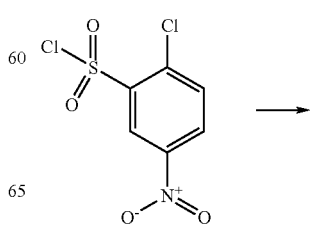

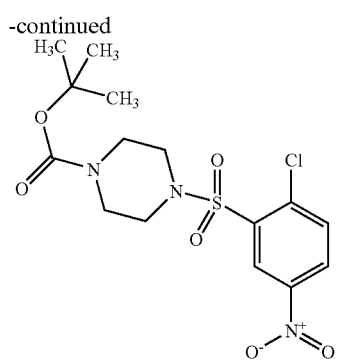

(1) To the solution of 2-chloro-5-nitrobenzenesulfonyl chloride (3.84 g, 15 mmol) in dry THF (30 ml) was added dropwise the mixture of Boc-piperazine (3.07 g, 16.5 mmol) and N,N-diisopropylethylamine (2.33 g, 18 mmol) in dry THF (10 ml) at 0° C. with stirring. The mixture was then stirred at room temperature for 3 hrs. The solvent was evaporated and $CH_2Cl_2$ was added to the residue. The mixture was washed with 0.5 N aqueous HCl, brine, saturated aqueous $NaHCO_3$, brine, successively, dried over $MgSO_4$. The solvent was evaporated to give tert-butyl 4-[(2-chloro-5-nitrophenyl)sulfonyl]-1-piperazinecarboxylate as white powder (5.80 g, 95.3%).

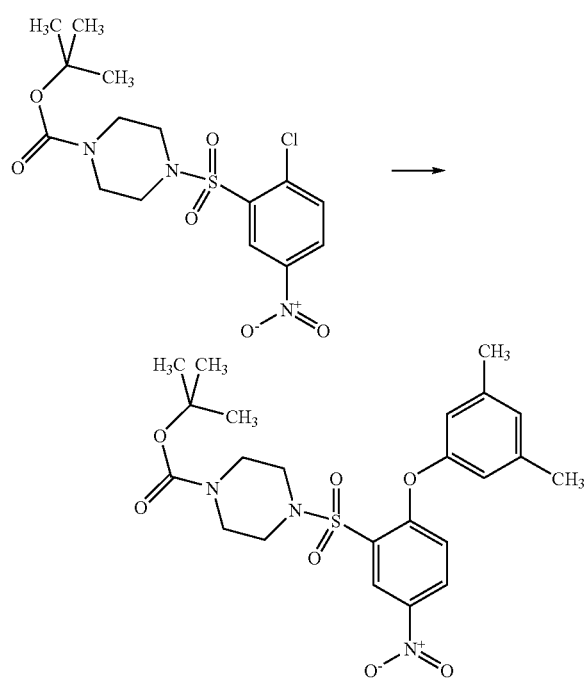

(2) To the solution of 3,5-dimethylphenol (1.92 g, 15.72 mmol) in DMF (50 ml) was added NaH (60%, 0.629 g, 15.72 mmol) at 0° C. with stirring. tert-Butyl 4-[(2-chloro-5-nitrophenyl)sulfonyl]-1-piperazinecarboxylate (5.80 g, 14.29 mmol) was added to the mixture after 30 min. The mixture was stirred at room temperature for 2 hrs. 100 ml of ice water was added, the precipitate was collected by filtration, washed with water and dried in vacuo to give tert-butyl 4-([2-(3,5-dimethylphenoxy)-5-nitrophenyl]sulfonyl}-1-piperazinecarboxylate as white powder (6.90 g, 98.2%): mp 232-233° C.; $^1$H NMR (500 MHz, CDCl3). 1.45 (9H, s), 2.35 (6H, s), 3.35 (4H, t, J=5 Hz), 3.51 (4H, t, J=5 Hz), 6.72 (2H, s), 6.91-6.95 (2H, m), 8.26 (1H, t), 8.86 (1H, s); HPLC-MS (ESI): Calcd for $C_{23}H_{29}N_3O_7S$ $[M+H]^+$ 492, Found: 492.

Molecular weight: 491.5675

Activity grade RBA: C

Activity grade $Ca^{2+}$: C

Example 1-2

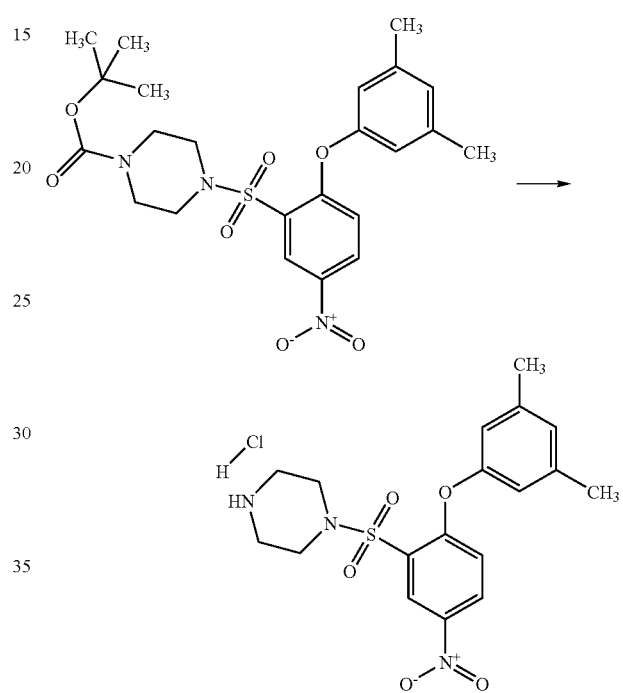

(1) To the suspension of tert-butyl 4-{[2-(3,5-dimethylphenoxy)-5-nitrophenyl]-sulfonyl}-1-piperazinecarboxylate (620 mg, 1.26 mmol) which was prepared in the Example 1-1 in $CH_2Cl_2$ (3 ml) was added trifluoloacetic acid (2 ml) at 0° C., the mixture was stirred at 0° C. for 3 hrs. The solvent was evaporated in vacuo and 20 ml of toluene was added, the solvent was evaporated in vacuo again. To the residue was added $CH_2Cl_2$ (15 ml), and the mixture was cooled to 0° C. 4 N HCl solution in 1,4-dioxane (2 ml) was added and the mixture was stirred for 15 mini at 0° C. The solvent was evaporated, and diethyl ether (5 ml) was added to the residue. The precipitate was collected by filtration and dried to give 1-{[2-(3,5-dimethylphenoxy)-5-nitrophenyl]sulfonyl}piperazine hydrochloride (480 mg, 88.9%): mp 264-266° C.; $^1$H NMR (300 MHz, DMSO-$d_6$) δ 2.33 (6H, s), 3.18 (4H, br), 3.56 (4H, br), 6.96 (2H, s), 7.03-7.05 (2H, m), 8.45 (1H, q, J=9.2 Hz), 8.60 (H, d, J=2.8 Hz), 9.38 (2H, br); HPLC-MS (ESI): Calcd for $C_{18}H_{21}N_3O_5S$ $[M+H]^+$ 392, Found: 392.

Molecular weight: 427.9101

Activity grade RBA: A

Activity grade $Ca^{2+}$: A

In the similar manner as described in Example 1-1 or 1-2 above, compounds in Example 1-3 to 1-100 as shown in Table 1 were synthesized.

TABLE 1
| EX. No. | molstructure | MW | M + 1 | mp | RBA | Ca2+ |
|---|---|---|---|---|---|---|
| 1-3 | 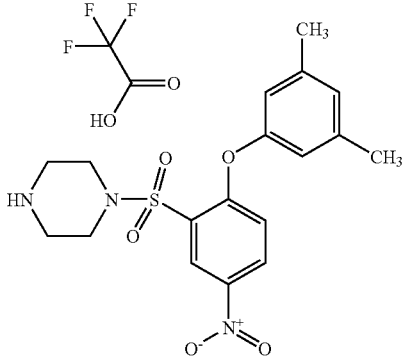 | 505.47344 | 392 | 120-125 | A | A |
| 1-4 | 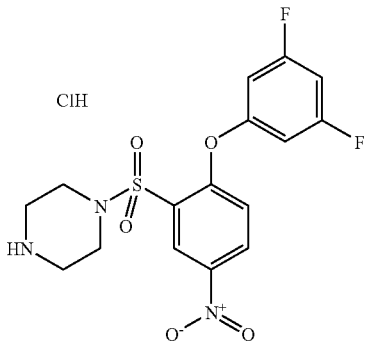 | 435.83682 | 400 | 273-274 | A | A |
| 1-5 | 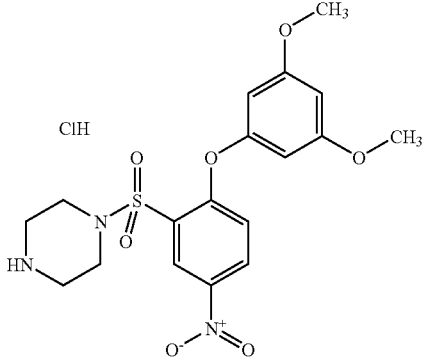 | 459.90894 | 424 | 211-213 | C | C |
| 1-6 | 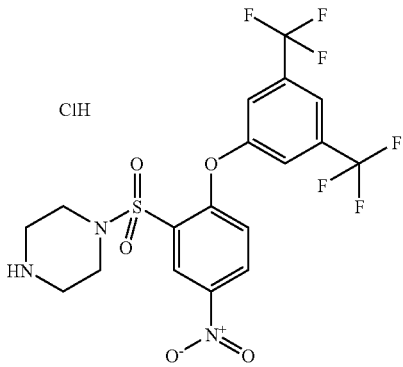 | 535.85272 | 500 | 188-191 | A | A |

TABLE 1-continued

| EX. No. | molstructure | MW | M + 1 | mp | RBA | Ca2+ |
|---|---|---|---|---|---|---|
| 1-7 | | 512.07268 | 476 | 141-143 | C | C |
| 1-8 | | 455.96432 | 420 | 182-185 | A | A |
| 1-9 | | 441.93723 | 406 | 168-170 | A | A |
| 1-10 | | 424.86584 | 389 | 265-267 | B | B |

TABLE 1-continued

| EX. No. | molstructure | MW | M + 1 | mp | RBA | Ca2+ |
|---|---|---|---|---|---|---|
| 1-11 | | 449.9165 | 414 | 196-198 | B | A |
| 1-12 | | 413.88305 | 378 | 167-169 | B | B |
| 1-13 | | 487.79257 | 379 | 246-248 | C | C |
| 1-14 | | 381.38542 | 382 | 118-120 | B | |

TABLE 1-continued

| EX. No. | molstructure | MW | M + 1 | mp | RBA | Ca2+ |
|---|---|---|---|---|---|---|
| 1-15 | | 417.84639 | 382 | 227-229 | B | |
| 1-16 | | 413.88305 | 378 | 188-192 | C | |
| 1-17 | | 413.88305 | 378 | 242-244 | A | |
| 1-18 | | 477.41926 | 363 | | B | B |

TABLE 1-continued
| EX. No. | molstructure | MW | M + 1 | mp | RBA | Ca2+ |
|---|---|---|---|---|---|---|
| 1-19 | 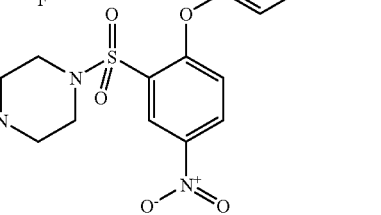 | 407.44575 | 394 | | C | C |
| 1-20 | 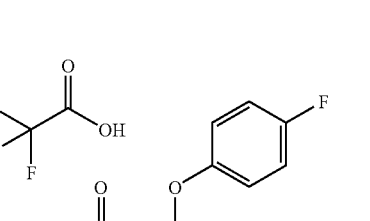 | 495.40969 | 382 | | C | C |
| 1-21 | 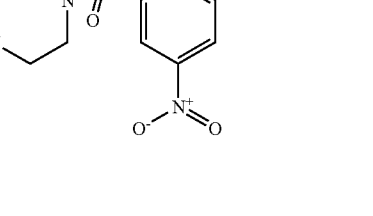 | 533.52762 | 420 | | C | C |
| 1-22 | 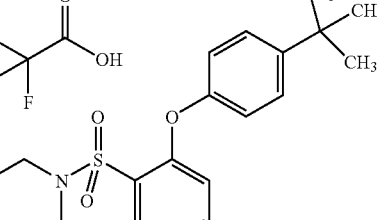 | 511.86429 | 398 | | C | C |

TABLE 1-continued
| EX. No. | molstructure | MW | M + 1 | mp | RBA | Ca2+ |
|---|---|---|---|---|---|---|
| 1-23 | 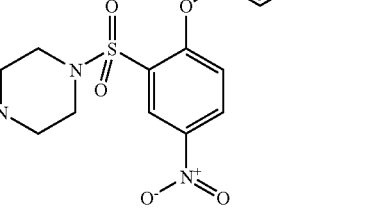 | 502.42914 | | | | |
| 1-24 | 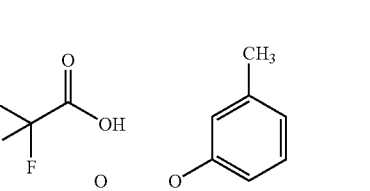 | 491.44635 | 378 | | A | A |
| 1-25 | 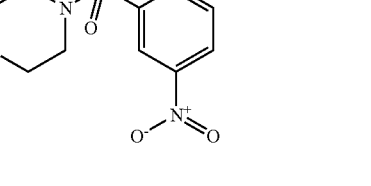 | 495.40969 | 382 | | A | A |
| 1-26 | 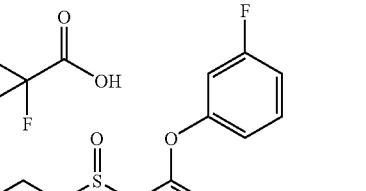 | 567.55814 | 495 | 214-220 | | |

TABLE 1-continued

| EX. No. | molstructure | MW | M + 1 | mp | RBA | Ca2+ |
|---|---|---|---|---|---|---|
| 1-27 | | 429.88245 | 394 | 142 | A | A |
| 1-28 | | 434.30099 | 398 | 166-169 | B | A |
| 1-29 | | 424.86584 | 389 | 133 | B | B |
| 1-30 | | 441.8936 | 406 | 194-200 | C | C |
| 1-31 | | 441.8936 | 406 | 77 | C | C |

TABLE 1-continued

| EX. No. | molstructure | MW | M + 1 | mp | RBA | Ca2+ |
|---|---|---|---|---|---|---|
| 1-32 | | 442.92481 | 407 | 182 | C | B |
| 1-33 | | 468.74602 | 432 | 260-264 | A | A |
| 1-34 | | 467.85434 | 432 | 128 | A | A |
| 1-35 | | 461.0025 | 425 | 267-268 | B | A |
| 1-36 | | 455.96432 | 420 | 155 | B | A |

TABLE 1-continued

| EX. No. | molstructure | MW | M + 1 | mp | RBA | Ca2+ |
|---|---|---|---|---|---|---|
| 1-37 | | 443.90954 | 408 | 113 | A | A |
| 1-38 | | 444.85349 | 409 | 150 | B | A |
| 1-39 | | 478.75199 | 442 | 119 | A | A |
| 1-40 | | 455.96432 | 420 | 140-150 | A | A |

TABLE 1-continued

| EX. No. | molstructure | MW | M + 1 | mp | RBA | Ca2+ |
|---|---|---|---|---|---|---|
| 1-41 | | 382.91261 | 347 | 205-207 | C | B |
| 1-42 | | 531.50589 | 459 | 288-290 | C | C |
| 1-43 | | 450.91099 | 415 | 238-239 | A | A |
| 1-44 | | 441.93723 | 406 | 159 | B | B |

TABLE 1-continued

| EX. No. | molstructure | MW | M + 1 | mp | RBA | Ca2+ |
|---|---|---|---|---|---|---|
| 1-45 | | 482.77311 | 446 | 168 | A | A |
| 1-46 | | 450.91099 | 415 | 250-251 | C | C |
| 1-47 | | 457.93663 | 422 | 188 | B | C |
| 1-48 | | 408.81135 | 471 | 170 | A | A |

TABLE 1-continued

| EX. No. | molstructure | MW | M + 1 | mp | RBA | Ca2+ |
|---|---|---|---|---|---|---|
| 1-49 | | 412.9391 | 377 | 125 | | A |
| 1-50 | | 498.77251 | 462 | 181 | | A |
| 1-51 | | 441.73892 | 405 | 145 | A | A |
| 1-52 | | 396.9397 | 361 | 136 | | A |

TABLE 1-continued

| EX. No. | molstructure | MW | M + 1 | mp | RBA | Ca2+ |
|---|---|---|---|---|---|---|
| 1-53 | | 495.34155 | 423 | amorphous | | B |
| 1-54 | | 455.96432 | 420 | 159 | A | A |
| 1-55 | | 471.74954 | n.d. | 231 | | A |
| 1-56 | | 458.19352 | 421 | 255-257 | A | A |

TABLE 1-continued

| EX. No. | molstructure | MW | M + 1 | mp | RBA | Ca2+ |
|---|---|---|---|---|---|---|
| 1-57 | | 502.64452 | 467 | 269-271 | A | A |
| 1-58 | | 400.90304 | 365 | 204 | | A |
| 1-59 | | 441.73892 | 405 | 306 | | A |
| 1-60 | | 448.32808 | 412 | 204 | B | B |
| 1-61 | | 441.93723 | 406 | 220 | B | B |

TABLE 1-continued

| EX. No. | molstructure | MW | M + 1 | mp | RBA | Ca2+ |
|---|---|---|---|---|---|---|
| 1-62 | | 427.91014 | 392 | 142 | A | A |
| 1-63 | | 427.91014 | 392 | 142 | B | A |
| 1-64 | | 427.91014 | 392 | 141 | A | A |
| 1-65 | | 441.93723 | 406 | 187 | A | A |

TABLE 1-continued
| EX. No. | molstructure | MW | M + 1 | mp | RBA | Ca2+ |
|---|---|---|---|---|---|---|
| 1-66 | 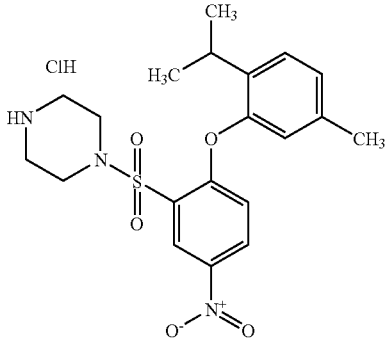 | 455.96432 | 420 | 193 | B | B |
| 1-67 | 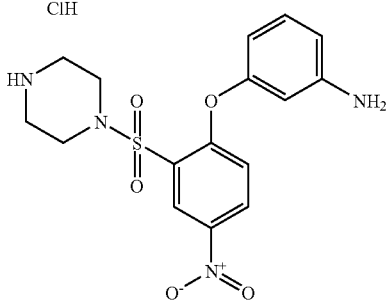 | 414.87063 | 379 | 248 | | A |
| 1-68 | 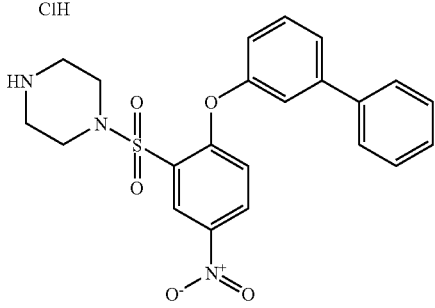 | 475.95474 | 440 | 99 | | A |
| 1-69 | 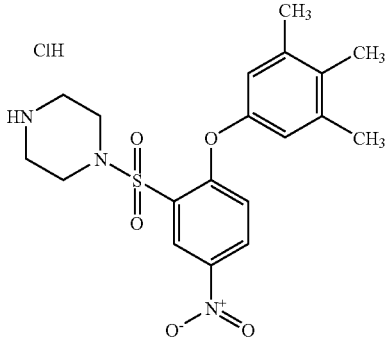 | 441.93723 | 406 | 248 | | A |

TABLE 1-continued
| EX. No. | molstructure | MW | M + 1 | mp | RBA | Ca2+ |
|---|---|---|---|---|---|---|
| 1-70 | 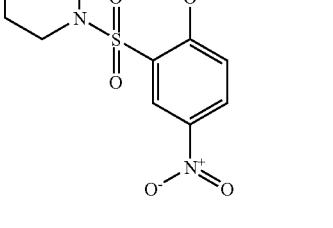 | 414.87063 | 379 | 237 | | A |
| 1-71 | 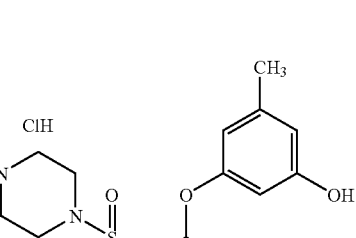 | 429.88245 | 394 | 182 | | A |
| 1-72 | 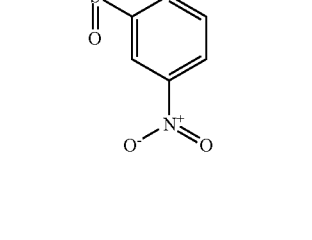 | 453.94838 | 418 | 168 | | A |
| 1-73 | 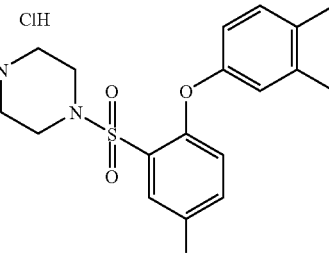 | 489.80811 | 454 | 297 | | A |

TABLE 1-continued

| EX. No. | molstructure | MW | M + 1 | mp | RBA | Ca2+ |
|---|---|---|---|---|---|---|
| 1-74 | | 471.81768 | 436 | 104 | A | A |
| 1-75 | | 458.88058 | 423 | 215 | | A |
| 1-76 | | 557.64802 | 521 | 205 | A | A |
| 1-77 | | 486.73645 | 450 | 263 | A | A |

TABLE 1-continued
| EX. No. | molstructure | MW | M + 1 | mp | RBA | Ca2+ |
|---|---|---|---|---|---|---|
| 1-78 | 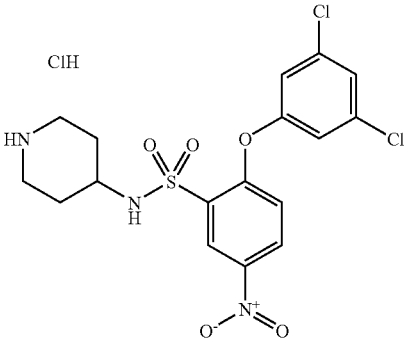 | 482.77311 | 445 | >300 | A | |
| 1-79 | 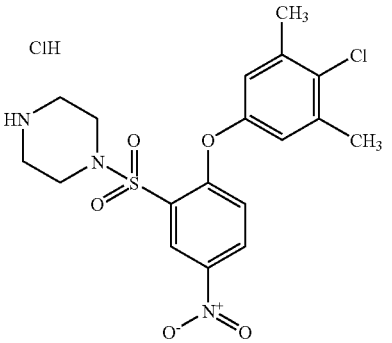 | 462.35517 | 427 | 178-179 | A | A |
| 1-80 | 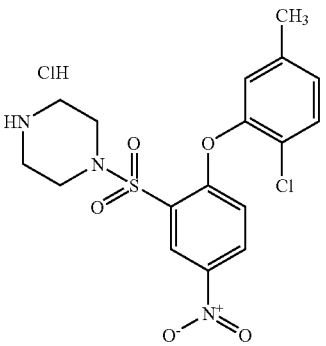 | 448.32808 | 413 | 166-167 | A | A |
| 1-81 | 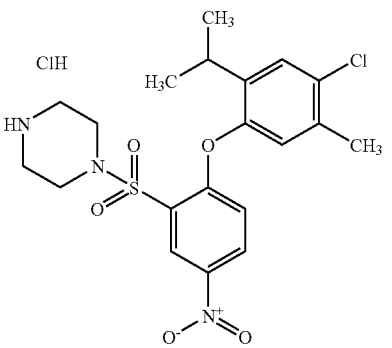 | 490.40935 | 455 | | C | C |

TABLE 1-continued
| EX. No. | molstructure | MW | M + 1 | mp | RBA | Ca2+ |
|---|---|---|---|---|---|---|
| 1-82 | 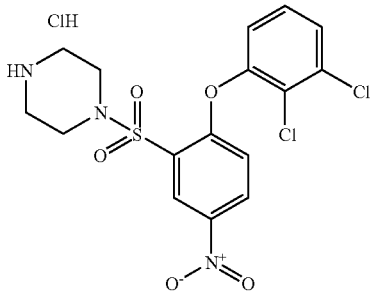 | 468.74602 | 433 | 173-174 | B | |
| 1-83 | 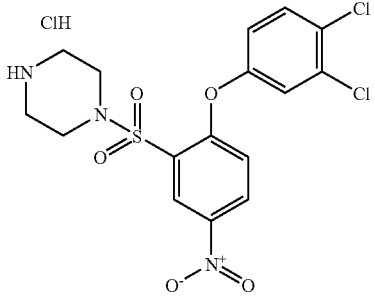 | 468.74602 | 433 | 167-168 | C | |
| 1-84 | 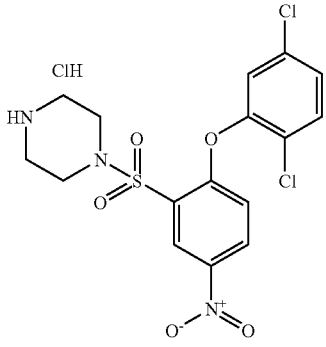 | 468.74602 | 433 | 179-180 | A | A |
| 1-85 | 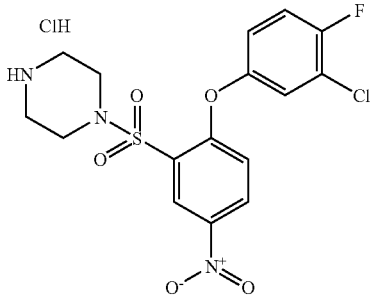 | 452.29142 | 417 | 172-173 | | |

TABLE 1-continued

| EX. No. | molstructure | MW | M + 1 | mp | RBA | Ca2+ |
|---|---|---|---|---|---|---|
| 1-86 | | 503.19105 | 468 | 188-189 | A | A |
| 1-87 | | 512.75597 | 475 | 240-241 | A | A |
| 1-88 | | 435.50275 | 436 | 163-164 | A | A |
| 1-89 | | 479.55633 | 480 | | A | A |

TABLE 1-continued

| EX. No. | molstructure | MW | M + 1 | mp | RBA | Ca2+ |
|---|---|---|---|---|---|---|
| 1-90 | | 441.93723 | 406 | | A | A |
| 1-91 | | 482.77311 | 446 | 261-263 | A | A |
| 1-92 | | 455.96432 | 420 | | A | A |
| 1-93 | | 496.8002 | 460 | | A | A |

TABLE 1-continued

| EX. No. | molstructure | MW | M + 1 | mp | RBA | Ca2+ |
|---|---|---|---|---|---|---|
| 1-94 | | 455.96432 | 420 | >300 | | A |
| 1-95 | | 442.70778 | 446 | 220-221 | | A |
| 1-96 | | 496.8002 | | | | A |
| 1-97 | | 460.33923 | 460 | 148-151 | | A |

TABLE 1-continued
| EX. No. | molstructure | MW | M + 1 | mp | RBA | Ca2+ |
|---|---|---|---|---|---|---|
| 1-98 | | 504.34918 | 504 | 200-201 | | A |
| 1-99 | | 468.74602 | 432 | 247-250 | | A |
| 1-100 | | 468.74602 | 432 | 256-258 | A | A |
Example 2-1
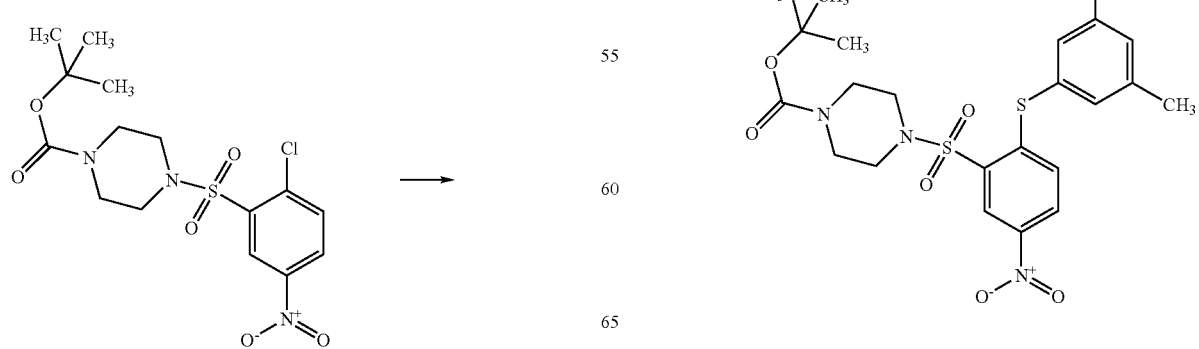

(1) To the solution of 3,5-dimethylthiophenol (82.94 mg, 0.60 mmol) in dry THF (5 ml) was added NaH (60%, 24 mg, 0.60 mmol). tert-Butyl 4-[(2-chloro-5-nitrophenyl)sulfonyl]-1-piperazinecarboxylate (162 mg, 0.4 mmol), which was prepared in the step (1) of Example 1-1, was added to the solution after 10 min. The resulting mixture was stirred at room temperature overnight. 60 mg of $K_2CO_3$ was added and the mixture was stirred at room temperature for 6 hrs. EtOAc was added and the mixture was washed by 10% aqueous $Na_2CO_3$, brine, successively. The organic layer was dried over $MgSO_4$. The solvent was evaporated to 3 ml, the produced white crystal was collected by filtration and dried to give tert-butyl 4-({2-[(3,5-dimethylphenyl)sulfanyl]-5-nitrophenyl}-sulfonyl)-1-piperazinecarboxylate (148 mg, 72.9%).

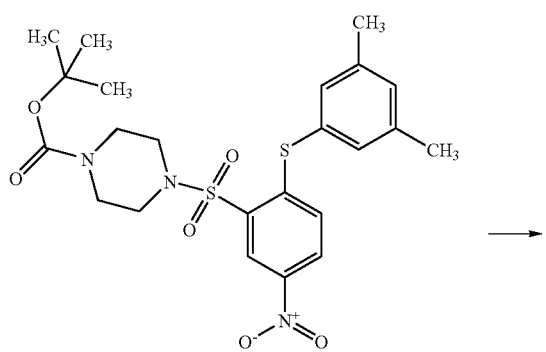

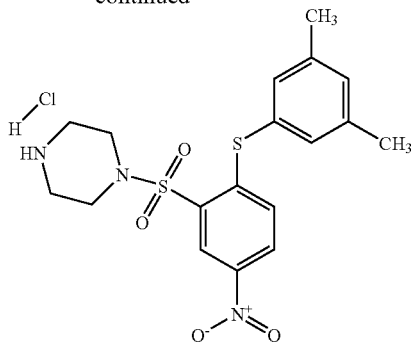

(2) To the solution of tert-butyl 4-({2-[(3,5-dimethylphenyl)sulfanyl]-5-nitrophenyl}sulfonyl)-1-piperazinecarboxylate (100 mg, 0.20 mmol) in dry $CH_2Cl_2$ (3 ml) was added 4 N HCl (0.5 ml) solution in 1,4-dioxane, the mixture was stirred overnight at room temperature. The solvent was evaporated, and 5 ml of diethyl ether was added to the residue. The precipitate was collected by filtration and dried to give 1-({2-[(3,5-dimethylphenyl)sulfanyl]-5-nitrophenyl}sulfonyl)piperazine hydrochloride (82 mg, 93.8%): mp 225-227° C.; $^1$H NMR (300 MHz, DMSO-$d_6$) δ 2.34 (6H, s), 3.18 (4H, br), 3.63 (4H, br), 7.09 (1H, d, J=9 Hz), 7.25 (1H, s), 7.31 (2H, s), 8.30 (1H, q, J=9 Hz), 8.54 (1H, d, J=2), 9.57 (2H, br); HPLC-MS (ES): Calcd for $C_{18}H_{21}N_3O_4S_2$ [M+H]$^+$ 408, Found: 408.

Molecular weight: 443.9747
Activity grade RBA: A
Activity grade $Ca^{2+}$: A

In the similar manner as described in Example 2-1 above, compounds in Example 2-2 to 2-24 as shown in Table 2 were synthesized.

TABLE 2

| EX. No. | molstructure | MW | M + 1 | mp | RBA | Ca2+ |
|---|---|---|---|---|---|---|
| 2-2 | | 532.46856 | 533 | 147-148 | | A |
| 2-3 | | 530.49625 | 531 | 191-192 | A | A |

TABLE 2-continued

| EX. No. | molstructure | MW | M + 1 | mp | RBA | Ca2+ |
|---|---|---|---|---|---|---|
| 2-4 | | 492.44686 | 492 | | | A |
| 2-5 | | 458.77238 | 421 | 189 | | A |
| 2-6 | | 548.46796 | 548 | 156-158 | | A |
| 2-7 | | 476.40383 | 476 | 147-149 | | A |

TABLE 2-continued

| EX. No. | molstructure | MW | M + 1 | mp | RBA | Ca2+ |
|---|---|---|---|---|---|---|
| 2-8 | | 512.8648 | 476 | 205-207 | A | |
| 2-9 | | 520.45741 | 520 | 131-133 | A | |
| 2-10 | | 520.41378 | 520 | 209-211 | A | |
| 2-11 | | 484.81062 | 448 | 270 | A | A |

TABLE 2-continued
| EX. No. | molstructure | MW | M + 1 | mp | RBA | Ca2+ |
|---|---|---|---|---|---|---|
| 2-12 | 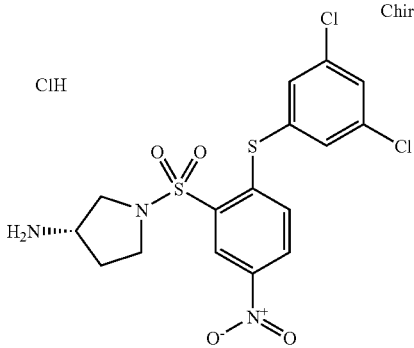 | 484.81062 | 449 | 263 | A | A |
| 2-13 | 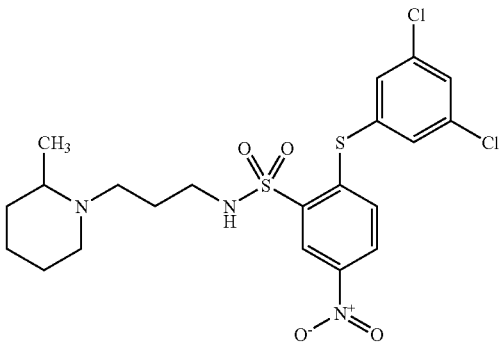 | 518.4851 | 518 |  | A | A |
| 2-14 | 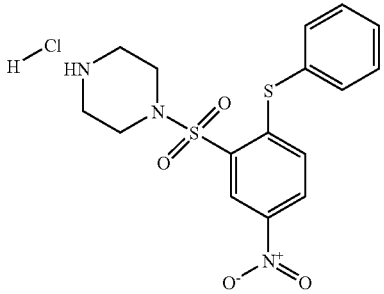 | 415.92056 | 380 |  |  | B |
| 2-15 | 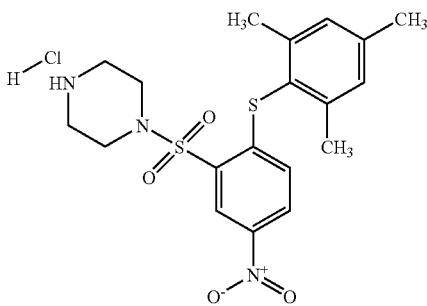 | 458.00183 | 422 | 274 |  | B |

TABLE 2-continued

| EX. No. | molstructure | MW | M + 1 | mp | RBA | Ca2+ |
|---|---|---|---|---|---|---|
| 2-16 | | 429.94765 | 394 | 229-231 | | A |
| 2-17 | | 450.36559 | 414 | 235-237 | | A |
| 2-18 | | 484.81062 | 448 | 262-264 | | A |
| 2-19 | | 433.91099 | 398 | 236-238 | | A |

TABLE 2-continued

| EX. No. | molstructure | MW | M + 1 | mp | RBA | Ca2+ |
|---|---|---|---|---|---|---|
| 2-20 | | 551.91732 | 516 | 230-231 | | A |
| 2-21 | | 465.9811 | 430 | 273 | | B |
| 2-22 | | 516.46916 | 516 | 213 | A | A |
| 2-23 | | 464.39268 | 464 | 102 | A | A |

TABLE 2-continued

| EX. No. | molstructure | MW | M + 1 | mp | RBA | Ca2+ |
|---|---|---|---|---|---|---|
| 2-24 | | 490.43092 | 490 | | A | A |

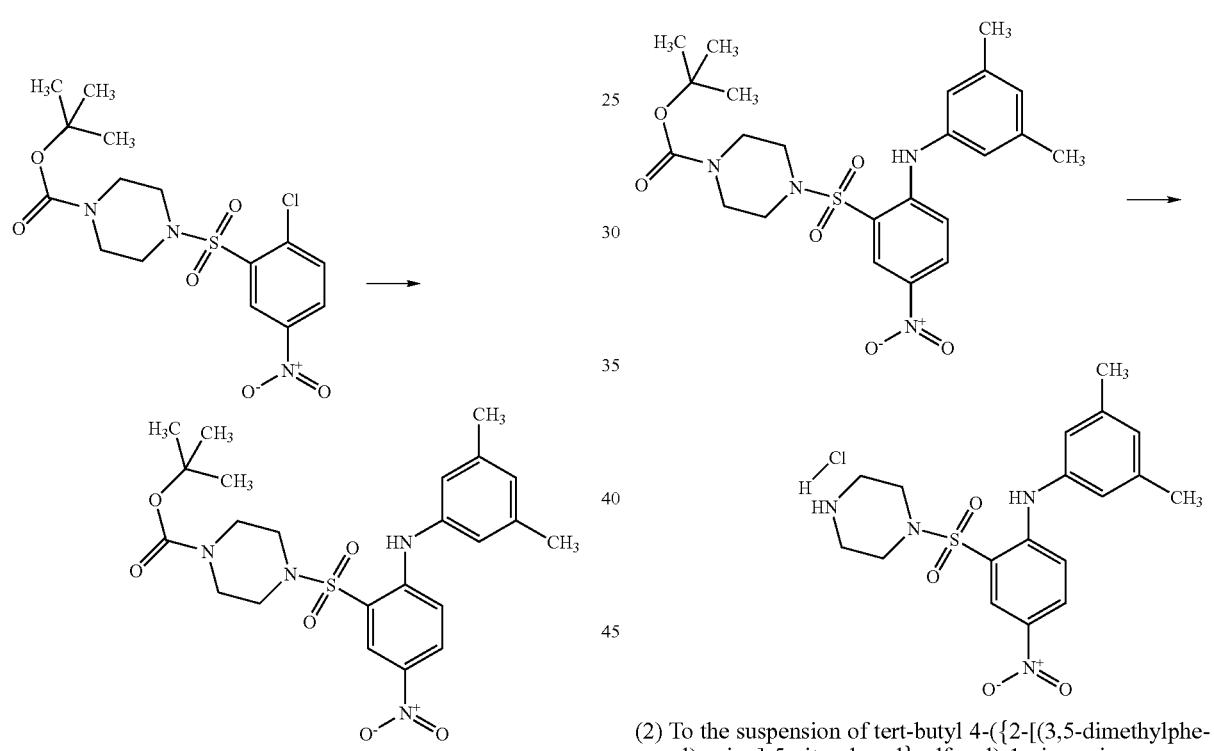

Example 3-1

(1) To the solution of 3,5-dimethylaniline (96.9 mg, 0.80 mmol) in dry THF (15 ml) was added NaH (60%, 24 mg, 0.6 mmol) followed by tert-butyl 4[(2-chloro-5-nitrophenyl)sulfonyl]-1-piperazinecarboxylate (162.3 mg, 0.40 mmol), which was prepared in the step (1) of Example 1-1 and the mixture was stirred at 80° C. for 2 hrs. The solvent was evaporated and 15 ml of ice water was added to the residue. The mixture was extracted with $CH_2Cl_2$. The combined extract was washed with saturated aqueous $NaHCO_3$, brine, successively, dried over $MgSO_4$. The solvent was evaporated and 10 ml of diethyl ether was added to the residue, the produced precipitate was collected by filtration and dried to give tert-butyl 4-({2-[(3,5-dimethylphenyl)amino]-5-nitrophenyl}-sulfonyl)-1-piperazinecarboxylate (110 mg, 56.1%).

(2) To the suspension of tert-butyl 4-({2-[(3,5-dimethylphenyl)amino]-5-nitrophenyl}sulfonyl)-1-piperazinecarboxylate (150 mg, 0.31 mmol) in $CH_2Cl_2$ (2 ml) was added 4N HCl solution in 1,4-dioxane (1 ml), the mixture was stirred for 2 hrs at room temperature. The mixture was filtered. The filtrate was evaporated, and 5 ml of diethyl ether was added to the residue. The precipitate was collected by filtration and dried to give N-(3,5-dimethylphenyl)$_4$-nitro-2-(1-piperazinylsulfonyl)aniline dihydrochloride (115 mg, 81.2%): mp 175-179° C.; $^1$H NMR (300 MHz, DMSO-$d_6$) δ 2.30 (6H, s), 3.18 (4H, t, J=5.3 Hz), 3.44 (4H, q, J=5.3 Hz), 6.97 (3H, s), 7.10 (1H, d, J=9.4 Hz), 8.25 (1H, q, J=9.4 Hz), 8.34 (1H, d, J=2.64 Hz), 8.47 (1H, s), 9.23 (2H, br); HPLC-MS (ESI): Calcd for $C_{18}H_{22}N_4O_4S$ [M+H]$^+$ 391, Found: 391.

Molecular weight: 463.3864

Activity grade RBA: A

In the similar manner as described in Example 3-1 above, compounds in Example 3-2 to 3-12 as shown in Table 3 were synthesized.

TABLE 3

| EX.No. | molstructure | MW | M + 1 | mp | RBA | Ca2+ |
|---|---|---|---|---|---|---|
| 3-2 | | 467.76129 | 431 | 160 | A | A |
| 3-3 | | 412.89832 | 377 | 155 | B | B |
| 3-4 | | 412.89832 | 377 | 158 | B | B |
| 3-5 | | 412.89832 | 377 | 239-240 | C | B |

TABLE 3-continued
| EX.No. | molstructure | MW | M + 1 | mp | RBA | Ca2+ |
|---|---|---|---|---|---|---|
| 3-6 | 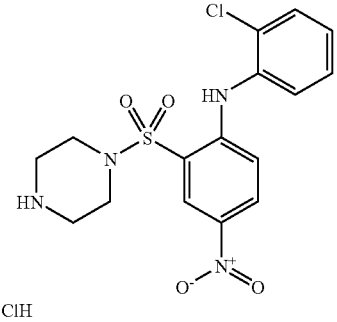 ClH | 433.31626 | 397 | | C | B |
| 3-7 | 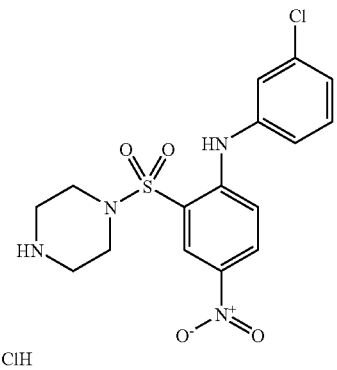 ClH | 433.31626 | 397 | 150 | A | |
| 3-8 | 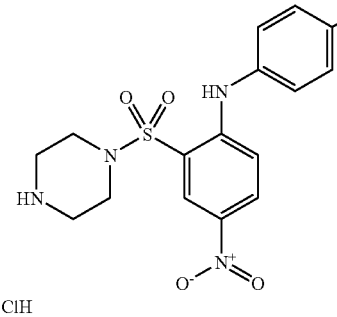 ClH | 433.31626 | 397 | 267 | A | |
| 3-9 | 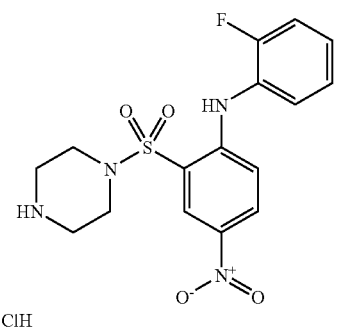 ClH | 416.86166 | 381 | 275 | A | |

TABLE 3-continued
| EX.No. | molstructure | MW | M + 1 | mp | RBA | Ca2+ |
|---|---|---|---|---|---|---|
| 3-10 | | 416.86166 | 381 | | | A |
| 3-11 | | 416.86166 | 381 | | | A |
| 3-12 | | 428.89772 | 393 | 241-242 | | A |
Example 4-1
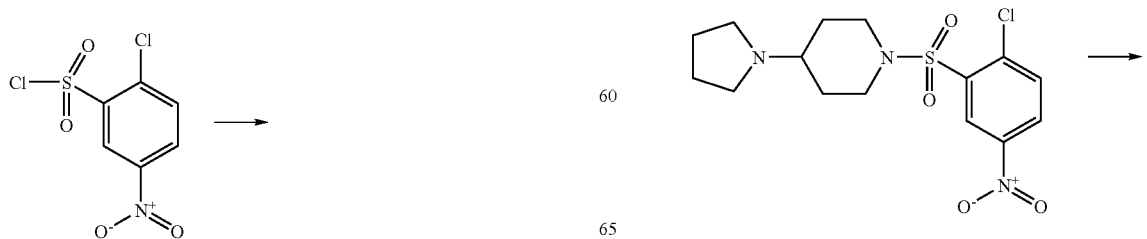

-continued

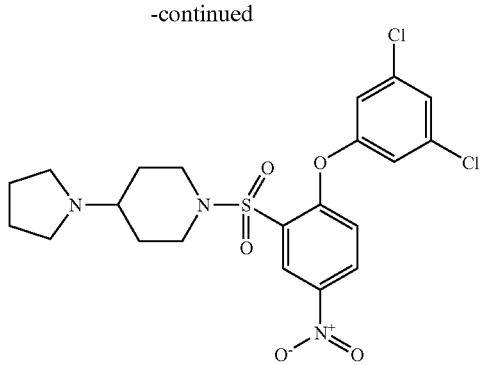

(1) To the solution of 2-chloro-5-nitrobenzenesulfonyl chloride (2.05 g, 8 mmol) in THF (60 ml) was added the solution of 4-(1-pyrrolidinyl)piperidine (1.23 g, 8 mmol) and NEt$_3$ (0.89 g, 8.8 mmol) in THF (15 ml) dropwise. The mixture was stirred at room temperature for 2 hrs. 3,5-Dichlorophenol (1.96 g, 12 mmol) was added to the above mixture followed by NaH (60%, 0.96 g, 12 mmol). The resulting mixture was stirred at 65° C. for 8 hrs, and cooled to room temperature. The precipitate was collected by filtration and washed with THF, Et$_2$O, and water, successively, dried in vacuo to give 1-{[2-(3,5-dichlorophenoxy)-5-nitrophenyl]sulfonyl}-4-(1-pyrrolidinyl)piperidine as white powder (3.2 g, 79.9%): mp 217-218° C.; $^1$H NMR (500 MHz, CDCl3) δ 1.26 (2H, s), 1.63 (4H, d, J=10 Hz), 1.77 (4H, s), 1.92 (2H, d, J=6.1 Hz), 2.15 (1H, m), 2.34 (6H, s), 2.97 (2H, p, J=10 Hz), 3.86 (2H, q, J=9.3 Hz), 6.74 (2H, s), 6.90 (1H, d, J=9.1 Hz), 6.94 (1H, s), 8.24 (1H, q, J=9.1 Hz), 8.86 (1H, d, J=2.85 Hz): HPLC-MS (ESI): Calcd for C$_{21}$H$_{23}$Cl$_2$N$_3$O$_5$S [M+H]$^+$ 501, Found: 500 and 502

Molecular weight: 500.4046

IC$_{50}$ (CCR3): 8 μM

IC$_{50}$ (Ca$^{2+}$): 7 μM

IC$_{50}$ (Chemotaxis): 5 μM

In the similar manner as described in Example 4-1 above, compounds in Example 4-2 to 4-41 as shown in Table 4 were synthesized.

TABLE 4

| EX.No. | molstructure | MW | M + 1 | mp | RBA | Ca2+ |
|---|---|---|---|---|---|---|
| 4-2 | | 433.53044 | 434 | | A | A |
| 4-3 | | 435.50275 | 436 | | B | A |
| 4-4 | | 405.47626 | 406 | 131-132 | A | A |

TABLE 4-continued

| EX.No. | molstructure | MW | M + 1 | mp | RBA | Ca2+ |
|---|---|---|---|---|---|---|
| 4-5 | | 419.50335 | 420 | 111-112 | A | A |
| 4-6 | | 473.59577 | 474 | 190-192 | A | A |
| 4-7 | | 467.54795 | 468 | 168-169 | C | C |
| 4-8 | | 481.57504 | 482 | 168-170 | C | C |

TABLE 4-continued

| EX.No. | molstructure | MW | M + 1 | mp | RBA | Ca2+ |
|---|---|---|---|---|---|---|
| 4-9 | | 481.57504 | 482 | 123-124 | C | |
| 4-10 | | 419.45972 | 437 | 210-212 | C | |
| 4-11 | | 459.56868 | 460 | 156-158 | A | |
| 4-12 | | 447.55753 | 448 | 86-88 | A | A |

TABLE 4-continued

| EX.No. | molstructure | MW | M + 1 | mp | RBA | Ca2+ |
|---|---|---|---|---|---|---|
| 4-13 | | 419.50335 | 420 | 115-116 | A | A |
| 4-14 | | 407.4922 | 408 | 75-77 | A | A |
| 4-15 | | 433.53044 | 434 | 129-131 | A | A |
| 4-16 | | 447.55753 | 448 | 134-135 | A | A |

TABLE 4-continued

| EX.No. | molstructure | MW | M + 1 | mp | RBA | Ca2+ |
|---|---|---|---|---|---|---|
| 4-17 | | 461.58462 | 462 | 93-95 | A | A |
| 4-18 | | 461.58462 | 462 | 131-132 | A | B |
| 4-19 | | 459.56868 | 460 | 169-171 | A | A |
| 4-20 | | 448.32808 | 448 | 105-107 | A | A |

TABLE 4-continued

| EX.No. | molstructure | MW | M + 1 | mp | RBA | Ca2+ |
|---|---|---|---|---|---|---|
| 4-21 | | 488.39341 | 488 | 120-121 | A | A |
| 4-22 | | 500.40456 | 500 | 200-202 | A | A |
| 4-23 | | 460.33923 | 460 | | A | A |
| 4-24 | | 469.99141 | 434 | 262-264 | A | A |

ClH

TABLE 4-continued

| EX.No. | molstructure | MW | M + 1 | mp | RBA | Ca2+ |
|---|---|---|---|---|---|---|
| 4-25 | | 482.34559 | 483 | 226 | B | |
| 4-26 | | 475.56808 | 476 | 178-179 | A | A |
| 4-27 | | 516.40396 | 517 | 182-183 | A | A |
| 4-28 | | 491.63268 | 492 | 143-144 | | A |

TABLE 4-continued

| EX.No. | molstructure | MW | M + 1 | mp | RBA | Ca2+ |
|---|---|---|---|---|---|---|
| 4-29 | | 514.43165 | 515 | 173-174 | A | A |
| 4-30 | | 531.46226 | 531 | 98-99 | | A |
| 4-31 | | 503.40808 | 503 | 138-140 | | A |
| 4-32 | | 529.44632 | 529 | 167-169 | | A |

TABLE 4-continued
| EX.No. | molstructure | MW | M + 1 | mp | RBA | Ca2+ |
|---|---|---|---|---|---|---|
| 4-33 | 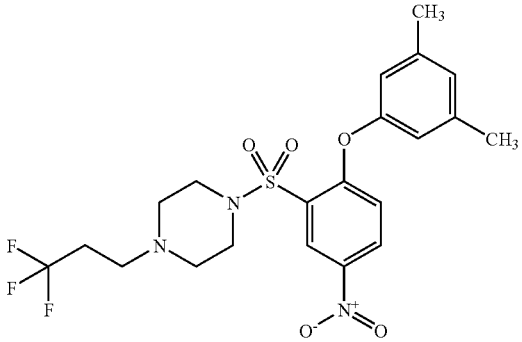 | 487.50173 | 488 | | A | A |
| 4-34 | 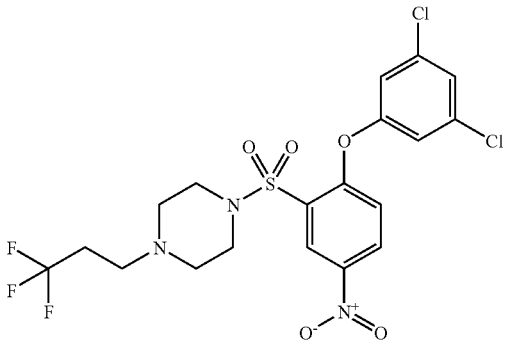 | 528.33761 | 528 | 166-167 | A | A |
| 4-35 | 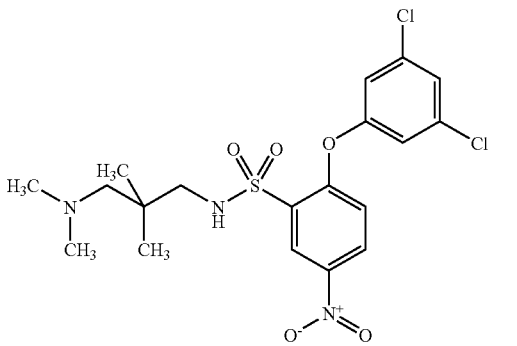 | 476.38226 | 476 | 134 | | A |
| 4-36 | 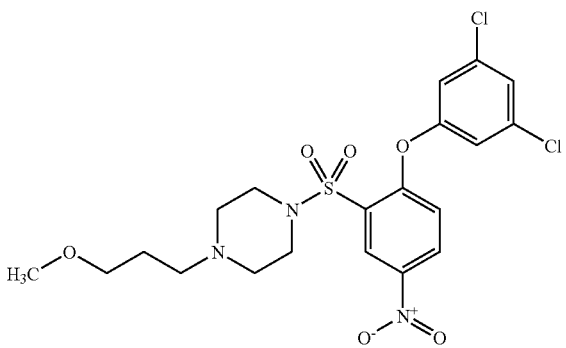 | 504.39281 | 504 | 145 | A | A |

TABLE 4-continued

| EX.No. | molstructure | MW | M + 1 | mp | RBA | Ca2+ |
|---|---|---|---|---|---|---|
| 4-37 | | 532.40336 | 532 | 160-162 | | A |
| 4-38 | | 486.37747 | 486 | | A | A |
| 4-39 | | 462.35517 | 462 | | | A |
| 4-40 | | 502.4205 | 502 | | | A |

TABLE 4-continued

| EX.No. | molstructure | MW | M + 1 | mp | RBA | Ca2+ |
|---|---|---|---|---|---|---|
| 4-41 | | 474.36632 | 474 | | | A |

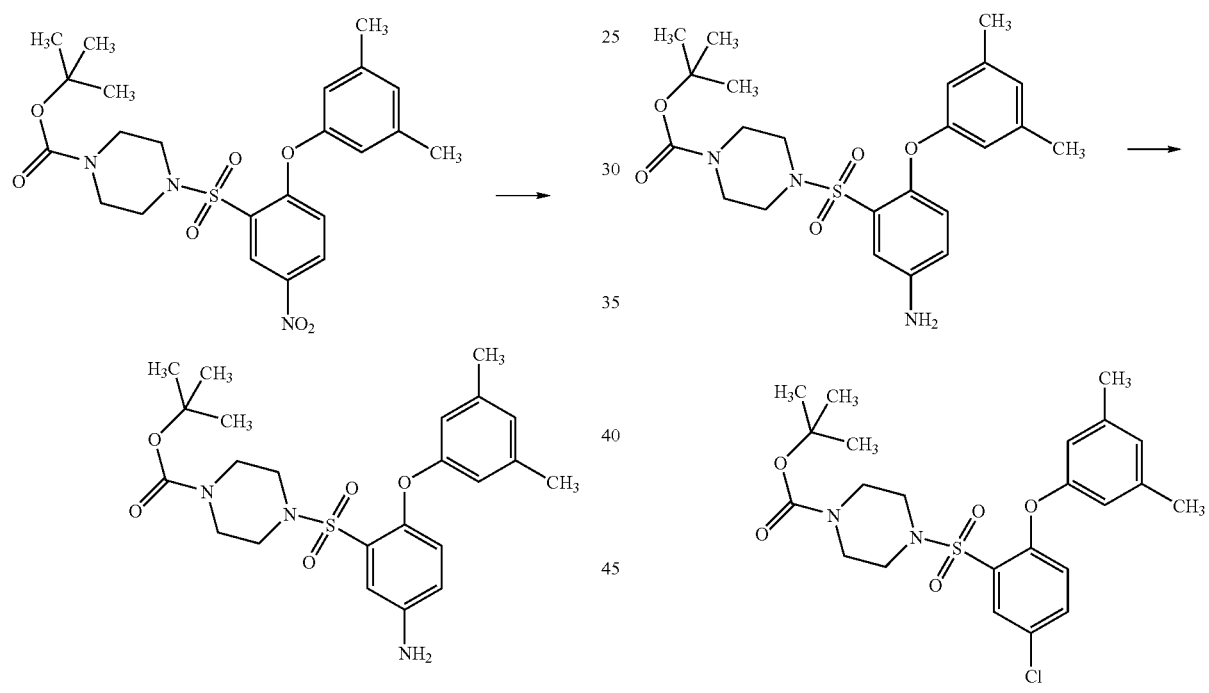

Example 5-1

Example 5-2

(1) The mixture of tert-butyl 4-{[2-(3,5-dimethylphenoxy)-5-nitrophenyl]-sulfonyl}-1-piperazinecarboxylate (6.80 g, 13.83 mmol), which was prepared in the step (2) of Example 1-1 and 10% Pd-C (1) in methanol (600 ml) was stirred at room temperature under 1 ATM of $H_2$ for 5 hrs. The Pa—C was filtered off. The filtrate was evaporated to 30 ml. The produced crystals was collected by filtration to give tert-butyl 4-{[5-amino-2-(3,5-dimethylphenoxy)phenyl]sulfonyl}-1-piperazinecarboxylate (6.0 g, 94.0%).: HPLC-MS (ESI): Calcd for $C_{23}H_{31}N_3O_5S$ $[M+H]^+$ 462, Found: 462.

Molecular weight: 461.5846
Activity grade RBA: C
Activity grade $Ca^{2+}$: C (1) To the mixture of copper(I) chloride (39.6 mg, 0.4 mmol) and tert-butyl nitrite (41.2 mg, 0.4 mmol) in $CH_3CN$ (10 ml) was added tert-butyl 4-{[5-amino-2-(3,5-dimethylphenoxy)phenyl]sulfonyl}-1-piperazinecarboxylate (92.3 mg, 0.2 mmol) which was prepared in the Example 5-1 at 60° C. The mixture was stirred at 65-70° C. for 2 hrs, and cooled to room temperature. The solvent was evaporated. $CH_2Cl_2$ was added to the residue and the mixture was washed with 15 ml of 4N NaOH, 30 ml of brine, successively, dried over $MgSO_4$. The solvent was evaporated, and the residue was purified by preparative TLC on silica gel ($CH_2Cl_2/CH_3OH=35/1$) to give tert-butyl-4-{[5-chloro-2-(3,5-dimethylphenoxy)phenyl]sulfonyl}-1-piperazinecarboxylate (56.0 mg, 58.2%).

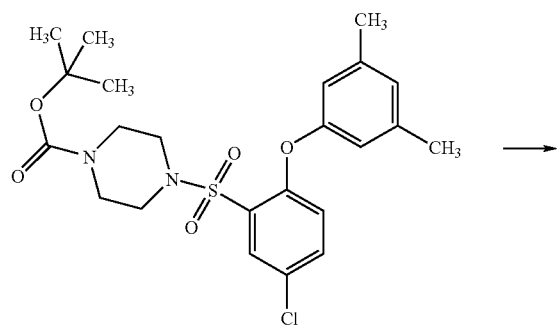

(2) To the suspension of tert-butyl 4-{[5-chloro-2-(3,5-dimethylphenoxy)phenyl]sulfonyl}-1-piperazinecarboxylate (40.0 mg, 0.08 mmol) in dry $CH_2Cl_2$ (1.5 ml) was added 0.3 ml of 4N hydrogen chloride solution in 1,4-dioxane, the mixture was stirred for 5 hrs at room temperature. The solvent was evaporated, and diethyl ether (5 ml) was added to the residue. The produced precipitate was collected by filtration and dried to give 1-{[5-chloro-2-(3,5-dimethylphenoxy)phenyl]sulfonyl}piperazine hydrochloride (24.0 mg, 69.2%): mp 202-204° C.; 1H NMR (300 MHz, DMSO-d6) δ 2.30 (6H, s), 3.14 (4H, be), 3.50 (4H, br), 6.82 (2H, s), 6.91 (1H, s), 6.97 (1H, d, J=8.7 Hz), 7.70 (1H, t, J=8.7 Hz), 7.82 (1H, d, J=2.3 Hz), 9.57 (2H, br); HPLC-MS (ESI): Calcd for $C_{18}H_{21}ClN_2O_3S$ $[M+H]^+$ 381, Found: 381.

Molecular weight: 417.3576

Activity grade RBA: A

Activity grade $Ca^{2+}$: A

In the similar manner as described in Example 5-1 or 5-2 above, compounds in Example 5-3 to 5-8 as shown in Table 5 were synthesized.

TABLE 5

| EX.No. | molstructure | MW | M + 1 | mp | RBA | Ca2+ |
|---|---|---|---|---|---|---|
| 5-3 | | 475.49058 | 362 | 133-135 | C | C |
| 5-4 | | 408.95085 | 409 | 120-122 | A | A |

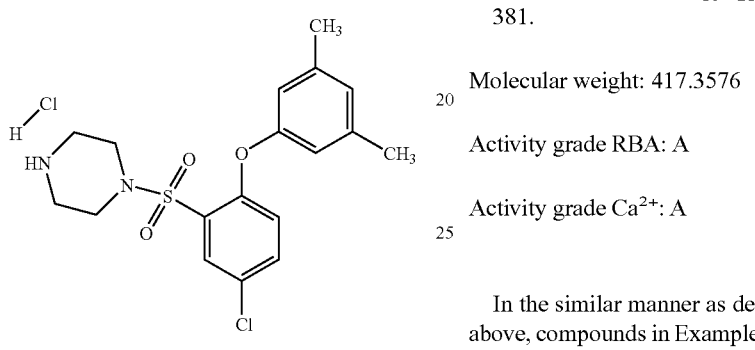

TABLE 5-continued

| EX.No. | molstructure | MW | M + 1 | mp | RBA | Ca2+ |
|---|---|---|---|---|---|---|
| 5-5 | | 500.40225 | 501 | 133-134 | A | A |
| 5-6 | | 508.80904 | 473 | 241-243 | A | A |
| 5-7 | | 448.41534 | 376 | 183 | C | C |
| 5-8 | | 431.38473 | 395 | 148 | A | |

Example 6-1

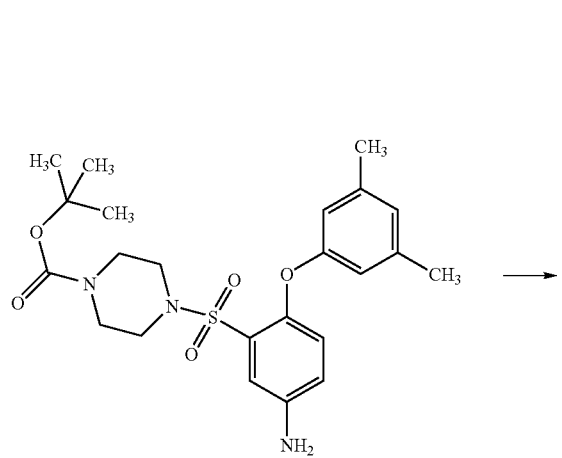

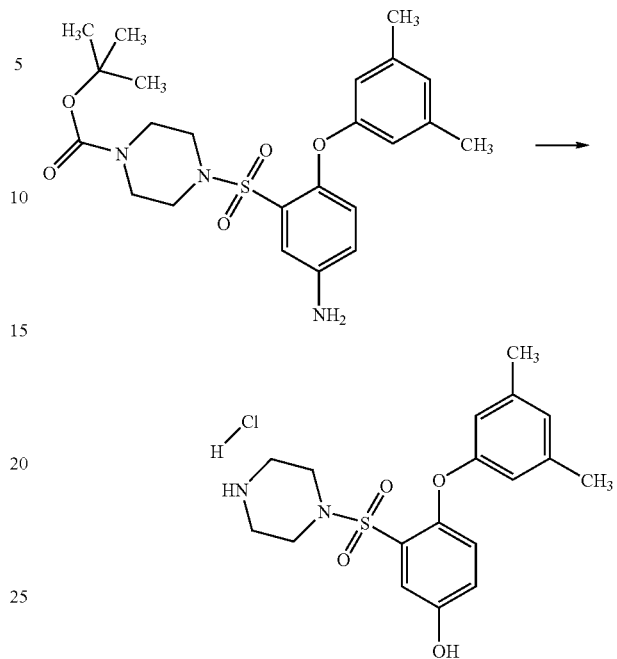

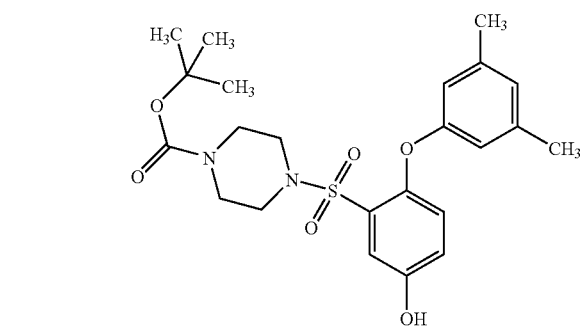

(1) To the solution of tert-butyl 4-{[5-amino-2-(3,5-dimethylphenoxy)phenyl]-sulfonyl}-1-piperazinecarboxylate (138.5 mg, 0.30 mmol) prepared in the step (1) of Example 5-1 in CH$_2$Cl$_2$ (5 ml) was added nitrosonium tetrafluoroborate (38.5 mg, 0.33 mmol) at 0° C. and the solution was stirred at 0° C. for 30 min. The solvent was evaporated. The residue was dissolved in methanol (5 ml) and the solution of Cu$_2$O (64.4 mg, 0.45 mmol) and CuSO$_4$.3H$_2$O (724.8 mg, 3 mmol) in 10 ml of water was added to the above solution at 0° C. The mixture was stirred at 0° C. for 30 min. The solvent was evaporated and ethyl acetate was added. The mixture was washed with 1 N aqueous NaOH, brine, successively and dried over MgSO$_4$. The solvent was evaporated and the residue was purified by preparative TLC on silica gel (CH$_2$Cl$_2$/CH$_3$OH=20/1) to give tert-butyl 4-{[2-(3,5-dimethylphenoxy)-5-hydroxyphenyl]-sulfonyl}-1-piperazinecarboxylate (39.0 mg, 28.1%).

(2) To the suspension of tert-butyl 4-{[2-(3,5-dimethylphenoxy)-5-hydroxyphenyl]sulfonyl}-1-piperazinecarboxylate (12.0 mg, 0.03 mmol) in dry CH$_2$Cl$_2$ (1 ml) was added 4 N HCl solution in 1,4-dioxane (0.18 ml), the mixture was stirred 5 hrs at room temperature. The solvent was evaporated, and 3 ml of diethyl ether was added to the residue. The precipitate was collected by filtration and dried to give 4-(3,5-dimethylphenoxy)-3-(1-piperazinylsulfonyl)phenol hydrochloride (9.0 mg, 87.0%): mp >286; 1H NMR (300 MHz, DMSO-d6) δ 2.24 (6H, s), 3.12 (4H, br), 3.36 (4H, br), 6.56 (2H, s), 6.76 (1H, s), 6.96 (1H, d, J=9 Hz), 7.08 (1H, q, J=9 Hz), 7.25 (1H, d, J=2.6 Hz), 9.03 (2H, br), 10.06 (1H, s); HPLC-MS (ESI): Calcd for C$_{18}$H$_{22}$N$_2$O$_4$S [M+H]$^+$ 363, Found: 363.

Molecular weight: 398.9120

Activity grade RBA: C

Activity grade Ca$^{2+}$: C

Example 6-2

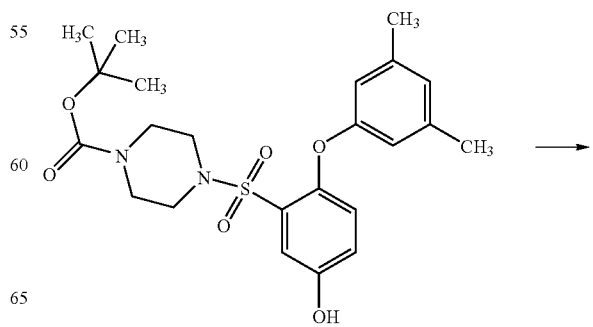

-continued

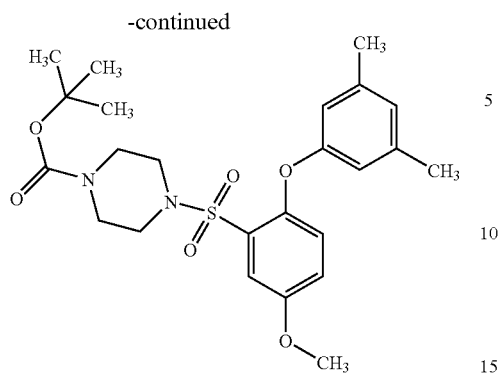

(1) To the solution of tert-butyl 4-{[2-(3,5-dimethylphenoxy)-5-hydroxyphenyl]-sulfonyl}-1-piperazinecarboxylate (20.0 mg, 0.04 mmol), which was prepared in the step (1) of Example 6-1 in dry DMF (1 ml) was added methyl iodide (30.7 mg, 0.22 mmol) and K$_2$CO$_3$ (12.0 mg, 0.09 mmol). The mixture was stirred at room temperature for 3 hrs. The solvent was evaporated in vacuo and 3 ml of ice water was added. The white precipitate was collected by filtration and washed with 1 N aqueous NaOH, water and dried to give tert-butyl 4-{[2-(3,5-dimethylphenoxy)-5-methoxyphenyl]sulfonyl}-1-piperazinecarboxylate as white powder (20.0 mg, 97.1%).

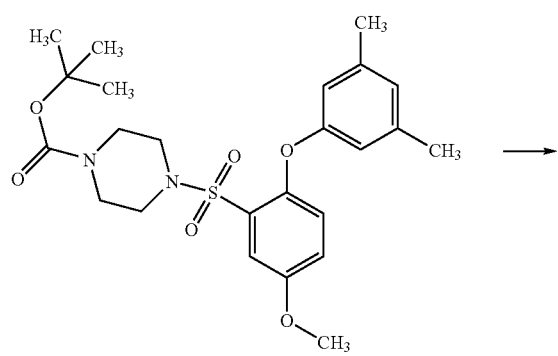

-continued

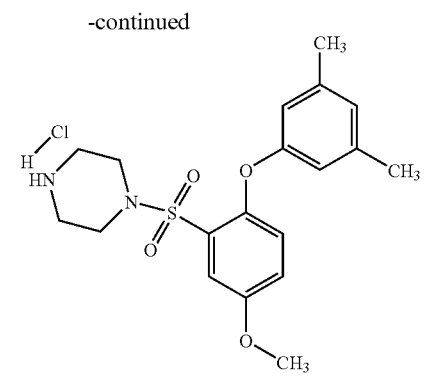

(2) To the solution of tert-butyl 4-{[2-(3,5-dimethylphenoxy)-5-methoxyphenyl]-sulfonyl}-1-piperazinecarboxylate (18.0 mg, 0.04 mmol) in dry CH$_2$Cl$_2$ (1 ml) was added 4 N HCl (0.2 ml) solution in 1,4-dioxane, the mixture was stirred hrs at room temperature. The solvent was evaporated, and 3 ml of diethyl ether was added to the residue. The precipitate was collected by filtration and dried to give 4-(3,5-dimethylphenoxy)-3-(1-piperazinylsulfonyl)phenol hydrochloride (12.0 mg, 76.9%): mp 175-177° C.; 1H NMR (300 MHz, DMSO-d6) δ 2.25 (6H, s), 3.12 (4H, t, J=4.5 Hz), 3.40 (4H, d, J=4.5 Hz), 3.82 (3H, s), 6.62 (2H, s), 6.80 (1H, s), 7.04 (1H, d, J=9.1 Hz), 7.27 (1H, q, J=9.1 Hz), 7.33 (1H, d, J=3.0 Hz), 9.24 (2H, br); HPLC-MS (ES): Calcd for C$_{19}$H$_{24}$N$_2$O$_4$S [M+H]$^+$ 377, Found: 377.

Molecular weight: 412.9391

Activity grade RBA: A

Activity grade Ca$^{2+}$: B

In the similar manner as described in Example 6-1 or 6-2 above, compounds in Example 6-3, 6-4 and 6-5 as shown in Table 6 were synthesized.

TABLE 6

| EX.No. | molstructure | MW | M + 1 | mp | RBA | Ca2+ |
|---|---|---|---|---|---|---|
| 6-3 | | 364.4421 | 365 | 116-118 | A | A |

TABLE 6-continued

| EX.No. | molstructure | MW | M + 1 | mp | RBA | Ca2+ |
|---|---|---|---|---|---|---|
| 6-4 | | 412.2974 | 412 | 179-181 | 9 | 7 |
| 6-5 | | 480.4169 | 480 | 186-187 | 20 | 17 |

Example 7-1

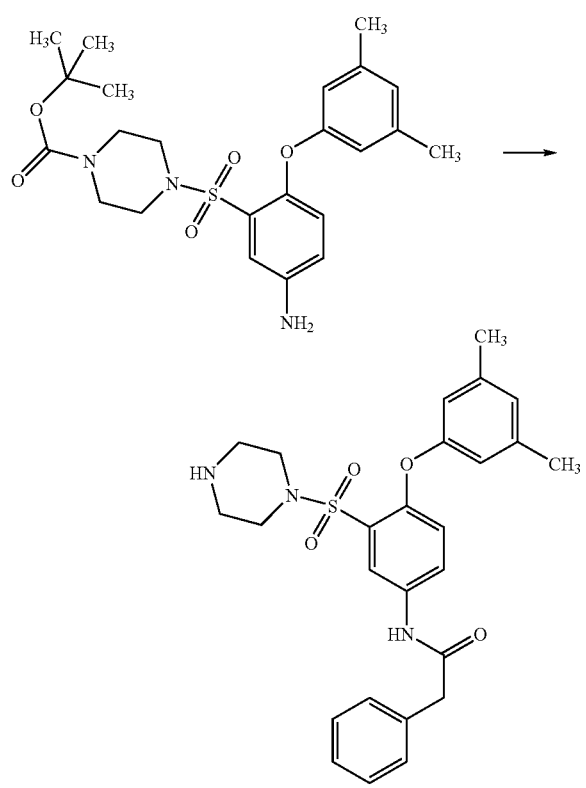

(1) To the mixture of tert-butyl 4-{[5-amino-2-(3,5-dimethylphenoxy)phenyl]-sulfonyl}-1-piperazinecarboxylate (369 mg, 0.80 mmol), which was prepared in the step (1) of Example 5-1, and triethylamine (97 mg, 0.96 mmol) in dry $CH_2Cl_2$ (20 ml) was added dropwise the solution of phenylacetyl chloride (130 mg, 0.84 mmol) in THF (5 ml) at 0° C. with stirring. The mixture was then stirred at RT for 3 hrs, and $CH_2Cl_2$ was added. The mixture was washed with 0.5 N aqueous HCl, brine, saturated aqueous $NaHCO_3$, brine, successively, dried over $MgSO_4$. The solvent was evaporated. Dry $CH_2Cl_2$ (15 ml) was added to the residue. 4 N HCl solution in 2,4-dioxane (1 ml) was added to the solution at 0° C. with stirring. The mixture was then stirred at room temperature for 3 hrs. The obtained precipitate was collected to give product as HCl salt. The HCl salt was suspended in 10 ml of ice water and the PH of the mixture was adjusted to 8 by addition of saturated aqueous $NaHCO_3$, extracted by $CH_2Cl_2$. The combined extract was washed with saturated aqueous $NaHCO_3$, brine, successively, dried over $MgSO_4$. The solvent was evaporated. 5 ml of methanol was added to the residue and the white precipitate was collected by filtration and washed with ether and dried to give N-[4-(3,5-dimethylphenoxy)-3-(1-piperazinylsulfonyl)phenyl]-2-phenylacetamide (330 mg, 86.0%): mp 228-230° C.; 1H NMR (300 MHz, CDCl3). 2.28 (6H, s), 2.87 (4H, br), 3.24 (4H, br), 3.74 (2H, s), 6.62 (2H, s), 6.79 (1H, s), 6.87 (1H, d, J=8.8 Hz), 7.34-7.62 (6H, m), 7.62 (1H, s), 7.95 (1H, q, J=8.8 Hz); HPLC-MS (ESI): Calcd for $C_{26}H_{29}N_3O_4S$ [M+H]$^+$ 480, Found: 480.

Molecular weight: 479.6027
Activity grade RBA: C
Activity grade $Ca^{2+}$: C

In the similar manner as described in Example 7-1 above, compounds in Example 7-2 to 7-9 as shown in Table 7 were synthesized.

TABLE 7

| EX.No. | molstructure | MW | M + 1 | mp | RBA | Ca2+ |
|---|---|---|---|---|---|---|
| 7-2 | | 403.504 | 404 | | C | C |
| 7-3 | | 445.5852 | 446 | | C | C |
| 7-4 | | 445.5852 | 446 | | C | C |
| 7-5 | | 502.0366 | 466 | | C | C |

TABLE 7-continued
| EX.No. | molstructure | MW | M + 1 | mp | RBA | Ca2+ |
|---|---|---|---|---|---|---|
| 7-6 | 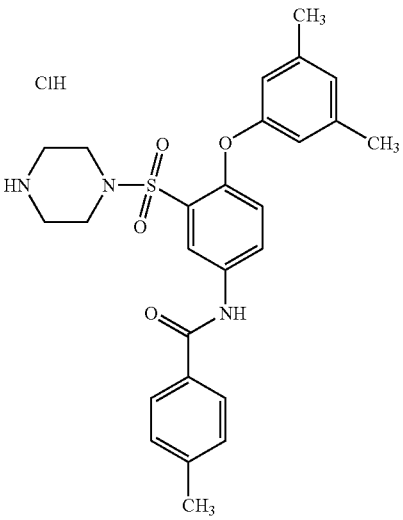 | 516.0637 | 484 | | C | C |
| 7-7 | 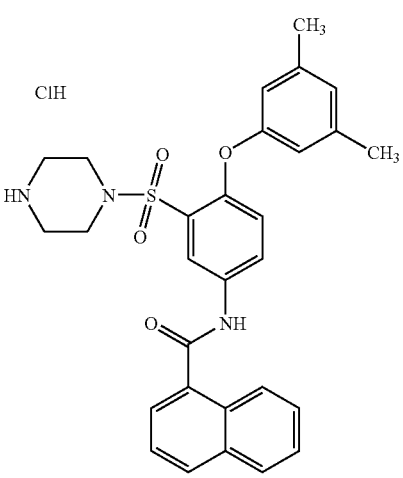 | 552.0972 | 516 | | C | B |
| 7-8 | 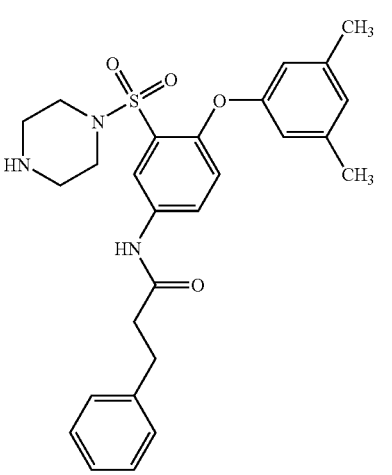 | 493.6298 | 494 | | C | C |

TABLE 7-continued

| EX.No. | molstructure | MW | M + 1 | mp | RBA | Ca2+ |
|---|---|---|---|---|---|---|
| 7-9 | | 471.6014 | 472 | | C | C |

Example 8-1

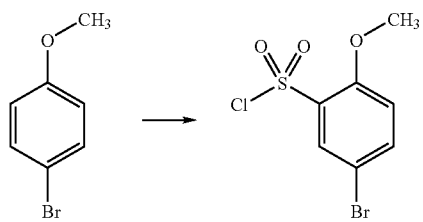

(1) To a solution of 4-bromoanisole (2.00 g, 10.7 mmol) in CHCl$_3$ (20 ml) was added chlorosulfonic acid (1.49 ml, 22.5 mmol) at 0° C. This mixture was stirred at room temperature for 2 hrs, and then poured into ice water (50 ml). This mixture was extracted with CH$_2$Cl$_2$. The combined organic extracts were washed with brine, dried over anhydrous MgSO$_4$, filtered, and concentrated to give crude 5-bromo-2-methoxybenzenesulfonyl chloride (0.760 g, 24.9%).

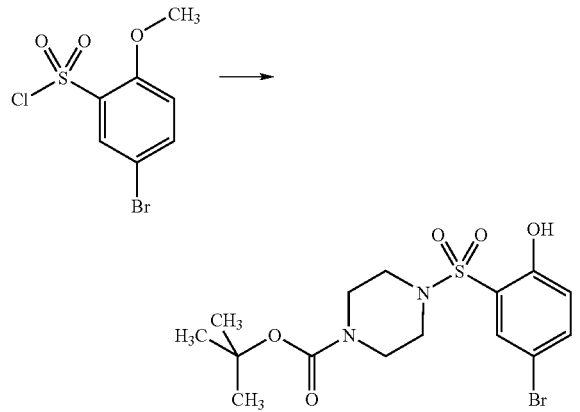

(2) To a solution of 5-bromo-2-methoxybenzenesulfonyl chloride (760 mg, 2.66 mmol) and Et$_3$N (445 µl, 3.19 mmol) in CH$_2$Cl$_2$ (20 ml) was added 1-(t-butoxycarbonyl)piperazine (521 mg, 2.80 mmol) at 0° C. This mixture was stirred at room temperature for 6 hrs, and then diluted with Et$_2$O, washed with 10% citric acid solution, aqueous NaHCO$_3$, and brine. The organic layer was dried over anhydrous Na$_2$SO$_4$, filtered, and concentrated to give crude sulfonamide (716 mg).

To a solution of the sulfonamide (716 mg, 1.65 mmol) in CH$_2$Cl$_2$ (5 ml) was added 1M BBr$_3$ solution in CH$_2$Cl$_2$ (3.30 ml, 3.30 mmol) at 0° C. This mixture was stirred at 0° C. for 1 hr. After basifing with 3M aqueous NaOH (20 ml), THF (15 ml) and Di-t-butyl dicabonate (718 mg, 3.29 mmol) were added to the mixture at 0° C. The mixture was stirred at room temperature overnight. This mixture was extracted with Et$_2$O. The organic extract was dried over anhydrous Na$_2$SO$_4$, filtered, and concentrated to give di(Boc)-compound. To hydrolize t-butyl carbonate, the residue was treated with K$_2$CO$_3$ (455 mg, 3.29 mmol) in MeOH (10 ml) at room temperature for 5 hrs. After removing MeOH by evaporation, the residue was acidified with 10% citric acid solution. This aqueous mixture was extracted with EtoAc. The organic extract was dried over anhydrous Na$_2$SO$_4$, filtered, and concentrated to give tert-butyl 4-[(5-bromo-2-hydroxyphenyl)sulfonyl]-1-piperazinecarboxylate (526 mg, 47.0%).

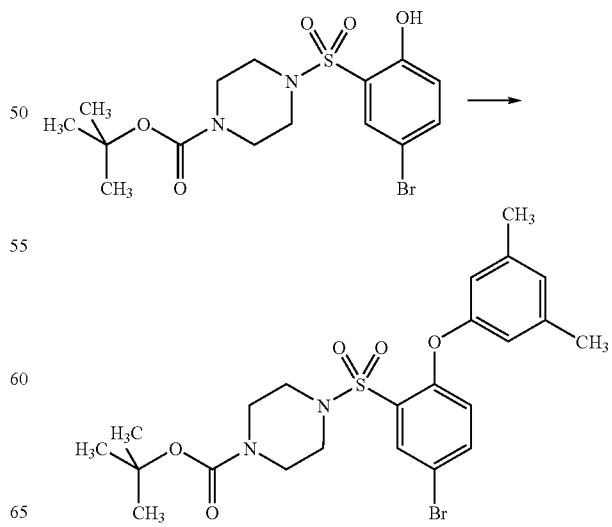

(3) To a mixture of tert-butyl 4-[(5-bromo-2-hydroxyphenyl)sulfonyl]-1-piperazinecarboxylate (410 mg, 0.973 mmol), 3,5-dimethylphenylbronic acid (219 mg, 1.46 mmol), Cu(OAc)$_2$ (177 mg, 0.973 mmol), and powdered 4A molecular sieves (820 mg) in CH$_2$Cl$_2$ (10 ml) was added Et$_3$N (0.678 ml, 4.87 mmol) at room temperature. This mixture was stirred at room temperature under ambient atmosphere overnight. The resulting slurry was filtered through Celite. The filtrate was diluted with EtoAc, and washed with aqueous NH$_4$Cl, NaHCO$_3$, and brine. The organic layer was dried over anhydrous Na$_2$SO$_4$, filtered, and concentrated. Et$_2$O was added to the residue. The resulting precipitate was collected by filtration, and washed with Et$_2$O. This solid was purified by column chromatography on silica gel (CHCl$_3$/MeOH=99/1) to give tert-butyl 4-{[5-bromo-2-(3,5-dimethylphenoxy)phenyl]sulfonyl}-1-piperazinecarboxylate (320 mg, 62.6%).

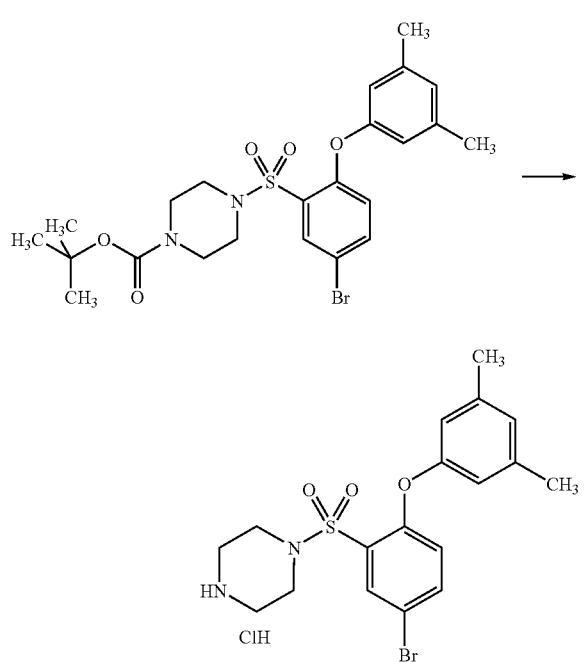

(4) To a solution of tert-butyl 4-{[5-bromo-2-(3,5-dimethylphenoxy)phenyl]-sulfonyl}-1-piperazinecarboxylate (25.0 mg, 48.0 μmol) in CH$_2$Cl$_2$ (1.0 ml) was added 4M HCl solution in 1,4-dioxane (100 μl, 400 μmol) at 0° C. This mixture was stirred at room temperature overnight. Solvents were removed by evaporation. The resulting residue was suspended in Et$_2$O, and collected by filtration to give a white amorphous, 1-{[5-bromo-2-(3,5-dimethylphenoxy)phenyl]sulfonyl}piperazine hydrochloride (20.0 mg, 90.2%): $^1$H NMR (300 MHz, CDCl$_3$) δ 2.31 (6H, s), 3.12-3.38 (4H, br), 3.60-3.84 (4H, br), 6.72 (2H, s), 6.75 (1H, d, J=8.7 Hz), 6.87 (1H, s), 7.54 (1H, dd, J=2.3, 8.7 Hz), 8.05 (1H, d, J=2.3 Hz), 9.79-10.40 (2H, br); HPLC-MS (ESI): Calcd for C$_{18}$H$_{21}$BrN$_2$O$_3$S [M+H]$^+$ 425 and 427, Found: 425 and 427.

Molecular weight: 461.8086

Activity grade RBA: A

Activity grade Ca$^{2+}$: A

Example 9-1

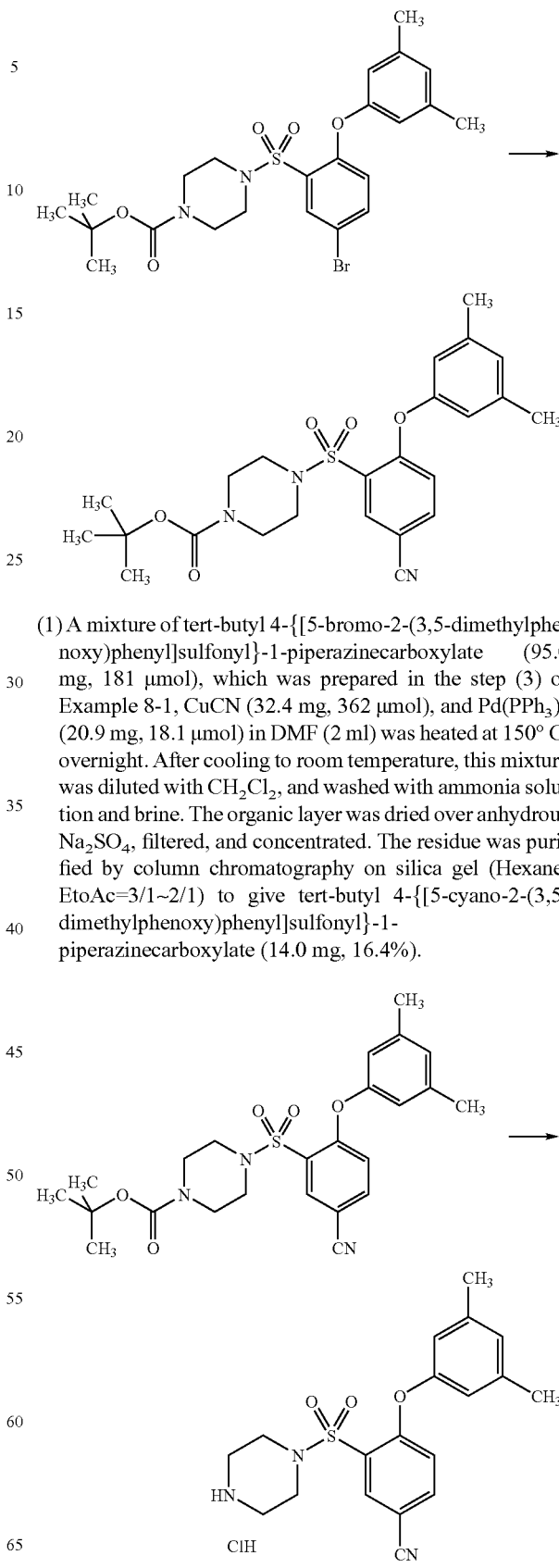

(1) A mixture of tert-butyl 4-{[5-bromo-2-(3,5-dimethylphenoxy)phenyl]sulfonyl}-1-piperazinecarboxylate (95.0 mg, 181 μmol), which was prepared in the step (3) of Example 8-1, CuCN (32.4 mg, 362 μmol), and Pd(PPh$_3$)$_4$ (20.9 mg, 18.1 μmol) in DMF (2 ml) was heated at 150° C. overnight. After cooling to room temperature, this mixture was diluted with CH$_2$Cl$_2$, and washed with ammonia solution and brine. The organic layer was dried over anhydrous Na$_2$SO$_4$, filtered, and concentrated. The residue was purified by column chromatography on silica gel (Hexane/EtoAc=3/1~2/1) to give tert-butyl 4-{[5-cyano-2-(3,5-dimethylphenoxy)phenyl]sulfonyl}-1-piperazinecarboxylate (14.0 mg, 16.4%).

(2) To a solution of tert-butyl 4-{[5-cyano-2-(3,5-dimethylphenoxy)phenyl]-sulfonyl}-1-piperazinecarboxylate (14.0 mg, 29.7 μmol) in CH$_2$Cl$_2$ (1.0 ml) was added 4M HCl solution in dioxane (0.2 ml) at room temperature. This mixture was stirred at room temperature overnight. Dioxane was removed by evaporation. The residue was suspended in Et$_2$O. The resulting precipitate was collected by filtration to give 4-(3,5-dimethylphenoxy)-3-(1-piperazinylsulfonyl)benzonitrile hydrochloride (6.0 mg, 49.6%): $^1$H NMR (300 MHz, CDCl$_3$) δ 2.34 (6H, s), 3.28-3.47 (4H, br), 3.67-3.83 (4H, br), 6.78 (2H, s), 6.89 (1H, d, J=8.6 Hz), 6.95 (1H, s), 7.69 (1H, dd, J=1.9, 8.6 Hz), 8.24 (1H, d, J=1.9 Hz), 9.97-10.32 (2H, br); HPLC-MS (ESI): Calcd for C$_{19}$H$_{21}$N$_3$O$_3$S [M+H]$^+$ 372, Found: 372.

Molecular weight: 407.9225
Activity grade RBA: A
Activity grade Ca$^{2+}$: A

Example 10-1

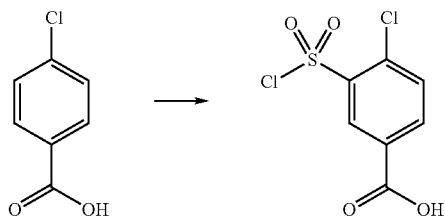

(1) To 4-chlorobenzoic acid (1.00 g, 6.39 mmol) was added chlorosulfonic acid (2.55 ml, 38.3 mmol) at room temperature dropwise. This mixture was heated at 150° C. for 6 hrs. After cooling to room temperature, the mixture was diluted with CH$_2$Cl$_2$. This solution was added to ice water. Two phases were separated. The organic phase was washed with brine, and then dried over anhydrous MgSO$_4$, filtered, and concentrated to give crude 4-chloro-3-(chlorosulfonyl)benzoic acid (0.720 g, 43.9%).

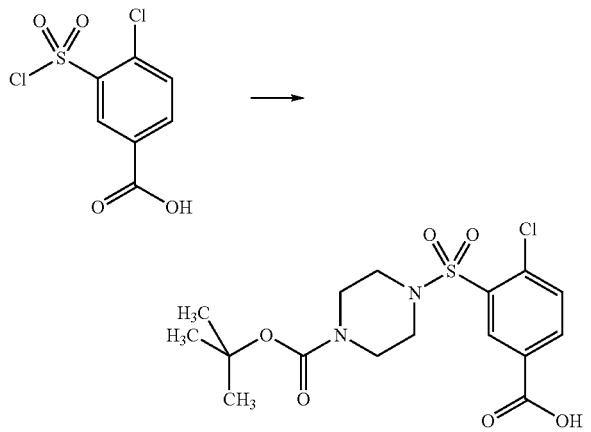

(2) To a solution of 4-chloro-3-(chlorosulfonyl)benzoic acid (200 mg, 0.784 mmol) and Et$_3$N (130 μl, 0.938 mmol) in CH$_2$Cl$_2$ (5 ml) was added 1-(t-butoxycarbonyl)piperazine (161 mg, 0.864 mmol) at 0° C. This mixture was stirred at room temperature overnight, and then diluted with CH$_2$Cl$_2$, washed with 10% citric acid solution. The organic layer was dried over anhydrous Na$_2$SO$_4$, filtered, and concentrated. The residue was suspended in Et$_2$O, and the precipitate was collected by filtration to give crude 3-{[4-(tert-butoxycarbonyl)-1-piperazinyl]sulfonyl}-4-chlorobenzoic acid (200 mg, 63.0%).

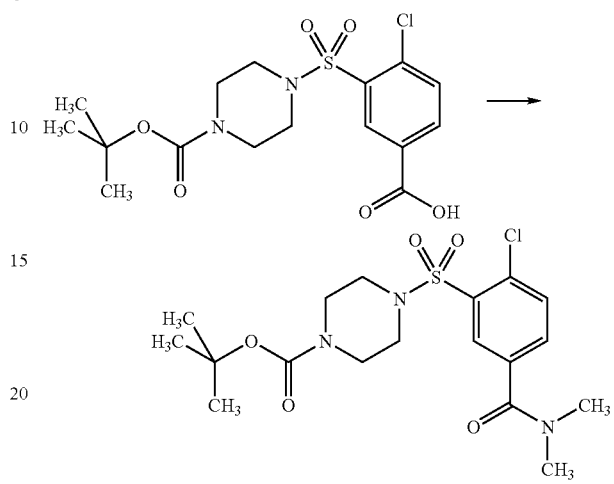

(3) To a mixture of 3-{[4-(tert-butoxycarbonyl)-1-piperazinyl]sulfonyl}-4-chlorobenzoic acid (340 mg, 0.840 mmol), dimethylammonium chloride (137 mg, 1.68 mmol), 1-(3-dimethylaminopropyl)-3-ethylcarbodiimide hydrochloride (193 mg, 1.01 mmol), and HOBT (136 mg, 1.01 mmol) in CH$_2$Cl$_2$ was added Et$_3$N (410 μl, 2.96 mmol) at 0° C. This mixture was stirred at room temperature for two days. The mixture was diluted with EtoAc, and washed with 10% citric acid solution, aqueous NaHCO$_3$, and brine. The organic layer was dried over anhydrous Na$_2$SO$_4$, filtered, and concentrated. The residue was purified by column chromatography on silica gel (EtoAc) to give tert-butyl 4-({2-chloro-5-[(dimethylamino)carbonyl]phenyl}sulfonyl)-1-piperazinecarboxylate (258 mg, 71.1%).

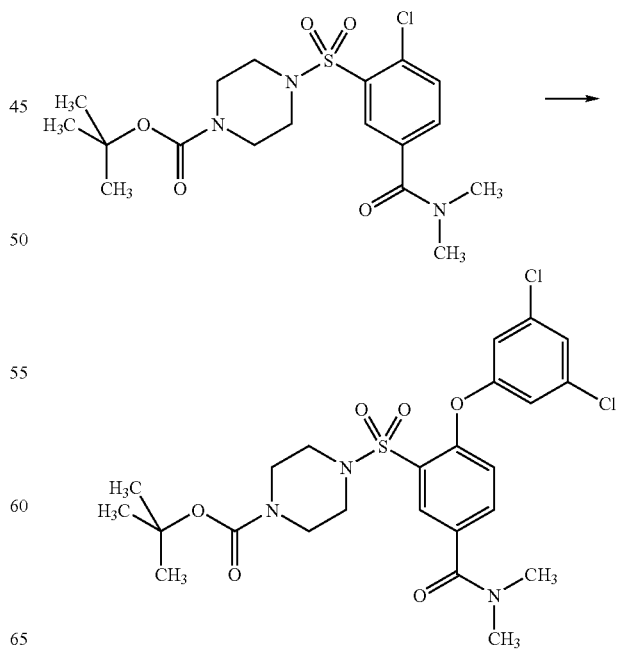

(4) To a mixture of tert-butyl 4-({2-chloro-5-[(dimethylamino)carbonyl]phenyl}sulfonyl)-1-piperazinecarboxylate (248 mg, 0.574 mmol) and 3,5-dimethylphenol (140 mg, 0.859 mmol) in DMF (2 ml) was added t-BuOK (129 mg, 1.15 mmol) at room temperature. This mixture was heated at 150° C. for two days. After cooling to room temperature, ice water (10 ml) was added to the mixture. Two phases were separated. The aqueous phase was extracted with $CH_2Cl_2$. The combined organic layers were washed with aqueous $NaHCO_3$ and brine, dried over anhydrous $Na_2SO_4$, filtered, and concentrated. This residue was purified by column chromatography on silica gel (Hexane/EtoAc=1/2) to give tert-butyl 4-({2-(3,5-dichlorophenoxy)-5-[(dimethylamino)-carbonyl]phenyl}sulfonyl)-1-piperazinecarboxylate (182 mg, 56.8%).

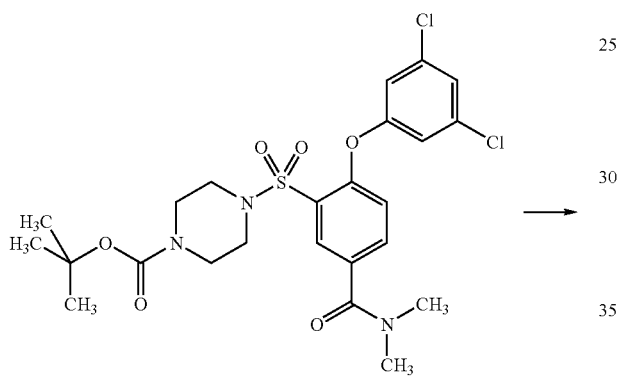

→

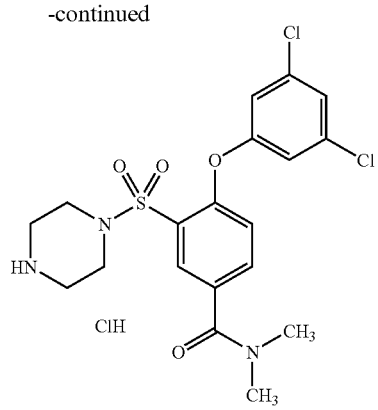

(5) To a solution of tert-butyl 4-({2-(3,5-dichlorophenoxy)-5-[(dimethylamino)carbonyl]phenyl}sulfonyl)-1-piperazinecarboxylate (150 mg, 0.269 mmol) in $CH_2Cl_2$ was added 4M HCl solution in dioxane (0.300 ml, 1.20 mmol) at 0° C. This mixture was stirred at room temperature overnight. Solvents were removed by evaporation. The resulting residue was suspended in $Et_2O$ and collected by filtration to give 4-(3,5-dichlorophenoxy)-N,N-dimethyl-3-(1-piperazinylsulfonyl)benzamide hydrochloride (50.0 mg, 37.6%): mp 197-199° C.; HPLC-MS (ESI): Calcd for $C_{19}H_{21}Cl_2N_3O_4S$ $[M+H]^+$ 458, Found: 458.
Molecular weight: 494.8279
Activity grade RBA: B
Activity grade $Ca^{2+}$: B In the similar manner as described in Example 10-1 above, compound in Example 10-2 as shown in Table 10 was synthesized.

TABLE 10

| EX.No. | molstructure | MW | M + 1 | mp | RBA | Ca2+ |
|---|---|---|---|---|---|---|
| 10-2 | | 490.0443 | 454 | 242-247 | B | A |

Example 11-1

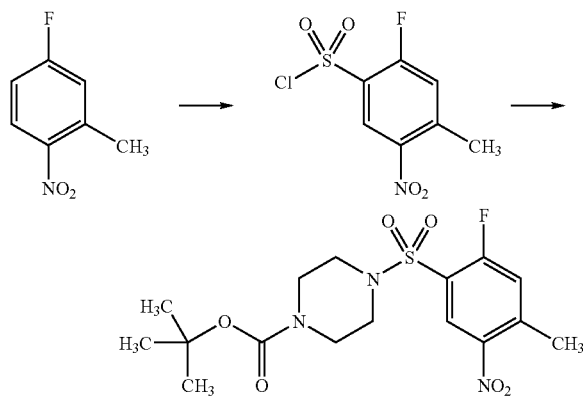

(1) To a mixture of 5-fluoro-2-nitrotoluene (1.00 g, 6.45 mmol) in $CHCl_3$ (10 ml) was added chlorosulfonic acid (0.86 ml, 12.9 mmol) dropwise. The mixture was refluxed overnight. After the mixture was cooled to room temperature, the mixture was diluted with $CHCl_3$, then ice water was added to the mixture. The organic layer was extracted with $CHCl_3$ and was washed with brine. The extracted organic layer was dried over anhydrous $MgSO_4$, filtered, and concentrated in vacuo to give a pale yellow oil.

The oil was dissolved in THF (50 ml). To the solution was added tert-butyl 1-piperazinecarboxylate (1.20 g, 6.45 mmol), and N,N-diisopropylethylamine (1.12 ml, 6.45 mmol) successively. The mixture was stirred at room temperature for 4 hrs. The mixture was concentrated in vacuo. The residue was diluted with ethylacetate and was washed with brine. The organic layer was dried over anhydrous $MgSO_4$, filtered, and concentrated in vacuo. The residue was purified by column chromatography on silica gel (EtoAc/Hexane) to give tert-butyl 4-[(2-fluoro-4-methyl-5-nitrophenyl)sulfonyl]-1-piperazinecarboxylate (1.00 g, 38.4%) as a pale brown solid.

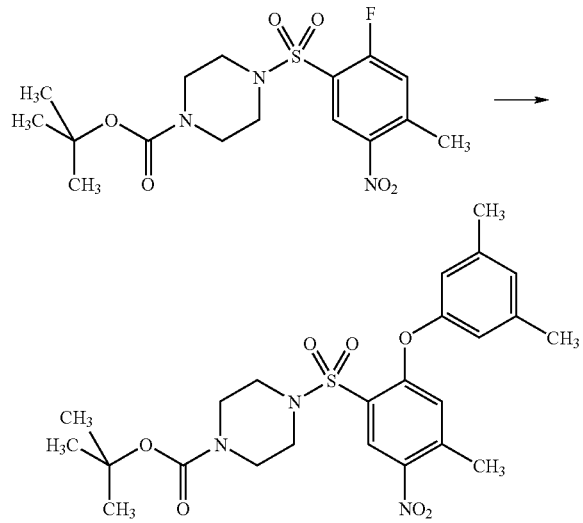

(2) To a solution of 3,5-dimethylphenol (33.3 mg, 0.27 mmol) in 1,4-dioxane (1 ml) was added sodium hydride (60% oil suspension, 11.9 mg, 0.30 mmol) portionwise. The mixture was stirred at room temperature for 30 minutes. To the mixture was added a solution of tert-butyl 4-[(2-fluoromethyl-5-nitrophenyl)sulfonyl]-1-piperazinecarboxylate (100 mg, 0.25 mmol) in 1,4-dioxane (1 ml) slowly. The mixture was stirred at 70° C. overnight. After the mixture was cooled to room temperature, the mixture was concentrated in vacuo. The residue was washed with ice water, then was dried in vacuo to give tert-butyl 4-{[2-(3,5-dimethylphenoxy)-4-methyl-5-nitrophenyl]sulfonyl}-1-piperazinecarboxylate (92.8 mg, 74.1%) as a white solid.

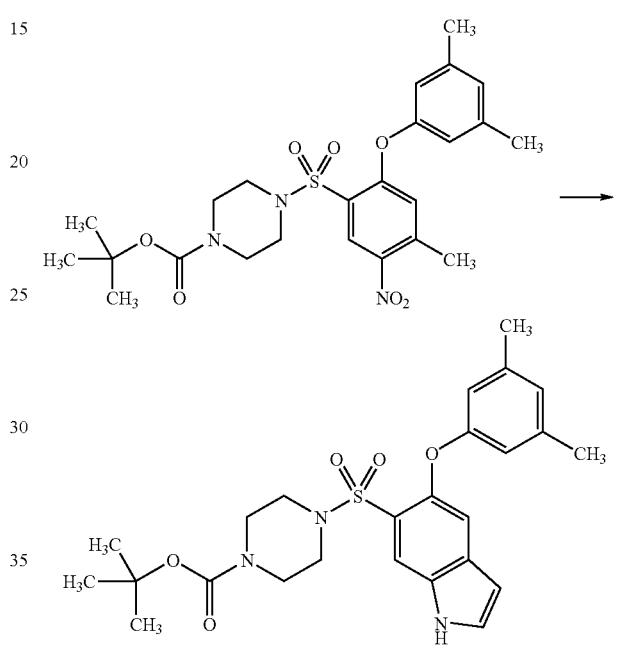

(3) tert-butyl 4-{[2-(3,5-dimethylphenoxy)-4-methyl-5-nitrophenyl]sulfonyl}-1-piperazinecarboxylate (186 mg, 0.368 mmol) was placed in a frame-dried two-necked flask. It was dried in vacuo, then was purged with argon. To the flask was added dry DMF, dimethylformamide dimethyl acetal (0.0585 ml, 0.441 mmol), and pyrrolidine 0.0369 ml, 0.441 mmol). The mixture was stirred at 110° C. for 3 hrs. Additional pyrrolidine (0.0185 ml, 0.22 mmol) was added to the mixture. The mixture was stirred at 110° C. for additional 1 hr. After the mixture was cooled to room temperature, the mixture was transferred to a solution of 4 M aqueous ammonium acetate in DMF, using additional DMF to rinse the mixture into the reaction flask To the solution was added 20% w/v aqueous titanium(III) chloride (1.50 ml, 1.98 mmol) dropwise. The suspension was stirred at room temperature for 15 minutes. The mixture was made basic with 1N aqueous NaOH solution. The mixture was diluted with diethylether. The mixture was filtered, then the organic layer was extracted with diethylether, was washed with brine, dried over anhydrous $MgSO_4$, filtered, and concentrated in vacuo. The residue was purified by column chromatography on silica gel (EtoAc/Hexane) to give tert-butyl 4-{[5-(3,5-dimethylphenoxy)-1H-indol-6-yl]sulfonyl}-1-piperazinecarboxylate (42.2 mg, 23.6%) as a pale brown solid.

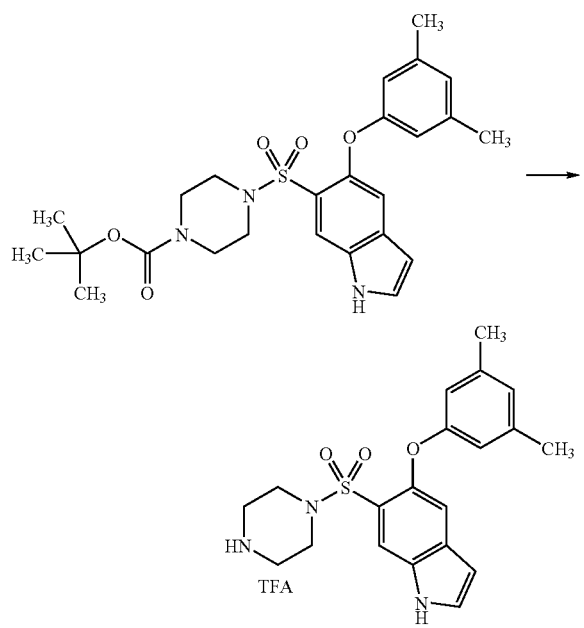

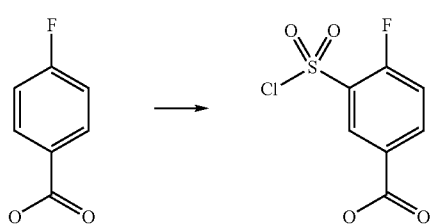

(4) To a solution of tert-butyl 4-{{[5-(3,5-dimethylphenoxy)-1H-indol-6-yl]-sulfonyl}-1-piperazinecarboxylate (15.4 mg, 0.0317 mmol) in $CH_2Cl_2$ (1 ml) was added trifluoroacetic acid (0.10 ml) at 0° C. The mixture was stirred at 0° C. for 2 hrs. Toluene was added to the mixture, then was concentrated in vacuo. The residue was triturated with diethylether to give 5-(3,5-dimethylphenoxy)-6-(1-piperazinylsulfonyl)-1H-indole trifluoroacetate (12.7 mg, 80.2%).

HPLC-MS (ESI): Calcd for $C_{20}H_{23}N_3O_3S$ $[M+H]^+$ 368, Found: 368.

Molecular weight: 499.5129

Activity grade RBA: C

Activity grade $Ca^{2+}$: C

Example 12-1

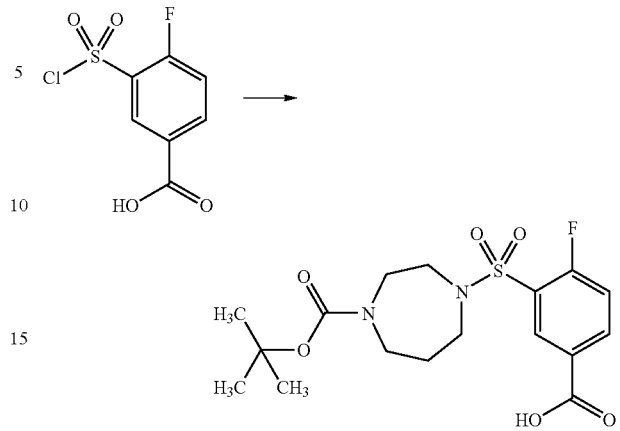

(1) 4-Fluorobenzoic acid (5.0 g, 35.7 mmol) was added to chlorosulfonic acid (31.5 g, 0.27 mol), and the mixture was stirred at 150° C. for 2 hrs. After cooling to room temperature, the mixture was poured into ice-water dropwise with cooling. The resulting white precipitate was collected by filtration. The solid was washed with water, and dried in vacuo to give 3-(chlorosulfonyl)-4-fluorobenzoic acid (6.33 g, 74.3%).

(2) To a solution of 3-(chlorosulfonyl)-4-fluorobenzoic acid (1.0 g, 4.19 mmol) in THF (10 ml) was added N-tert-butyl 1-homopiperazinecarboxylate (0.92 g, 4.61 mmol) in THF (5 ml) dropwise at 0° C., followed by $Et_3N$ (1.08 ml, 6.28 mmol). The mixture was stirred at room temperature for 6 hrs. After quenched by water, the solvent was removed by evaporation. The resulting residue was dissolved in 1N NaOH (24 ml), and washed with $Et_2O$ two times. Then the aqueous layer was acidified to pH 3-4 by 1N HCl, then extracted with EtOAc 3 times. The organic layer was dried over anhydrous $Na_2SO_4$, the solvent was evaporated in vacuo to give 3-{[4-(tert-butoxycarbonyl)-1,4-diazepan-1-yl]sulfonyl}-4-fluorobenzoic acid as a colorless form (1.12 g, 66.4%):

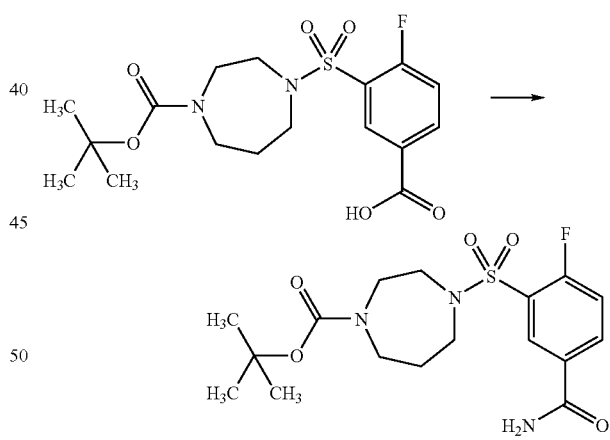

(3) To a solution of 3-{[4-(tert-butoxycarbonyl)-1,4-diazepan-1-yl]sulfonyl}-4-fluorobenzoic acid (250 g, 0.62 mol) in THF (2000 ml) was added CDI (125 g, 0.77 mol) at 0° C. under Ar. The mixture was stirred at 0° C. for 1 hr. Then $NH_3$ gas was bubbled into the mixture for 2 hrs. White precipitate was filtered off, and the filtrate was extracted with EtOAc, washed with 1N HCl, and sat. $NaHCO_3$ solution, and brine. The organic extracts were dried over anhydrous $Na_2SO_4$, the solvent was evaporated in vacuo to give tert-butyl 4-{[5-(aminocarbonyl)-2-fluorophenyl]sulfonyl}-1,4-diazepane-1-carboxylate as a white solid (240 g, 96.2%)

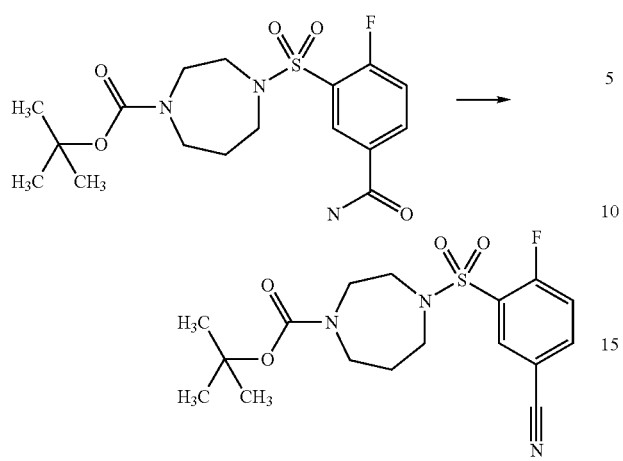

(4) To a solution of tert-butyl 4-{[5-(aminocarbonyl)-2-fluorophenyl]sulfonyl}-1,4-diazepane-1-carboxylate (5.0 g, 12.5 mmol) in dry $CH_2Cl_2$ (150 ml) was added $Et_3N$ (6.94 ml, 49.8 mmol) under Ar. Then the solution was cooled to −5° C. (dry ice/i-PrOH). $(CF_3SO_2)_2O$ (3.14 ml, 18.7 mmol) was added to the mixture dropwise, cooling under 5° C. After 1.5 hrs, the reaction was quenched by water, then extracted with $CH_2Cl_2$, and washed with water and brine. The organic extract was dried over anhydrous $Na_2SO_4$. The solvent was evaporated in vacuo. The resulting residue was purified by column chromatography on silica-gel (Hexane/EtoAc=1/1) to give tert-butyl 4-[(5-cyano-2-fluorophenyl)sulfonyl]-1,4-diazepane-1-carboxylate as a brown oil (4.12 g, 86.3%)

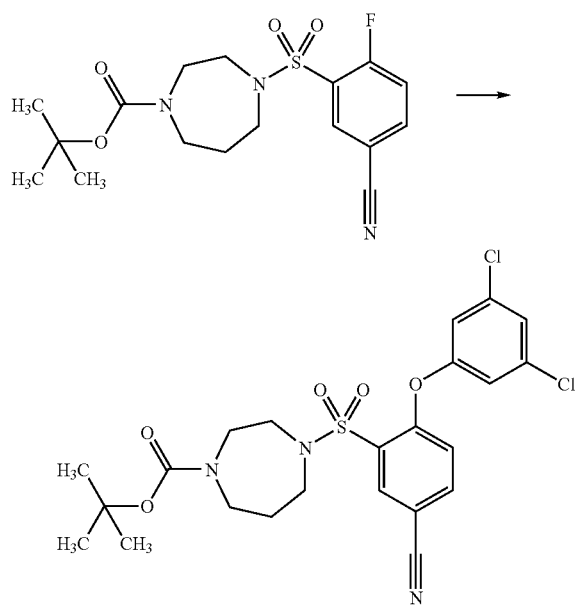

(5) To a solution of tert-butyl 4-[(5-cyano-2-fluorophenyl)sulfonyl]-1,4-diazepane-1-carboxylate (4.12 g, 10.75 mmol) and 3,5-dichlorophenol (5.25 g, 32.2 mmol) in dioxane (100 ml) was added NaH (1.54 g, 37.6 mmol). The mixture was stirred under reflux for 1 hr. After cooled to room temperature, the mixture was quenched by water, and extracted with $CH_2Cl_2$ and washed with 1N NaOH, and brine. The organic extract was dried over anhydrous $Na_2SO_4$, the solvent was evaporated in vacuo. The resulting residue was purified by column chromatography on silica-gel (Hexane/EtoAc=1/1) to give tert-butyl 4-{[5-cyano-2-(3,5-dichlorophenoxy)phenyl]sulfonyl}-1,4-diazepane-1-carboxylate as a white solid (3.08 g, 54.5%)

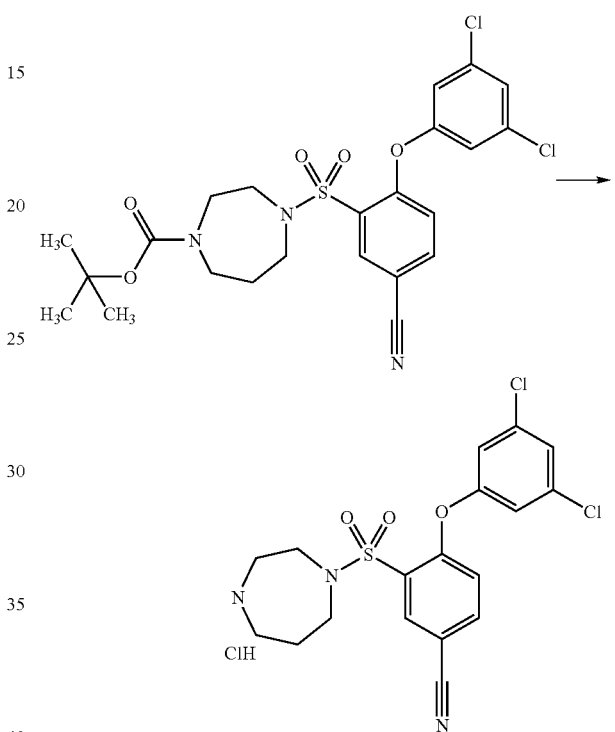

(6) To a solution of tert-butyl 4-{[5-cyano-2-(3,5-dichlorophenoxy)phenyl]-sulfonyl}-1,4-diazepane-1-carboxylate (3.1 g, 5.89 mmol) in $CH_2Cl_2$ (60 ml) was added 4N HCl in dioxane (60 ml). The mixture was stirred at room temperature for 2 hrs. After the solvent was removed by evaporation, the resulting white solid was washed with $CH_3CN$ to give 3-(1,4-diazepan-1-ylsulfonyl)-4-(3,5-dichlorophenoxy)benzonitrile hydrochloride as a white solid (2.13 g, 78.2%): mp 278-280° C.; $^1H$ NMR (500 MHz, DMSO-$d_6$) δ 1.99-2.02 (2H, m), 3.19-3.24 (4H, m), 3.41-3.43 (2H, m), 3.64-3.66 (2H, m), 7.29 (1H, d, J=8.5 Hz), 7.41 (2H, m), 7.59 (1H, m), 8.12 (1H, dd, J=2.2, 8.8 Hz), 8.30 (1H, d, J=1.9 Hz), 8.99 (1H, br); HPLC-MS (ESI): Calcd for $C_{18}H_{18}Cl_3N_3O_3S$ $[M+H]^+$ 426 and 428, found: 426 and 428.

Molecular weight: 462.785

$IC_{50}$ (CCR3): 35 μM $IC_{50}$ ($Ca^{2+}$): 20 μM $IC_{50}$ (Chemotaxis): 8 μM In the similar manner as described in Example 12-1 above, compounds in Example 12-2 and 12-3 as shown in Table 12 were synthesized.

TABLE 12

| EX.No. | molstructure | MW | M + 1 | mp | RBA | Ca2+ |
|---|---|---|---|---|---|---|
| 12-2 | | 442.36752 | 447 | 253 | | B |
| 12-3 | | 483.2034 | 486 | 261 | | B |

Example 13-1

(1) To a mixture of 4-fluoro-3-nitrobenzoic acid (10.00 g, 54.02 mmol) and 3,5-dichlorophenol (13.21 g, 81.03 mmol) in THF (300 ml) was added NaH (5.40 g, 135.05 mmol) at room temperature. The resulting mixture was heated to 70° C. After 2 hrs, the reaction mixture was poured into water and 6N HCl (15 ml) was added. The resulting mixture was extracted with EtOAc. The extract was washed with brine, and dried over MgSO$_4$, the solvent was evaporated in vacuo. The residue was collected by filtration and washed with hexane to give 4-(3,5-dichlorophenoxy)-3-nitrobenzoic acid as a slight yellow powder (15.29 g 86.3%).

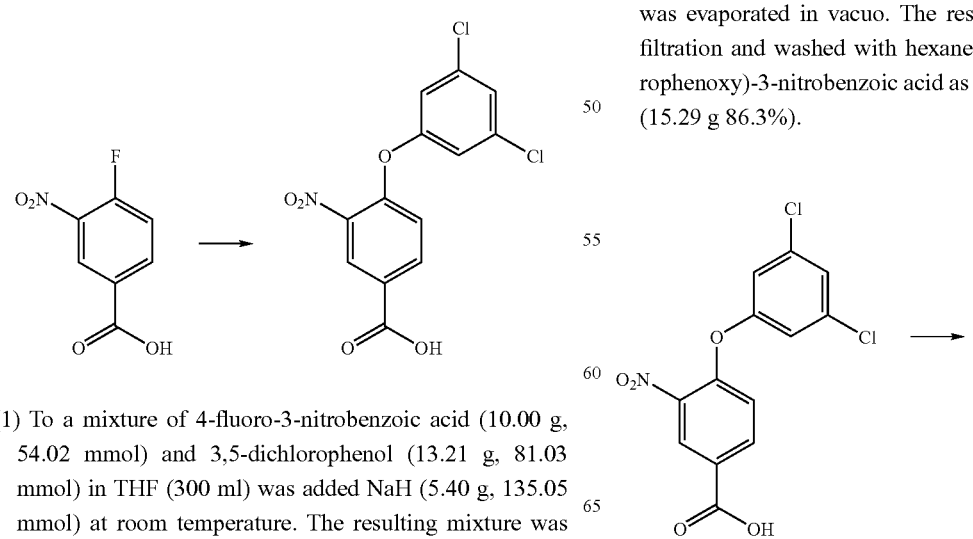

-continued

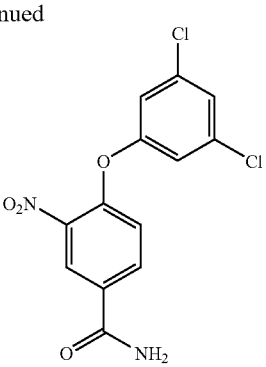

(2) To a cooled solution of 4-(3,5-dichlorophenoxy)-3-nitrobenzoic acid (15.29 g, 46.60 mmol) in THF (300 ml), was added CDI (11.33 g, 69.90 mmol) and resulting mixture was allowed to warm to room temperature. After 2 hrs, the mixture was cooled with ice-bath and then NH₃ gas was introduced directly into the reaction mixture. After 2 hrs, the reaction mixture was condensed under reduce pressure. The residue was dissolved in water and the resulting mixture was extracted with EtOAc. The extract was washed with 1N NaOH, 1N HCl, and brine, dried over MgSO₄. The solvent was evaporated in vacuo. The crude product was collected by filtration and washed with MeCN to give 4-(3,5-dichlorophenoxy)-3-nitrobenzamide as a white powder (15.72 g, quantitative).

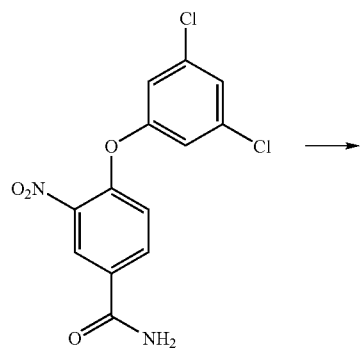

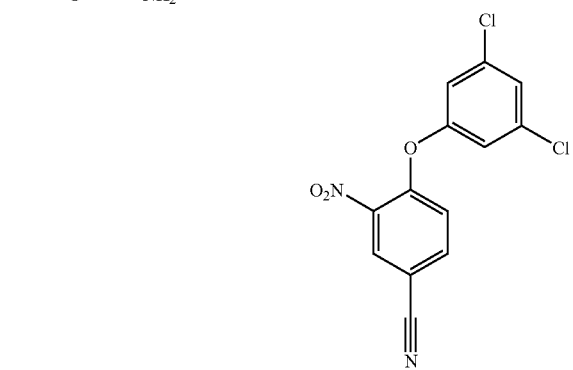

(3) The solution of 4-(3,5-dichlorophenoxy)-3-nitrobenzamide (15.50 g, 47.38 mmol) and i-Pr₂EtN (49.52 ml, 284.30 mmol) in CH₂Cl₂ (500 ml) was cooled to -5° C. with dry-ice/1-PrOH bath. Tf₂O (16.04 ml, 94.77 mmol) was added dropwise to the mixture below 0° C. and then additional i-Pr₂EtN (24.76 ml, 142.15 mmol) and Tf₂O (12.03 ml, 71.08 mmol) was added. The mixture was stirred at 0° C. for 30 min. Water was added into the reaction mixture and the resulting mixture was condensed under reduced pressure. The obtained residue was partitioned between water and EtOAc and the resulting mixture was extracted with EtOAc. The extract was washed with 1N HCl and brine, dried over MgSO₄ The solvent was evaporated in vacuo. The residue was purified by column chromatography on silica-gel (CHCl₃/EtoAc=100/0 to 95/5) to give 5-cyano-2-(3,5-dichlorophenoxy)nitrobenzene as a white powder (4.08 g, 27.9%).

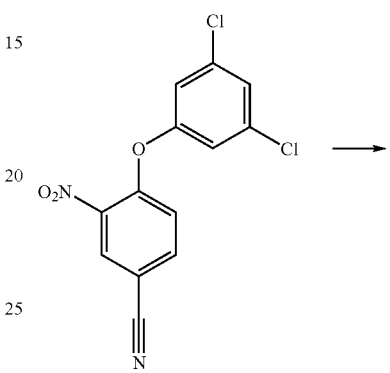

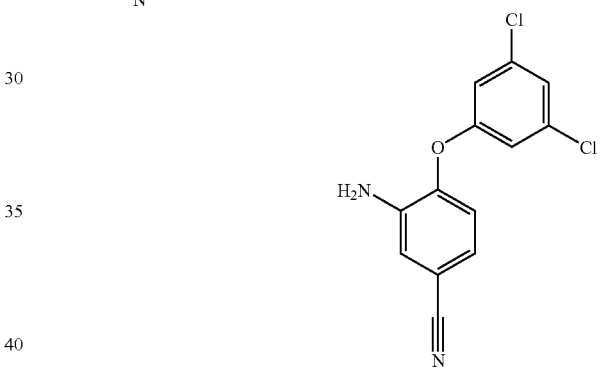

(4) The mixture of 5-cyano-2-(3,5-dichlorophenoxy)nitrobenzene (4.08 g, 13.20 mmol) and Tin(II) chloride dihydrate (17.87 g, 79.20 mmol) in EtOAc (200 ml) was heated to reflux for 3 hrs. After cooled to room temperature, the reaction mixture was poured into sat. NaHCO₃. The mixture was extracted with EtOAc. The extract was washed with brine, and dried over MgSO₄. The solvent was evaporated in vacuo to give 5-cyano-2-(3,5-dichlorophenoxy) aniline (3.53 g, 95.8%).

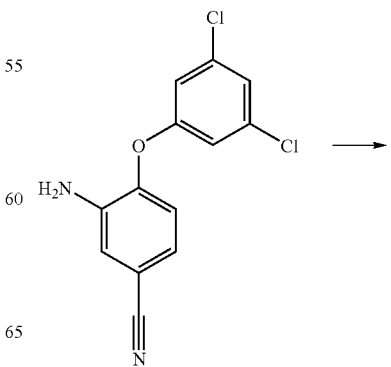

-continued

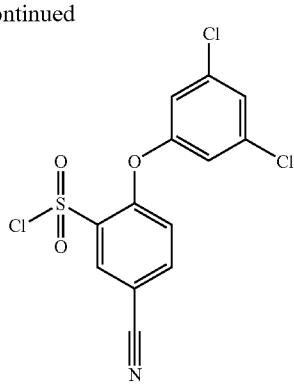

(5) 5-Cyano-2-(3,5-dichlorophenoxy)aniline (3.53 g, 12.65 mmol) was dissolved in the mixture of conc. HCl (6.33 ml) and AcOH 2.53 ml). The solution was cooled to 0° C. and sodium nitrite (0.96 g, 13.91 mmol) in water (1.27 ml) was added dropwise with stirring. After 30 min, the reaction mixture was added dropwise to the suspended mixture of CuCl (0.63 g, 6.32 mmol) in saturated solution of $SO_2$ in AcOH (25.32 ml) at 5° C. The reaction mixture was stirred at 10° C. for 30 min. poured into water and the resulting mixture was extracted with EtOAc. The extract was washed with sat. $NaHCO_3$, brine, and dried over $MgSO_4$. The solvent was evaporated in vacuo to give 5-cyano-2-(3,5-dichlorophenoxy)phenylsulfonylchloride as a brown powder (4.45 g, 97%).

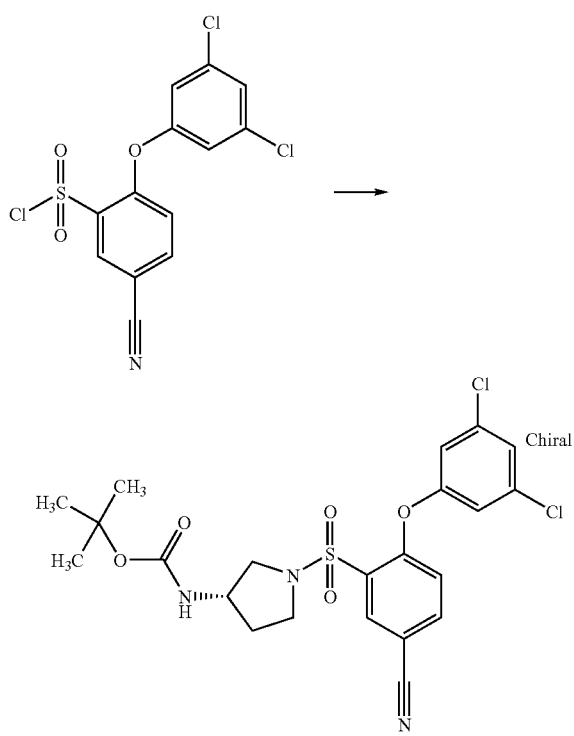

(6) To a solution of 5-cyano-2-(3,5-dichlorophenoxy)phenyl-sulfonylchloride (0.03 g 0.08 mmol) in THF (1 ml), (3S)-(tert-butoxycarbonylamino)pyrrolidine (0.05 g, 0.25 mmol) was added. The reaction mixture was stirred at room temperature overnight, then poured into water and the resulting mixture was extracted with EtOAc. The extract was washed with brine, and dried over $MgSO_4$. The solvent was evaporated in vacuo. The residue was purified by preparative TLC on silica gel ($CH_2Cl_2/CH_3OH=25/1$) to give 1-{5-cyano-2-(3,5-dichlorophenoxy)phenylsulfo-nyl}-(3S)-(tert-butoxycarbonylamino)pyrrolidine as an oil (0.02 g, 47%).

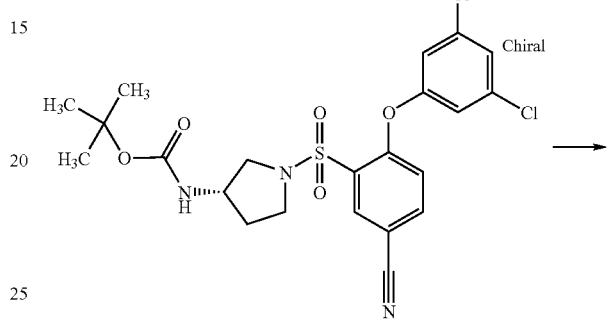

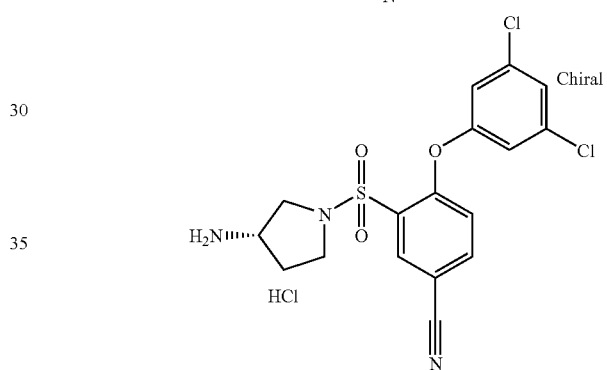

(7) To the solution of 1-{5-cyano-2-(3,5-dichlorophenoxy) phenylsulfonyl}-(3S)(tert-butoxycarbonylamino)pyrroli-dine (0.03 g, 0.04 mmol) in 1,4-dioxane (1 ml) was added 4N HCl (1 ml) in 1,4-dioxane. The reaction mixture was stirred at room temperature overnight. The solvent was evaporated in vacuo. The obtained residue was dissolved in THF followed by addition of ether. The produced precipitate was collected by filtration, washed with ether and dried in vacuo to give 1-{5-cyano-2-(3,5-dichlorophenoxy)phe-nylsulfonyl}-(3S)aminopyrrolidine hydrocloride as a white powder (13.4 mg, 77%): mp 276° C.; $^1$H NMR (500 MHz, DMSO-$d_6$) δ 1.92-1.97 (1H, m), 2.15-2.22 (1H, m), 3.34-3.41 (2H, m), 3.51-3.56 (1H, m), 3.63-3.67 (1H, m), 3.79-3.83 (1H, m), 7.34 (1H, d, J=8.8 Hz), 7.39 (2H, dd, J=1.6, 1.9 Hz), 8.13 (1H, dd, J=8.5, 2.2 Hz), 8.21 (3H, br), 8.29 (1H, d, J=1.9); HPLC-MS (ESI): calcd for $C_{17}H_{15}Cl_2N_3O_3S$ [M+H]$^+$ 411 and 413, Found: 411 and 413.

Molecular weight: 448.758

Activity grade $Ca^{2+}$: A

In the similar manner as described in Example 13-1 above, compounds in Example 13-2 to 13-12 as shown in Table 13 were synthesized.

TABLE 13

| EX.No. | molstructure | MW | M + 1 | mp | RBA | Ca2+ |
|---|---|---|---|---|---|---|
| 13-2 | | 542.4886 | 542 | 90-93 | B | B |
| 13-3 | | 480.41691 | 480 | 144-145 | | A |
| 13-4 | | 424.30855 | 424 | 311–312 | A | A |

TABLE 13-continued

| EX.No. | molstructure | MW | M + 1 | mp | RBA | Ca2+ |
|---|---|---|---|---|---|---|
| 13-5 | (Chiral structure) | 452.36273 | 452 | 163-165 | B | A |
| 13-6 | (Chiral structure) | 452.36273 | 452 | 164-165 | 30 | 40 + G9 |
| 13-7 | (structure) | 520.86613 | 483 | 240 | A | A |

TABLE 13-continued

| EX.No. | molstructure | MW | M + 1 | mp | RBA | Ca2+ |
|---|---|---|---|---|---|---|
| 13-8 | | 422.72013 | 426 | 214 | | A |
| 13-9 | | 492.76832 | 457 | 262 | 7 | 12 + G12 |
| 13-10 | | 470.76473 | 434 | 104 | | A |
| 13-11 | | 466.38982 | 467 | | 13 | 8 |

TABLE 13-continued

| EX.No. | molstructure | MW | M + 1 | mp | RBA | Ca2+ |
|---|---|---|---|---|---|---|
| 13-12 | | 452.36273 | 452 | 161 | A | |

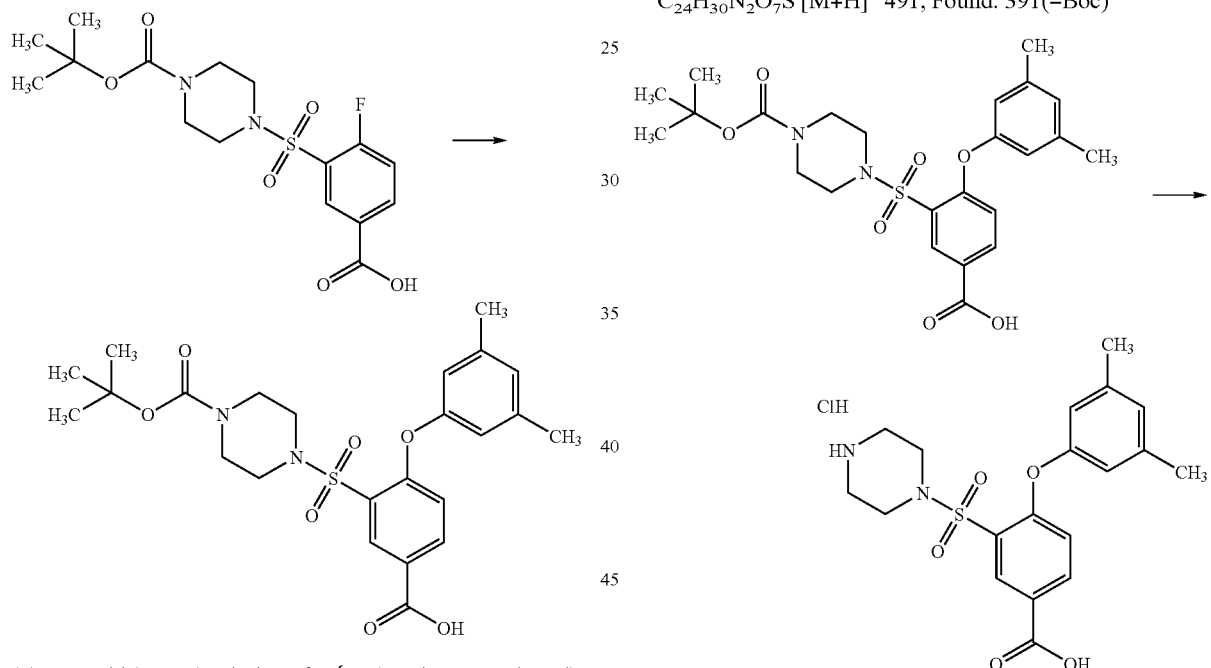

Example 14-1

(1) To a cold (10° C.) solution of 3-{[4-(tert-butoxycarbonyl)-1-piperazinyl]-sulfonyl}-4-fluorobenzoic acid (0.200 g, 0.515 mmol) and 3,5-dimethylphenol (0.063 g, 0.515 mmol) in 1,4-dioxane (1.0 ml) was added NaH (0.041 g, 1.030 mmol), and the stirring was continued for 15 min. The mixture was heated at 120° C. for 3 hrs. N-Methyl-2-pyrollidone (1.0 ml) was added to the mixture, which was then heated at 120° C. overnight. After cooled to room temperature, the mixture was quenched with water and then extracted with a 1:1 mixture of EtOAc and hexane. The aqueous phase was separated, and the organic phase was extracted with water. The combined aqueous phase was acidified to pH 3-4 with 1N HCl, and then extracted with EtOAc. The separated organic phase was washed with water and brine, dried over $Na_2SO_4$. The solvent was evaporated in vacuo. The residue was suspended in boiled MeOH for 1 h. After cooling to room temperature, the precipitate was collected by filtration, washed with MeOH and dried in vacuo to give 3-{[4-(tert-butoxycarbonyl)-1-piperazinyl]sulfonyl}-4-(3,5-dimethylphenoxy)benzoic acid (0.101 g, 40.0%): HPLC-MS (ESI): Calcd for $C_{24}H_{30}N_2O_7S$ [M+H]$^+$ 491, Found: 391(−Boc)

(2) To a solution of 3-{[4-(tert-butoxycarbonyl)-1-piperazinyl]sulfonyl}-4-(3,5-dimethylphenoxy)benzoic acid (0.030 g, 0.061 mmol) in 1,4-dioxane (0.5 ml) was added 4N HCl in 1,4-dioxane (1.5 ml). The mixture was further stirred at room temperature for 3 hrs, and then concentrated in vacuo. The residue was washed twice with $CH_3CN$ and dried in vacuo to give 4-(3,5-dimethylphenoxy)-3-(1-piperazinylsulfonyl)benzoic acid hydrochloride (0.027 g, quantitative): $^1$H NMR (500 MHz, DMSO-$d_6$) δ 2.31 (6H, s), 3.17 (4H, br), 3.47 (4H, br), 6.87 (1H, s), 6.96 (1H, s), 6.98 (1H, br), 8.15 (1H, dd, J=2.2, 8.8 Hz), 8.39 (1H, d, J=2.2 Hz), 9.19 (1H, br), 13.36 (1H, br); HPLC-MS (ES): Calcd for $C_{19}H_{22}N_2O_5S$ [M+H]$^+$ 391, Found: 391.

Molecular weight: 426.922

Activity grade $Ca^{2+}$:A

In the similar manner as described in Example 14-1 above, compounds in Example 14-2 to 14-4 as shown in Table 14 were synthesized.

TABLE 14
| EX.No. | molstructure | MW | M + 1 | mp | RBA | Ca2+ |
|---|---|---|---|---|---|---|
| 14-2 | | 490.5799 | 391 | 222 | | A |
| 14-3 | ClH | 467.75844 | 431 | >260 | | A |
| 14-4 | | 487.72433 | 466 | 307 | | B |
Example 15-1
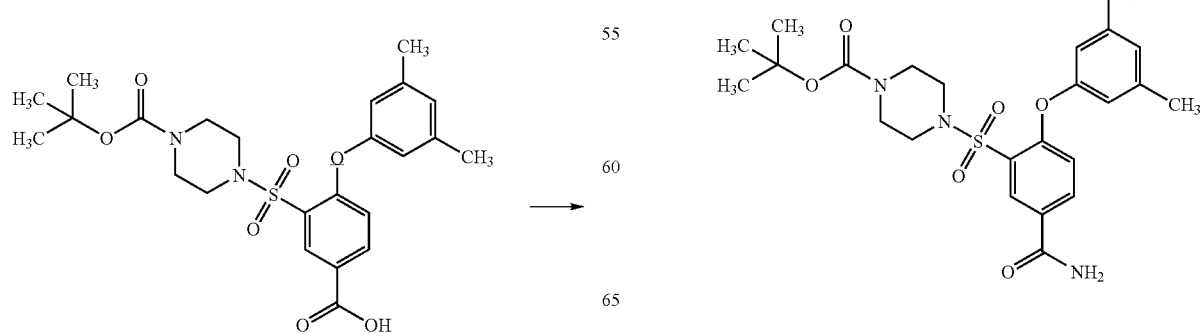
-continued (1) To a solution of 3-{[4-(tert-butoxycarbonyl)-1-piperazinyl]sulfonyl}-4-(3,5-dimethylphenoxy)benzoic acid (0.100 g, 0.204 mmol) in THF (1.0 ml) was added 1,1'-carbonylimidazole (0.041 g, 0.255 mmol), and the mixture was stirred at room temperature. After 3 hrs, 0.5M $NH_3$ in 1,4-dioxane was added, and the stirring was continued overnight. The resultant mixture was concentrated in vacuo, and the residue was partitioned between EtOAc and saturated $NaHCO_3$. The separated organic phase was washed with water and brine, dried over $Na_2SO_4$. The solvent was evaporated in vacuo. The solid obtained was washed with EtOH and dried in vacuo to give tert-butyl 4-{[5-(aminocarbonyl)-2-(3,5-dimethylphenoxy)phenyl]sulfonyl}-1-piperazinecarboxylate (0.071 g, 71.1%).

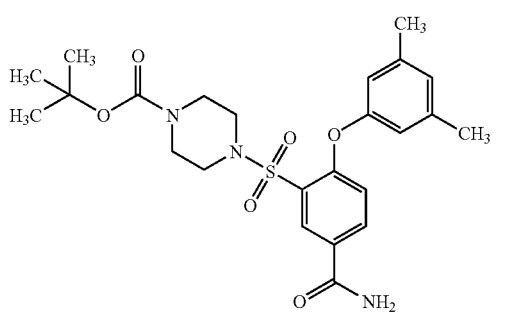

(2) To a suspension of tert-butyl 4-{[5-(aminocarbonyl)-2-(3,5-dimethylphenoxy)phenyl]sulfonyl}-1-piperazinecarboxylate (0.057 g, 0.116 mmol) in 1,4-dioxane (1.0 ml) was added 4N HCl in 1,4-dioxane (3.0 ml), and the mixture was stirred at room temperature for 2 hrs. The mixture was concentrated in vacuo, washed twice with $CH_3CN$ and dried in vacuo to give 4-(3,5-dimethylphenoxy)-3-(1-piperazinylsulfonyl)benzamide hydrochloride (0.047 g, 94.8%): $^1$H NMR (500 MHz, DMSO-$d_6$) δ 2.30 (6H, s), 3.16 (4H, br), 3.45 (4H, br), 6.83 (1H, s), 6.94 (1H, s), 6.95 (1H, d, J=8.8 Hz), 7.51 (1H, s), 8.11 (1H, dd, J=2.2, 8.5 Hz), 8.18 (1H, s), 8.37 (1H, d, J=2.2 Hz), 9.22 (2H, s); HPLC-MS (ESI): Calcd for $C_{19}H_{23}N_3O_4S$ [M+H]$^+$ 390, Found: 390.

Molecular weight: 425.937

Activity grade RBA:

Activity grade $Ca^{2+}$: A

Example 15-2

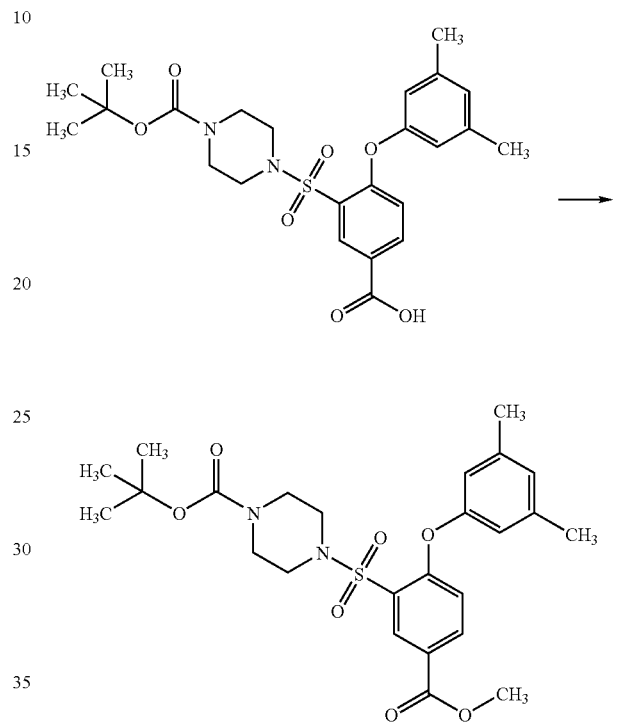

(1) To a mixture of 3-{[4-(tert-butoxycarbonyl)-1-piperazinyl]sulfonyl}-4-(3,5-dimethylphenoxy)benzoic acid (0.300 g, 0.612 mmol), $K_2CO_3$, (0.169 g, 1.223 mmol) and DMF (3.0 ml) was added MeI (0.174 g, 1.223 mmol), and the stirring was continued at room temperature overnight. The mixture was quenched with water, and extracted with EtOAc. The separated organic phase was washed with water and brine, dried over $Na_2SO_4$. The solvent was evaporated in vacuo, The residue was recrystallized from MeOH to give tert-butyl 4-{[2-(3,5-dimethylphenoxy)-5-(methoxycarbonyl)phenyl]sulfonyl}-1-piperazinecarboxylate (0.276 g, 89%).

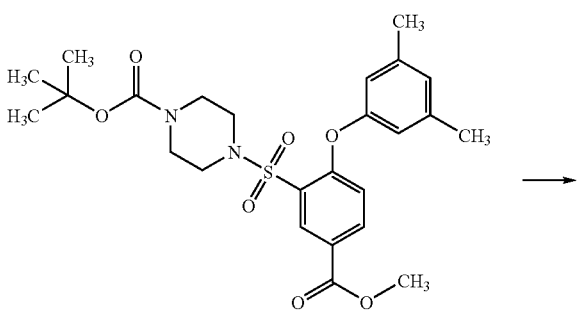

-continued

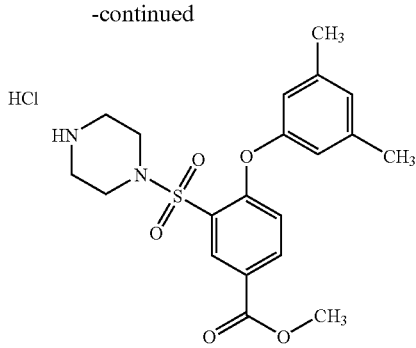

(2) To a suspension of tert-butyl 4-{[2-(3,5-dimethylphenoxy)-5-(methoxycarbonyl)phenyl]sulfonyl}-1-piperazinecarboxylate (0.030 g, 0.059 mmol) in 1,4-dioxane (1.0 ml) was added 4N HCl in 1,4-dioxane (3.0 ml). The resulting clear solution was stirred at room temperature for 3 hrs. The mixture was concentrated in vacuo, washed twice with Et$_2$O and dried in vacuo to give methyl 4-(3,5-dimethylphenoxy)-3-(1-piperazinylsulfonyl)benzoate hydrochloride (0.027 g, quantative): mp 120° C.; $^1$H NMR (500 MHz, DMSO-d$_6$) δ 2.31 (6H, s), 3.16 (4H, br), 3.48 (4H, br), 3.88 (3H, s), 6.89 (2H, s), 6.97 (1H, d, J=2.3 Hz), 6.98 (1H, s), 8.17 (2H, dd, J=2.3, 9.0 Hz), 8.40 (1H, d, J=2.3 Hz), 9.22 (2H, br); HPLC-MS (ES): Calcd for C$_{20}$H$_{24}$N$_2$O$_5$S [M+H]+405, Found: 405.

Molecular weight: 440.949

Activity grade Ca$^{2+}$: A

In the similar manner as described in Example 15-1 or 15-2 above, compounds in Example 15-3 and 15-4 as shown in Table 15 were synthesized.

Example 16-1

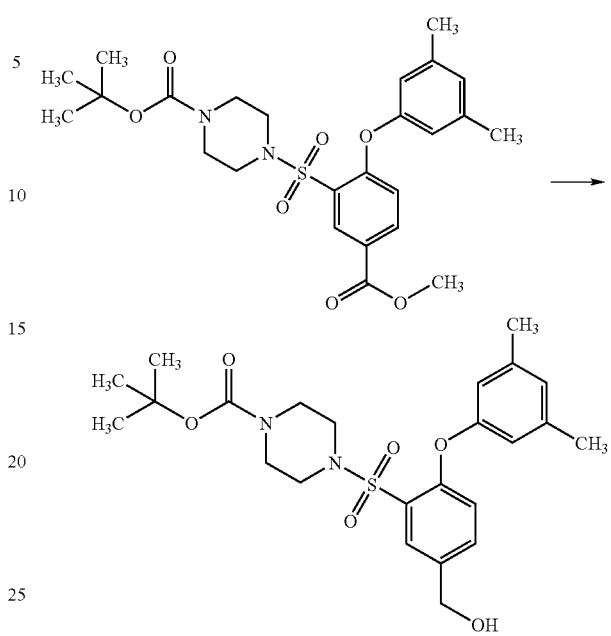

(1) To a cold (0° C.) solution of 4-{[2-(3,5-dimethylphenoxy)-5-(methoxycarbonyl)phenyl]sulfonyl}-1-piperazinecarboxylate (0.227 g, 0.450 mmol) in THF (3.0 ml) was added LiBH$_4$ (0.012 g, 0.540 mmol). The mixture was stirred at room temperature for 3 hrs, and at 60° C. for 4 hrs. After cooled to room temperature, the mixture was

TABLE 15

| EX.No. | molstructure | MW | M + 1 | mp | RBA | Ca2+ |
|---|---|---|---|---|---|---|
| 15-3 | | 460.38286 | 424 | 161 | | B |
| 15-4 | | 484.76414 | 488 | >300 | | B | quenched with saturated NH₄Cl, and extracted with EtOAc. The separated organic phase was washed with water and brine, dried over Na₂SO₄. The solvent was evaporated in vacuo. The residue was purified by recrystallization from CH₃CN to give tert-butyl 4-{[2-(3,5-dimethylphenoxy)-5-(hydroxymethyl)phenyl]sulfonyl}-1-piperazinecarboxylate (0.156 g, 72.8%).

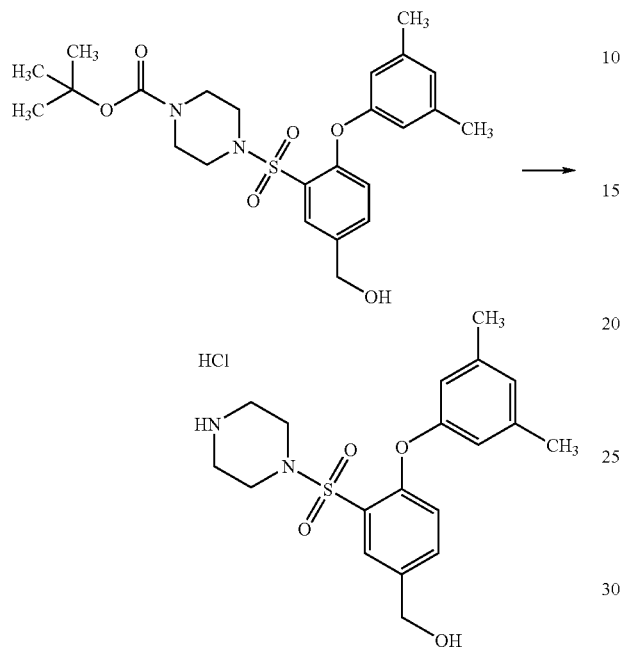

(2) To a solution of tert-butyl 4-{[2-(3,5-dimethylphenoxy)-5-(hydroxymethyl)phenyl]sulfonyl}-1-piperazinecarboxylate (0.027 g, 0.057 mmol) in 1,4-dioxane (1.0 ml) was added 4N HCl in 1,4-dioxane (3.0 ml). The mixture was stirred at room temperature for 3 hrs. The mixture was concentrated in vacuo, washed twice with Et₂O and dried in vacuo to give [4-(3,5-dimethylphenoxy)-3-(1-piperazinylsulfonyl)phenyl]methanol hydrochloride (0.020 g, 85.5%): mp 160° C. ¹H NMR (500 MHz, DMSO-d₆) δ 2.27 (6H, s), 3.14 (4H, br), 3.39 (4H, br), 4.53 (2H, d, J=5.7 Hz), 5.42 (1H, t, J=5.7 Hz), 6.71 (2H, s), 6.86 (1H, s), 6.96 (1H, d, J=8.5 Hz), 7.57 (1H, dd, J=2.2, 8.5 Hz), 7.83 (1H, d, J=1.9 Hz), 9.12 (2H, br); HPLC-MS (ESI): Calcd for C₁₉H₂₄N₂O₄S [M+H]⁺ 377, Found: 377.

Molecular weight: 412.939

Activity grade Ca²⁺: A

Example 17-1

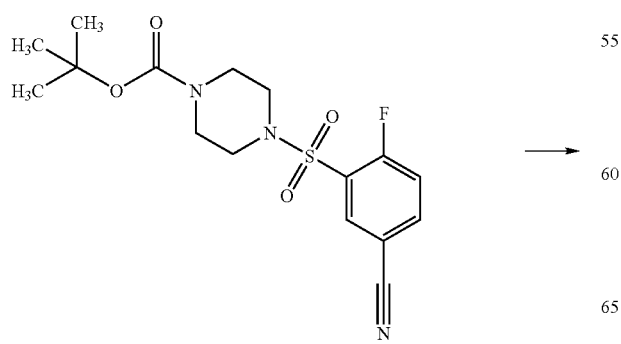

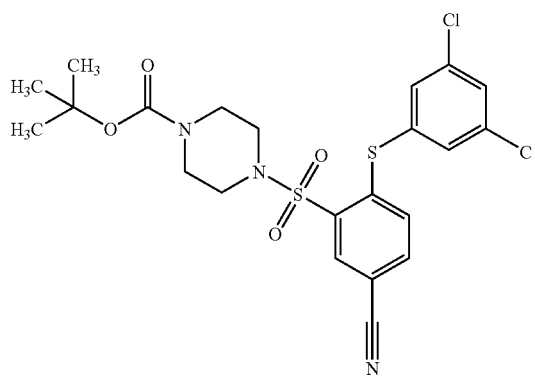

(1) To a stirred suspension of NaH (60%, 0.015 g, 0.375 mmol) in 1,4-dioxane (2.0 ml) was added 3,5-dichlorothiophenol (0.067 g, 0.374 mmol). After 15 min, tert-butyl 4-[(5-cyano-2-fluorophenyl)sulfonyl]-1-piperazinecarboxylate (0.100 g, 0.271 mmol) was added, and the suspension was stirred at room temperature for 10 min. THF (0.5 ml) was added, and the stirring was continued for 2 hrs. The mixture was quenched with water, and extracted with EtOAc and saturated aqueous NaHCO₃ solution. The separated organic phase was washed with water and brine, dried over Na₂SO₄. The solvent was evaporated in vacuo. The residue was recrystallized from CH₃CN to give tert-butyl 4-({5-cyano-2-[(3,5-dichlorophenyl)sulfanyl]phenyl}sulfonyl)-1-piperazinecarboxylate (0.088 g, 61.5%).

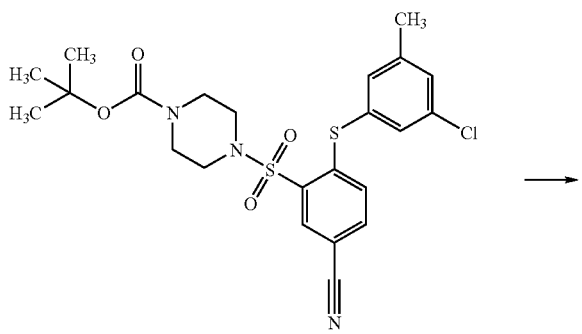

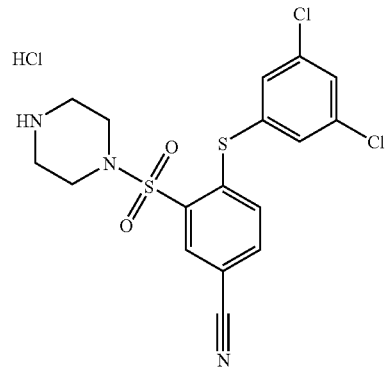

(2) To a solution of tert-butyl 4-({5-cyano-2-[(3,5-dichlorophenyl)sulfanyl]-phenyl}sulfonyl)-1-piperazinecarboxylate (0.020 g, 0.038 mmol) in 1,4-dioxane (1.0 ml) was added 4N HCl in 1,4-dioxane (3.0 ml), and the stirring was continued for 3 hrs. The mixture was concentrated in vacuo. The residue was recrystallized from diisopropylether. The solid obtained was washed with diisopropylether, dried in vacuo to give 4-[(3,5-dichlorophenyl)sulfanyl]-3-(1-piperazinylsulfonyl)benzonitrile hydrochloride (0.017 g, 96.6%): mp 82° C. $^1$H NMR (500 MHz, DMSO-d$_6$) δ 3.19 (4H, br), 3.53 (4H, br), 7.18 (1H, d, J=8.5 Hz), 7.73 (1H, d, J=1.9 Hz), 7.87 (1H, t, J=1.9 Hz), 7.97 (1H, dd, J=1.3, 8.5 Hz), 8.3 (1H, d, J=1.6 Hz), 8.99 (2H, br); HPLC-MS (ESI): Calcd for $C_{17}H_{15}Cl_2N_3O_2S_2$ [M+H]$^+$ 428, Found: 428.

Molecular weight: 464.823

IC$_{50}$ (CCR3): 3 μM

IC$_{50}$ (Ca$^{2+}$): 2 μM

IC$_{50}$ (Chemotaxis): 2 μM

In the similar manner as described in Example 17-1 above, compounds in Example 17-2 and 17-3 as shown in Table 17 were synthesized.

Example 18-1

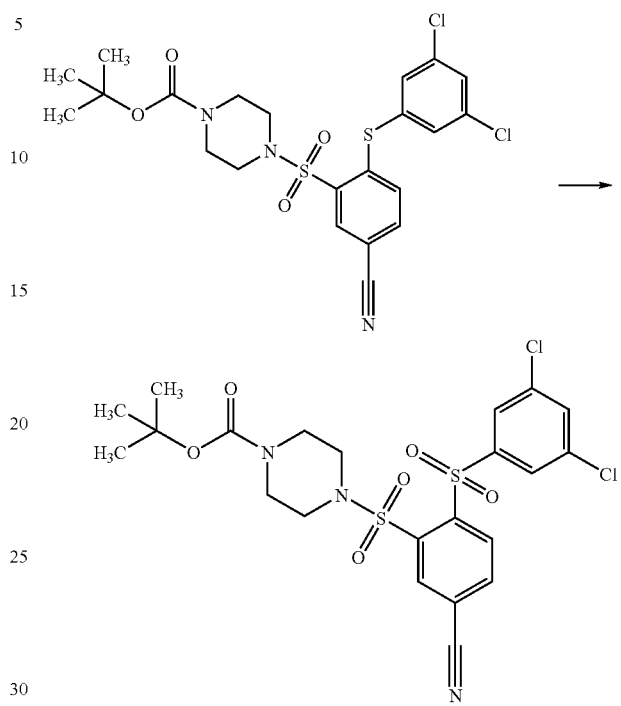

TABLE 17

| EX. No. | moistructure | MW | M + 1 | mp | RBA | Ca2+ |
|---|---|---|---|---|---|---|
| 17-2 | | 516.53436 | 516 | 124 | | A |
| 17-3 | | 478.85006 | 442 | 277-278 | 3 | 1 |

(1) To a stirred mixture of tert-butyl 4-({5-cyano-2-[(3,5-dichlorophenyl)sulfanyl]phenyl}sulfonyl)-1-piperazinecarboxylate (0.011 g, 0.020 mmol), $CCl_4$ (0.4 ml), $CH_3CN$ (0.4 ml) and water (0.8 ml) was added $NaIO_4$ (0.030 g, 0.142 mmol) followed by $RuCl_3$ (0.003 g, 0.014 mmol). The mixture was stirred at room temperature for 4 hrs. The mixture was partitioned between EtOAc and water. The separated organic phase was washed with saturated aqueous $NaHCO_3$ solution and brine, dried over $Na_2SO_4$. The solvent was evaporated in vacuo. The residue was dissolved in hot $CH_3CN$, and allowed to cool to room temperature. The precipitate was collected by filtration, washed with $CH_3CN$, and dried in vacuo to give tert-butyl 4-({5-cyano-2-[(3,5-dichlorophenyl)sulfonyl]phenyl}sulfonyl)-1-piperazinecarboxylate (0.016 g, 60.3%).

Example 19-1

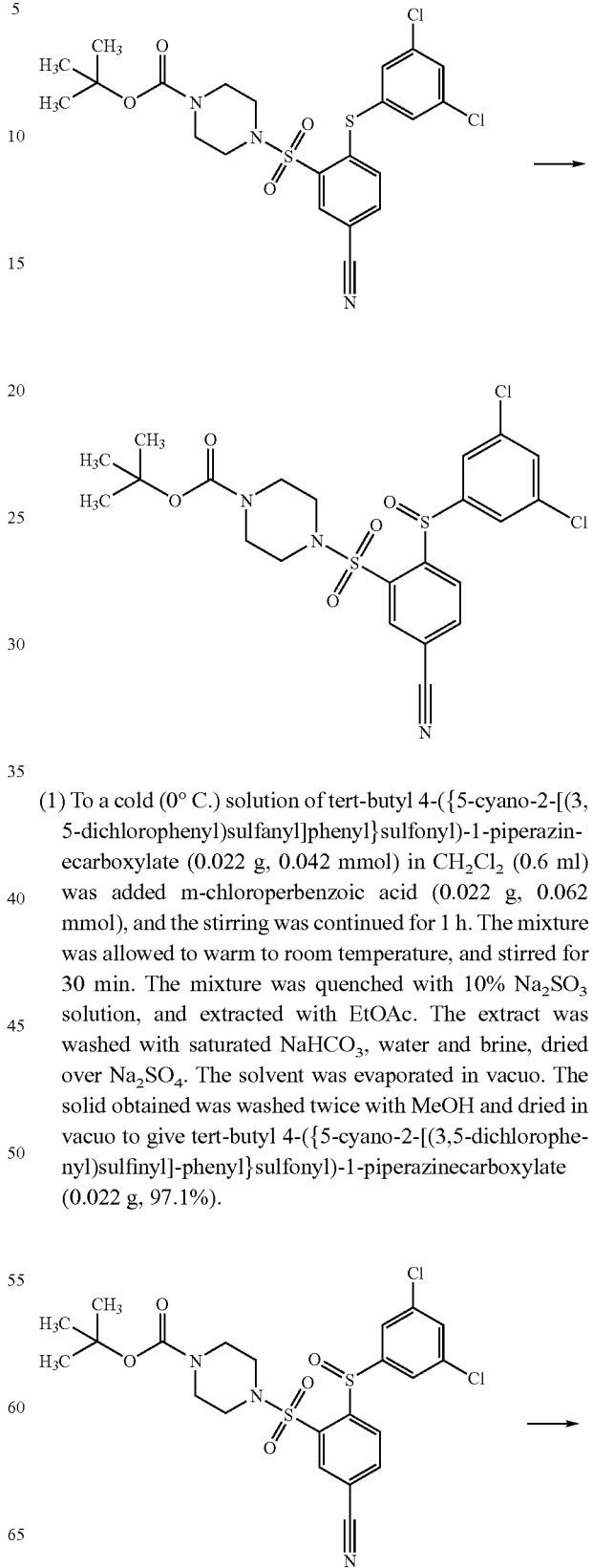

(2) To a suspension of tert-butyl 4-({5-cyano-2-[(3,5-dichlorophenyl)sulfonyl]-phenyl}sulfonyl)-1-piperazinecarboxylate (0.011 g) in 1,4-dioxane (0.5 ml) was added 4N HCl in 1,4-dioxane (1.5 ml), and the stirring was continued for 3 hrs. The mixture was concentrated in vacuo, and recrystallized with diisopropylether. The obtained solid was washed with diisopropylether, and dried in vacuo to give 4-[(3,5-dichlorophenyl)sulfonyl]-3-(1-piperazinylsulfonyl)benzonitrile hydrochloride (0.008 g, 82%): mp 258° C. $^1H$ NMR (500 MHz, DMSO-$d_6$) δ 3.15 (4H, br), 3.57 (4H, br), 7.94 (2H, d, J=1.9 Hz), 8.05 (1H, t, J=1.9 Hz), 8.52-8.55 (2H, m), 8.72 (1H, d, J=8.5 Hz), 8.96 (2H, br); FAB-MS: Calcd for $C_{17}H_{15}Cl_2N_3O_4S_2$ $[M+H]^+$ 460, Found: 460.

Molecular weight: 496.821

$IC_{50}$ (CCR3): 1.2 μM $IC_{50}$ ($Ca^{2+}$): 7 μM (1) To a cold (0° C.) solution of tert-butyl 4-({5-cyano-2-[(3,5-dichlorophenyl)sulfanyl]phenyl}sulfonyl)-1-piperazinecarboxylate (0.022 g, 0.042 mmol) in $CH_2Cl_2$ (0.6 ml) was added m-chloroperbenzoic acid (0.022 g, 0.062 mmol), and the stirring was continued for 1 h. The mixture was allowed to warm to room temperature, and stirred for 30 min. The mixture was quenched with 10% $Na_2SO_3$ solution, and extracted with EtOAc. The extract was washed with saturated $NaHCO_3$, water and brine, dried over $Na_2SO_4$. The solvent was evaporated in vacuo. The solid obtained was washed twice with MeOH and dried in vacuo to give tert-butyl 4-({5-cyano-2-[(3,5-dichlorophenyl)sulfinyl]-phenyl}sulfonyl)-1-piperazinecarboxylate (0.022 g, 97.1%).

-continued

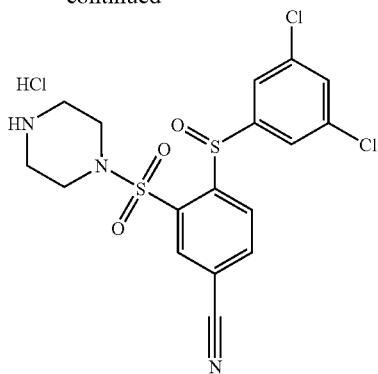

(2) To a suspension of tert-butyl 4-({5-cyano-2-[(3,5-dichlorophenyl)sulfinyl]-phenyl}sulfonyl)-1-piperazinecarboxylate (0.017 g, 0.031 mmol) in 1,4-dioxane (1.0 ml) was added 4N HCl in 1,4-dioxane (3.0 ml). The mixture was stirred at room temperature for 3 hrs, and then concentrated in vacuo. The residue was washed twice with $CH_3CN$, and dried in vacuo to give 4-[(3,5-dichlorophenyl)sulfinyl]-3-(1-piperazinylsulfonyl)benzonitrile hydrochloride (0.008 g, 53.3%): mp 219° C. $^1$H NMR (500 MHz, DMSO-$d_6$) (3.20-3.24 (4H, m), 3.43-3.46 (4H, m), 7.74 (1H, d, J=1.9 Hz), 7.85 (1H, t, J=1.9 Hz), 8.42 (1H, d, J=1.6 Hz), 8.47 (1H, dd, J=1.6, 8.2 Hz), 8.52 (1H, d, J=8.2 Hz), 8.87 (2H, br); FAB-MS: Calcd for $C_{17}H_{15}Cl_2N_3O_3S_2$ [M+H]$^+$ 444, Found: 444.

Molecular weight: 480.822

Activity grade Ca$^{2+}$: B

Example 20-1

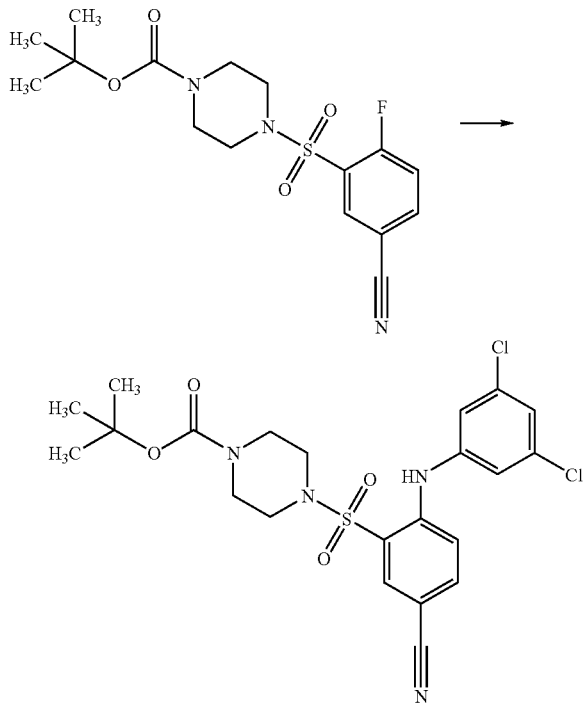

(1) A solution of tert-butyl 4-[(5-cyano-2-fluorophenyl)sulfonyl]-1-piperazinecarboxylate (0.100 g, 0.271 mmol) in THF (2.0 ml) was cooled with a water bath, and KOtBu (0.033 g, 0.298 mmol) was added with stirring. The mixture was heated at reflux for 7 hrs. After cooled to room temperature, KOtBu (0.030 g, 0.267 mmol) was added, and the mixture was heated at reflux overnight. After cooled to room temperature, the mixture was quenched with saturated $NH_4Cl$, and extracted with EtOAc. The separated organic phase was washed with water and brine, dried over $Na_2SO_4$. The solvent was evaporated in vacuo. The residue was purified by column chromatography on silica gel (Hexane/EtOAc=4/1). The product obtained was suspended in hexane including a small amount of EtOAc, collected by filtration, washed with hexane including a small amount of EtOAc, and dried in vacuo to give tert-butyl 4-({5-cyano-2-[(3,5-dichlorophenyl)amino]phenyl}sulfonyl)-1-piperazinecarboxylate (0.087 g, 62.8%).

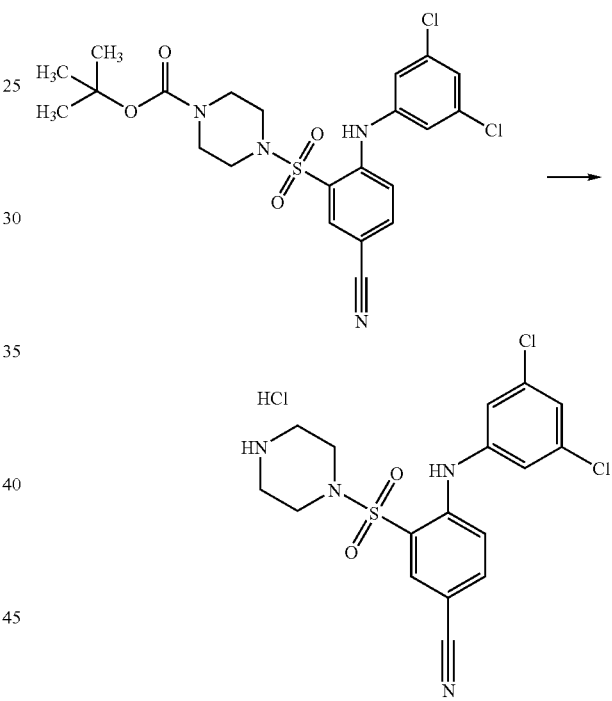

(2) To a solution of tert-butyl 4-({5-cyano-2-[(3,5-dichlorophenyl)amino]-phenyl}sulfonyl)-1-piperazinecarboxylate (0.035 g, 0.068 mmol) in 1,4-dioxane (0.5 ml) was added 4N HCl in 1,4-dioxane (1.5 ml), and the stirring was continued for 3 hrs. The mixture was concentrated in vacuo. The residue was crystallized from $CH_3CN$, washed with $CH_3CN$, and dried in vacuo to give 4-[(3,5-dichlorophenyl)amino]-3-(1-piperazinylsulfonyl)benzonitrile hydrochloride (0.030 g, 97.9%): $^1$H NMR (500 MHz, DMSO-$d_6$) δ 3.13-3.16 (4H, m), 3.34-3.37 (4H, m), 7.37 (1H, d, J=8.8 Hz), 7.39-7.41 (1H, m), 7.41 (2H, s), 7.93 (1H, dd, J=2.2, 8.8 Hz), 8.13 (1H, d, J=2.2 Hz), 8.41 (1H, s), 8.87 (2H, br); FAB-MS: Calcd for $C_{17}H_{16}Cl_2N_4O_2S$ [M+H]$^+$ 411, Found: 411.

Molecular weight: 447.773

Activity grade RBA: A

Activity grade Ca$^{2+}$: A

Example 21-1

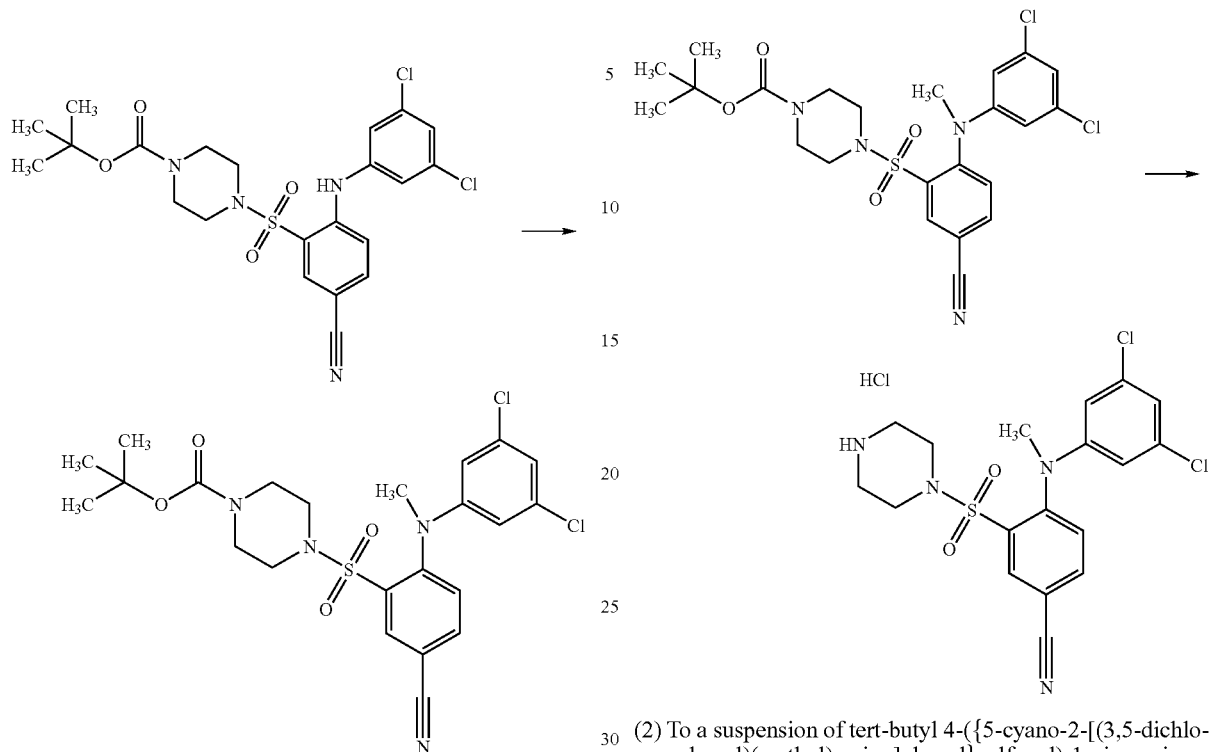

(1) To a cold (0° C.) solution of tert-butyl 4-({5-cyano-2-[(3,5-dichlorophenyl)amino]phenyl}sulfonyl)-1-piperazinecarboxylate (0.049 g, 0.096 mmol) in DMF (1.5 ml) including MeI (0.041 g, 0.287 mmol) was added NaH (0.005 g, 0.115 mmol), and the stirring was continued for 1 h. The mixture was allowed to warm to room temperature, and the stirred was continued for 2 hrs. The mixture was cooled with ice-water bath, quenched with saturated NH$_4$Cl solution, and extracted with EtOAc and water. The separated organic phase was washed with brine, dried over Na$_2$SO$_4$. The solvent was evaporated in vacuo. The residue was purified by column chromatography on silica gel (Hexane/EtOAc=4/1) to give tert-butyl 4-({5-cyano-2-[(3,5-dichlorophenyl)(methyl)amino]phenyl}sulfonyl)-1-piperazinecarboxylate (0.048 g, 95.3%).

(2) To a suspension of tert-butyl 4-({5-cyano-2-[(3,5-dichlorophenyl)(methyl)amino]phenyl}sulfonyl)-1-piperazinecarboxylate (0.043 g, 0.082 mmol) in 1,4-dioxane (1.0 ml) was added 4N HCl in 1,4-dioxane (3.0 ml). The mixture was stirred at room temperature for 2 hrs, and then concentrated in vacuo. The residue was washed twice with Et$_2$O, and dried in vacuo to give 4-[(3,5-dichlorophenyl)(methyl)amino]-3-(1-piperazinylsulfonyl)benzonitrile hydrochloride (0.037 g, 97.9%): mp 163° C. $^1$H NMR (500 MHz, DMSO-d$_6$) δ 2.98 (4H, br), 3.18 (3H, s), 3.29 (4H, br), 6.53 (2H, d, J=1.6 Hz), 6.97 (1H, t, J=1.6 Hz), 7.71 (1H, d, J=8.2 Hz), 8.31 (1H, dd, J=2.2, 8.2 Hz), 8.39 (1H, d, J=1.9 Hz), 8.92 (2H, br); FAB-MS: Calcd for C$_{18}$H$_{18}$Cl$_2$N$_4$O$_2$S [M+H]$^+$ 425, Found:
Molecular weight: 461.800
Activity grade Ca$^{2+}$: B In the similar manner as described in Example 21-1 above, compounds in Example 21-2 as shown in Table 21 were synthesized.

TABLE 21

| EX. No. | moistructure | MW | M + 1 | mp | RBA | Ca2+ |
|---|---|---|---|---|---|---|
| 21-2 | | 440.9525 | 405 | 243 | | A |

Example 22-1

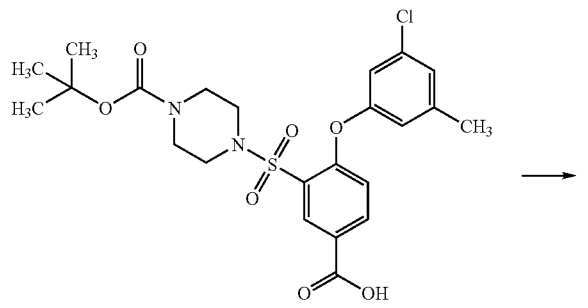

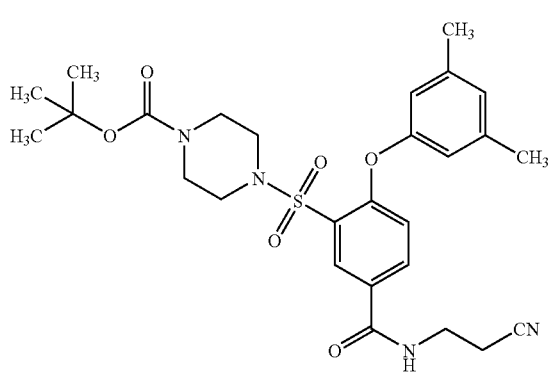

(1) To a cold (0° C.) mixture of 3-{[4-(tert-butoxycarbonyl)-1-piperazinyl]sulfonyl}-4-(3,5-dimethylphenoxy)benzoic acid (0.450 g, 0.917 mmol), 3-aminopropionitrile (0.072 g, 1.009 mmol), HOBt (0.186 g, 1.376 mmol) and DMF (5.0 ml) was added 1-ethyl-3-(3-dimethylaminopropyl)-carbodiimide hydrochloride (0.211 g, 1.101 mmol). After 15 min, the mixture was allowed to warm to room temperature, and the stirring was continued overnight. The mixture was partitioned between EtOAc and water. The separated organic phase was washed with saturated NaHCO$_3$ solution, water and brine, dried over Na$_2$SO$_4$. The solvent was evaporated in vacuo. The residue was purified by column chromatography on silica gel (Hexane/EtOAc=1/2) to give tert-butyl 4-{[5-{[(2-cyanoethyl)amino]carbonyl}-2-(3,5-dimethylphenoxy)phenyl]sulfonyl}-1-piperazinecarboxylate (0.490 g, 98.4%).

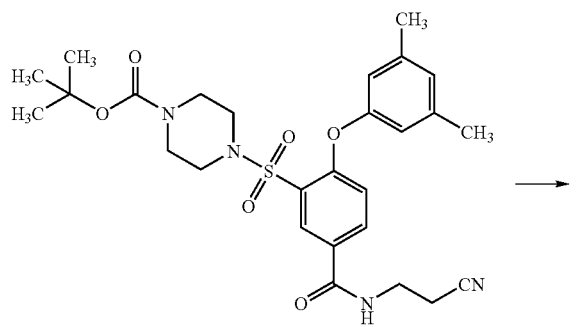

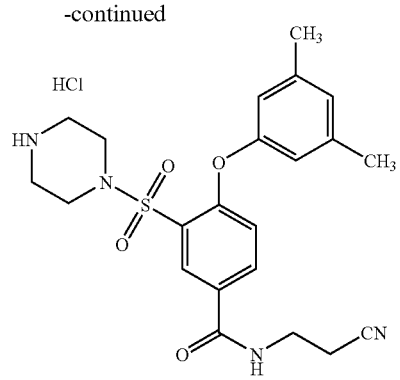

(2) To a solution of tert-butyl 4-{[5-{[(2-cyanoethyl)amino]carbonyl}-2-(3,5-dimethylphenoxy)phenyl]sulfonyl}-1-piperazinecarboxylate (0.030 g, 0.055 mmol) in 1,4-dioxane (1.0 ml) was added 4N HCl in 1,1-dioxane (3.0 ml). The mixture was stirred at room temperature for 1.5 hrs, and then concentrated in vacuo. The residue was crystallized from Et$_2$O, washed with Et$_2$O and dried in vacuo to give N-(2-cyanoethyl)-4-(3,5-dimethylphenoxy)-3-(1-piperazinylsulfonyl)benzamide hydrochloride (0.025 g, 94.4%): mp 101° C. $^1$H NMR (500 MHz, DMSO-d$_6$) δ 2.30 (6H, s), 2.79 (2H, t, J=6.4 Hz), 3.14-3.18 (4H, m), 3.42-3.45 (4H, m), 3.47-3.54 (2H, m), 6.82 (2H, s), 6.95 (1H, s), 7.02 (1H, d, J=8.7 Hz), 8.10 (1H, dd, J=2.3, 8.7 Hz), 8.38 (1H, d, J=2.3 Hz), 9.02 (2H, br), 9.84 (1H, t, J=6.0 Hz); HPLC-MS (ESI): Calcd for C$_{22}$H$_{26}$N$_4$O$_4$S [M+H]$^+$ 443, Found: 443.

Molecular weight: 479.001
Activity grade Ca$^{2+}$: A

Example 22-2

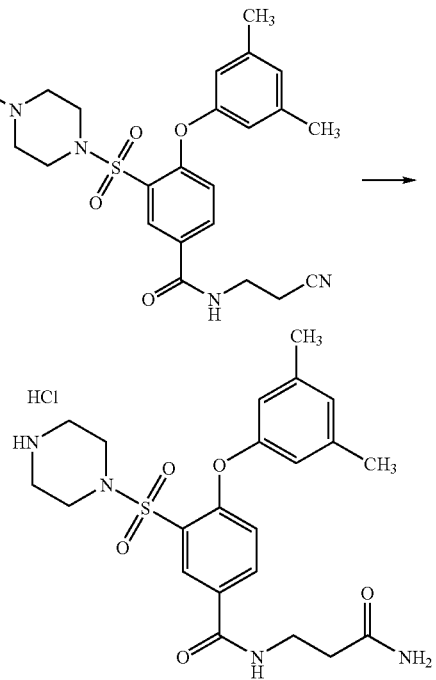

(1) A mixture of tert-butyl 4-([5-{[(2-cyanoethyl)amino]carbonyl}-2-(3,5-dimethylphenoxy)phenyl]sulfonyl}-1-piperazinecarboxylate (0.040 g, 0.074 mmol) and 4 N HCl in 1,4-dioxane (3.0 ml) was stirred for 1.5 hrs. 5N HCl was added, and the stirring was continued for 3 days. The mixture was concentrated in vacuo, and the residue was recrystallized from CH₃CN. The solid obtained was washed twice with CH₃CN and dried in vacuo to give N-[4-(3,5-dimethylphenoxy)-3-(1-piperazinylsulfonyl)benzoyl]-beta-alanineamide hydrochloride (0.036 g, 98.3%): mp 121° C. $^1$H NMR (500 MHz, DMSO-d$_6$) δ 2.30 (6H, s), 2.36 (2H, t, J=7.3 Hz), 3.16 (4H, br), 3.42-3.46 (6H, m), 6.81 (2H, s), 6.83 (1H, s), 6.94 (1H, s), 6.98 (1H, d, J=8.5 Hz), 7.36 (1H, s), 8.08 (1H, dd, J=2.2, 8.8 Hz), 8.35 (1H, d, J=2.2 Hz), 8.76 (1H, t, J=5.7 Hz), 9.13 (2H, br): HPLC-MS (ESI): Calcd for $C_{22}H_{28}N_4O_5S$ [M+H]$^+$ 461, Found: 461.

Molecular weight: 497.017

Activity grade Ca$^{2+}$: A

Example 22-3

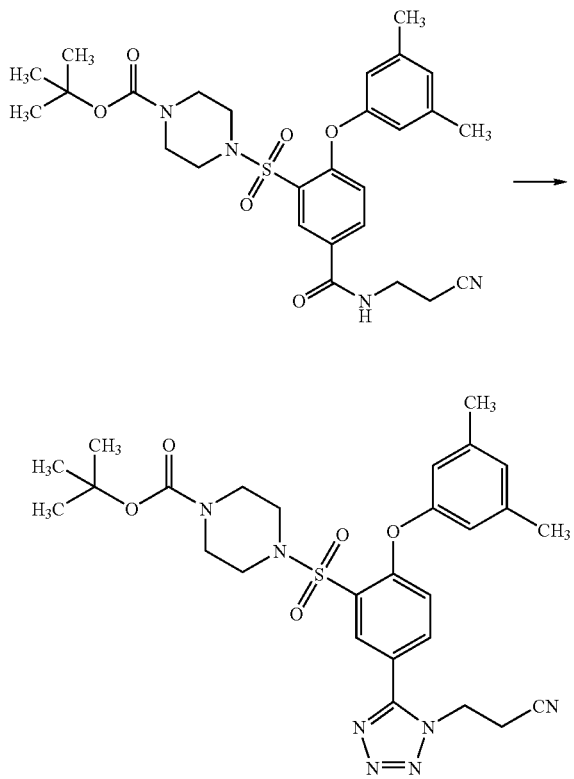

(1) To a solution of tert-butyl 4-{[5-{[(2-cyanoethyl)amino]carbonyl}-2-(3,5-dimethylphenoxy)phenyl]sulfonyl}-1-piperazinecarboxylate (0.396 g, 0.730 mmol) in CH₃CN (3.0 ml) was added triphenylphosphine (0.230 g, 0.876 g). The mixture was gently heated with a heat gun until a clear solution resulted. The mixture was cooled with an ice-water bath, and diethyl azodicarboxylate (0.138 ml, 0.876 mmol) and azidotrimethylsilane (0.116 ml, 0.876 mmol) were added successively. The mixture was allowed to warm to room temperature, and the stirring was continued overnight. A solution of triphenylphosphine (0.115 g, 0.438 mmol), diethyl azodicarboxylate (0.069 ml, 0.438 mmol) and azidotrimethylsilane (0.058 ml, 0.437 mmol) were added successively, and the mixture was stirred for 3 days. The mixture was diluted with EtOAc, and washed with water. The separated organic phase was washed with saturated NaHCO₃ solution, water and brine, dried over Na₂SO₄. The solvent was evaporated in vacuo. The residue was purified by column chromatography on silica gel (Hexane/EtOAc=1/1) to give tert-butyl 4-{[5-[1-(2-cyanoethyl)-1H-tetraazol-5-yl]-2-(3,5-dimethylphenoxy)phenyl]sulfonyl}-1-piperazinecarboxylate (0.338 g, 81.6%).

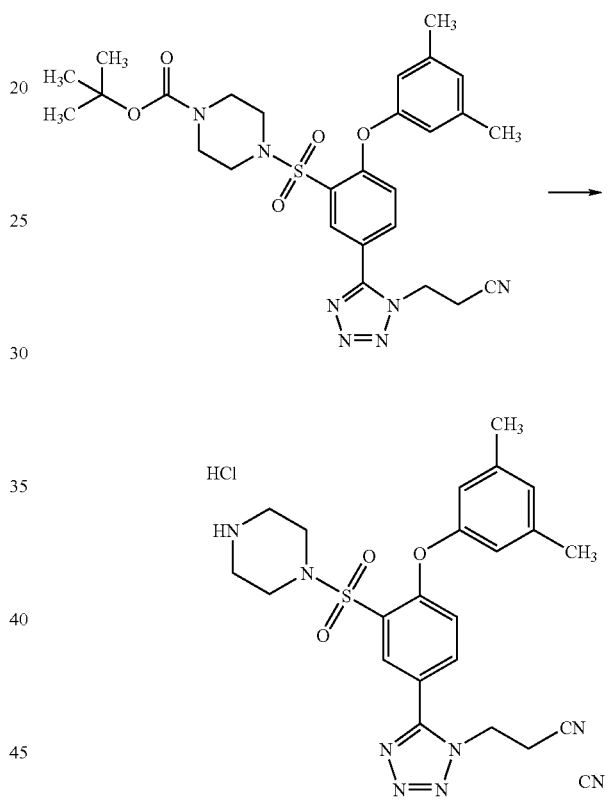

(2) To a solution of tert-butyl 4-([5-[1-(2-cyanoethyl)-1H-tetraazol-5-yl]-2-(3,5-dimethylphenoxy)phenyl]sulfonyl}-1-piperazinecarboxylate (0.030 g, 0.053 mmol) in 1,4-dioxane (1.0 ml) was added 4N HCl in 1,4-dioxane (3.0 ml). The mixture was stirred at room temperature for 2 hrs, then concentrated in vacuo. The residue was recrystallized from Et₂O, washed with Et₂O and dried in vacuo to give 3-{5-[4-(3,5-dimethylphenoxy)-3-(1-piperazinylsulfonyl)phenyl]-1H-tetraazol-1-yl}propanenitrile hydrochloride (0.021 g, 78.8%): mp 125° C. $^1$H NMR (500 MHz, DMSO-d$_6$) δ 2.32 (6H, s), 3.18 (4H, br), 3.23 (2H, t, J=6.3 Hz), 3.50 (4H, br), 4.76 (2H, t, J=6.3 Hz), 6.89 (2H, s), 6.99 (1H, s), 7.10 (1H, d, J=8.5 Hz), 8.04 (1H, dd, J=1.9, 8.5 Hz), 8.26 (1H, d, J=1.9 Hz), 9.05 (2H, br); HPLC-MS (ESI): Calcd for $C_{22}H_{25}N_7O_3S$ [M+H]$^+$ 468, Found: 468.

Molecular weight: 504.014

Activity grade Ca$^{2+}$: A

Example 22-4

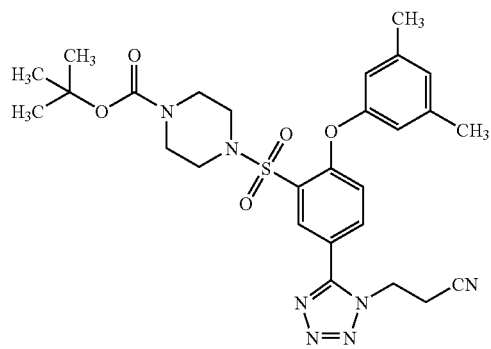

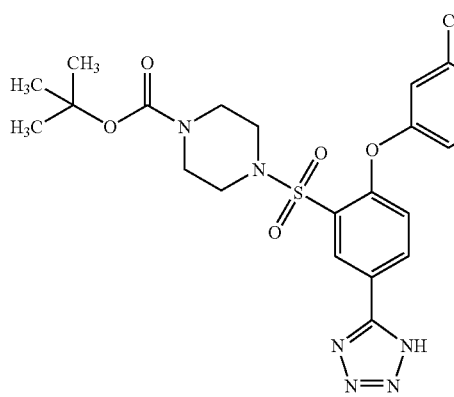

(1) To a solution of tert-butyl 4-{[5-[1-(2-cyanoethyl)-1H-tetraazol-5-yl]-2-(3,5-dimethylphenoxy)phenyl]sulfonyl}-1-piperazinecarboxylate (0.150 g, 0.264 mmol) in CH$_2$Cl$_2$ (2.0 ml) was added DBU (0.119 ml, 0.793 mmol), and the mixture was stirred at room temperature for 2.5 hrs. The mixture was diluted with EtOAc, and washed with 1N HCl. The separated organic phase was washed with water and brine, dried over Na$_2$SO$_4$. The solvent was evaporated in vacuo. The residue was recrystallized from Et$_2$O. The solid was collected by filtration, washed with Et$_2$O and dried in vacuo to give tert-butyl 4-{[2-(3,5-dimethylphenoxy)-5-(1H-tetraazol-5-yl)phenyl]sulfonyl}-1-piperazinecarboxylate (0.096 g, 70.6%).

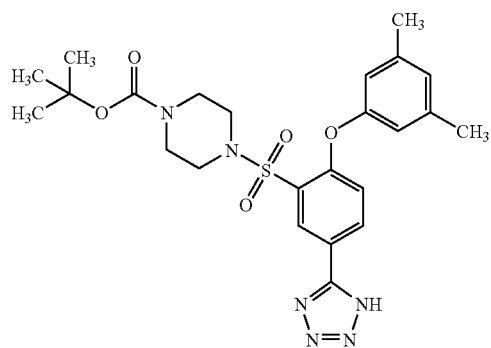

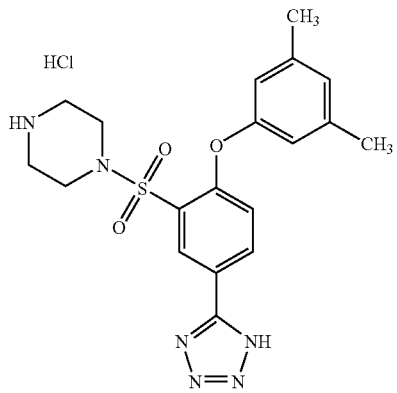

(2) To a solution of tert-butyl 4-{[2-(3,5-dimethylphenoxy)-5-(1H-tetraazol-5-yl)phenyl]sulfonyl}-1-piperazinecarboxylate (0.050 g, 0.097 mmol) in 1,4-dioxane (1.0 ml) was added 4N HCl in 1,4-dioxane (3.0 ml). The mixture was stirred at room temperature for 2 hrs. The precipitate was collected by filtration, washed with 1,4-dioxane and Et$_2$O, dried in vacuo to give 1-{[2-(3,5-dimethylphenoxy)-5-(1H-tetraazol-5-yl)phenyl]sulfonyl)piperazine hydrochloride (0.037 g, 84.4%):mp 213° C. $^1$H NMR (500 MHz, DMSO-d$_6$) δ 2.31 (6H, s), 3.18 (4H, br), 3.48 (4H, br), 6.86 (2H, s), 6.96 (1H, s), 7.14 (1H, d, J=8.8 Hz), 8.29 (1H, dd, J=2.2, 8.8 Hz), 8.56 (1H, d, J=2.2 Hz), 9.07 (2H, br); HPLC-MS (ESI): Calcd for C$_{19}$H$_{22}$N$_6$O$_3$S [M+H]$^+$ 415, Found: 415.

Molecular weight: 450.950

Activity grade Ca$^{2+}$:A

Example 23-1

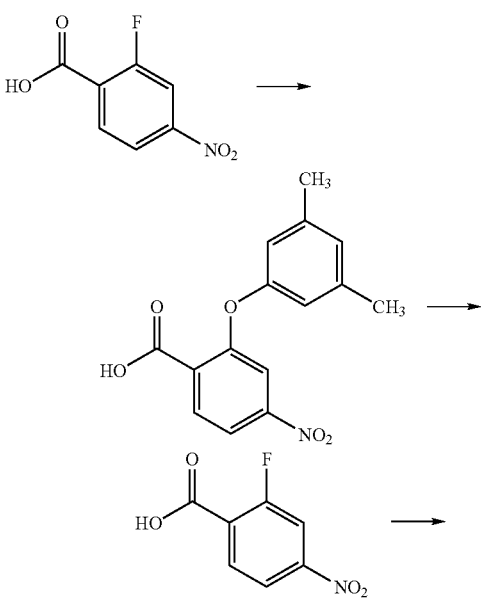

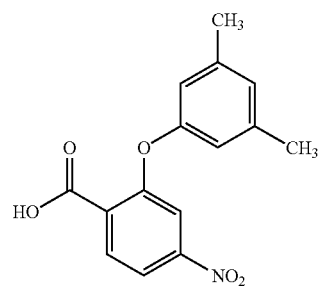

(1) 2-(3,5-dimethylphenoxy)-4-nitrobenzic acid was prepared by the same procedure of 4-(3,5-dichlorophenoxy)-3-nitrobenzoic acid (Example 13-(1)).

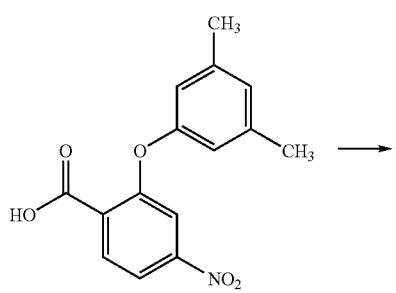

(2) The mixture of 2-(3,5-dimethylphenoxy)-4-nitrobenzic acid (1.72 g, 6.00 mmol), diphenyl phosphoroazidate (1.98 g, 7.20 mmol) and triethylamine (1.00 ml, 7.20 mmol) in tert-butanol was heated to 80° C. overnight. After cooled to room temperature, the reaction mixture was poured into water and the resulting mixture was extracted with EtOAc. The extract was washed with brine, and dried over MgSO$_4$. The solvent was evaporated in vacuo. The residue was purified by chromatography on silica gel (CHCl$_3$/Hexane=65/35) to give a colorless oil. The obtained oil was dissolve into 4N HCl in 1,4-dioxane and the resulting mixture was stirred overnight. Then the reaction mixture was condensed under reduced pressure. The obtained material was dissolved in THF followed addition of ether. The precipitate was collected by filtration, washed with ether and dried in vacuo to give 2-(3,5-dimethylphenoxy)-4-nitroaniline hydrochloride as yellow powder. (0.18 g, 10%)

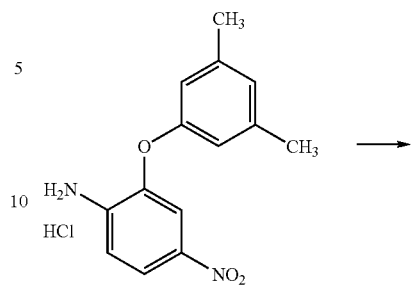

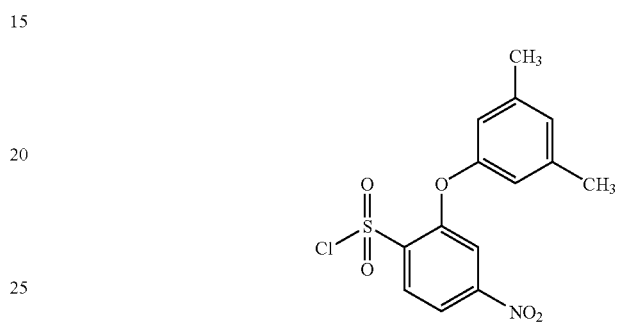

(3) 2-(3,5-dimethylphenoxy)-4-nitrobenzensulfonylchloride was prepared by the same procedure of 5-cyano-2-(3,5-dichlorophenoxy)phenylsulfonylchloride (Example 13-(5)).

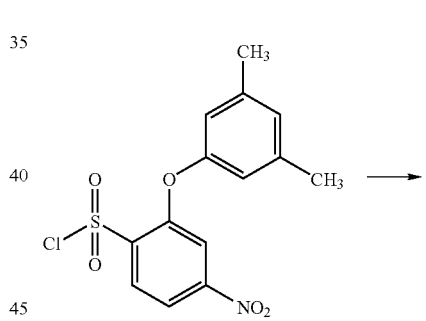

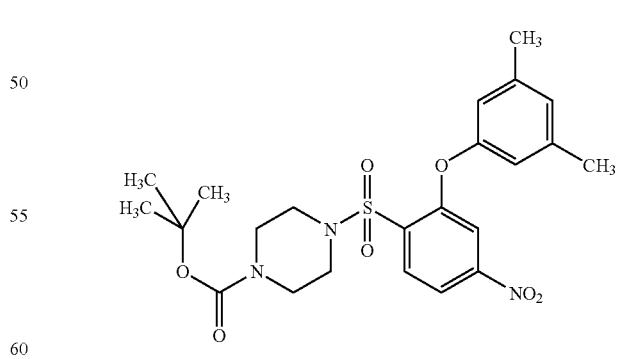

(4) tert-Butyl 4-(2-(3,5-dimethylphenoxy)-4-nitrophenylsulfonyl}-1-piperazinecarboxylate was prepared by the same procedure of 1-{5-cyano-2-(3,5-dichlorophenoxy)phenylsulfony}-(3S)-(tert-butoxycarbonylamino)pyrrolidine (Example 13-1(6)).

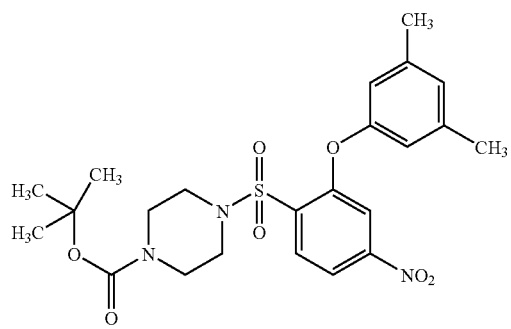

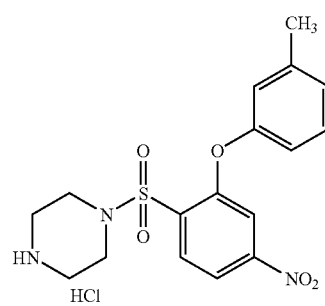

(5) 1-{2-(3,5-dimethylphenoxy)-4-nitrophenylsulfonyl}piperazine hydrochloride was prepared by the same procedure of 1-{5-cyano-2-(3,5-dichlorophenoxy)phenylsulfonyl}-(3S)-aminopyrrolidine hydrochloride (Example 13-(7)):mp 284° C.

$^1$H NMR (500 MHz, DMSO-d$_6$) □; 2.32 (6H, s), 3.18-3.19 (4H, m), 3.51-3.53 (4H, m), 6.92 (2H, s), 7.01 (1H, s), 7.52 (1H, d, J=1.9 Hz), 8.08 (1H, dd, J 8.5, 2.2 Hz), 8.15 (1H, d, J=8.5 Hz), 9.28 (2H, br); HPLC-MS (ESI): calcd for C$_{18}$H$_{22}$ClFN$_2$O$_3$S [M+H]$^+$ 392, Found: 392.

Molecular weight: 427.910

Activity grade Ca$^{2+}$:A

Example 24-1

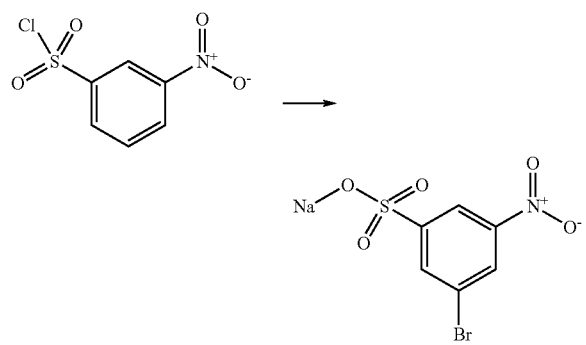

(1) To a vigorously stirred mixture of m-nitrobenzenesulfonyl chloride (3.00 g, 13.5 mmol), trifluoroacetic acid (6.5 ml, 84.4 mmol) and conc. sulfuric acid (2.6 ml, 47.8 mmol) was added N-bromosuccinimide (3.61 g, 20.3 mmol) in portions over an hour period. This mixture was stirred at 45° C. for 88 hrs. The mixture was poured into 25 ml of ice-water, the organic layer was separated, and the aqueous layer was extracted with CH$_2$Cl$_2$ to remove very small amount of 3-bromo-5-nitrobenzenesulfonyl chloride. The aqueous layer was concentrated to give a mixture of 3-bromo-5-nitrobenzenesulfonic acid, 3-nitrobenzenesulfonic acid and sulfuric acid. To the mixture was added 8N NaOH and the resulting precipitate was collected by filtration and washed with water to give sodium 3-bromo-5-nitrobenzenesulfonate (256 mg, 6.2%).

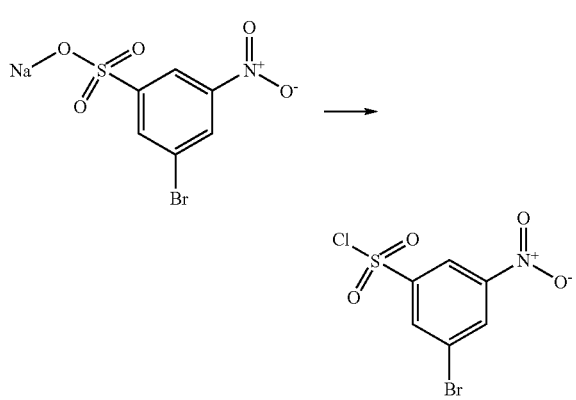

(2) A suspension of sodium 3-bromo-5-nitrobenzenesulfonate (140 mg, 0.46 mmol) in phosphorus oxychloride (1.0 ml, 10.7 mmol) was refluxed for 1 hr. Phosphorus pentachloride (192 mg, 0.92 mmol) was added and the mixture was stirred at 150° C. for additional 1 hr. After cooling to room temperature, the mixture was evaporated. The resulting residue was neutralized with 4N NaOH and the product was extracted with EtOAc. The organic layer was dried over anhydrous MgSO$_4$. The solvent was evaporated in vacuo to give 3-bromo-5-nitrobenzenesulfonyl chloride (103 mg, 74%).

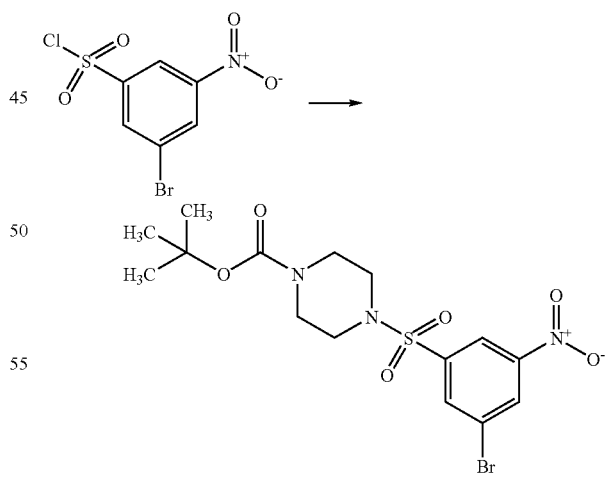

(3) To a mixture of 3-bromo-5-nitrobenzenesulfonyl chloride (100 mg, 0.33 mmol) and N,N-diisopropylethylamine (0.069 ml, 0.40 mmol) in THF (3 ml) was added dropwise the solution of tert-butyl 1-piperazinecarboxylate (68 mg, 0.37 mmol) in THF (2 ml) at 0° C. The mixture was stirred at room temperature for 1 hr. Solvent was removed by evaporation. The resulting residue was diluted with CH₂Cl₂ and washed with 0.5 N HCl, brine, aqueous NaHCO₃, and brine, then dried over anhydrous MgSO₄. The solvent was removed by evaporation and the residue was purified by preparative TLC on silica gel (Hexane/EtOAc=2/1) to give tert-butyl 4-[(3-bromo-5-nitrophenyl)sulfonyl]-1-piperazinecarboxylate (116 mg, 77%); MS (FAB): Calcd for C₁₅H₂₀BrN₃O₆S [M+H]⁺ 450 and 452, Found: 350 and 352 (−Boc).

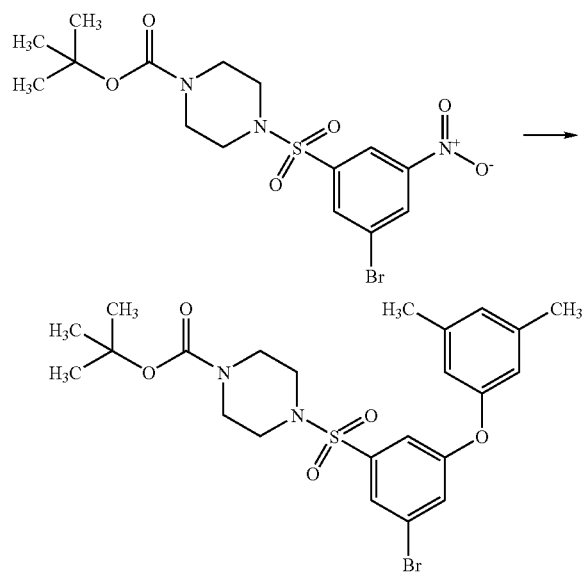

(4) To a suspension of sodium hydride (6.7 mg, 0.17 mmol) in DMF (2 ml) was added 3,5-dimethylphenol (20 mg, 0.17 mmol) at 0° C. This mixture was stirred for 10 min. tert-butyl 4-[(3-bromo-5-nitrophenyl)sulfonyl]-1-piperazinecarboxylate (50 mg, 0.11 mmol) was added to and the mixture was stirred at 90° C. for 2.5 hrs. The reaction mixture was diluted with EtOAc and washed with aqueous NaHCO₃ and brine. The organic layer was dried over anhydrous MgSO₄. The solvent was evaporated in vacuo. The residue was purified by preparative TLC on silica gel (Hexane/EtoAc=2/1). The resulting solid was suspended in ether/hexane/CHCl₃ and collected by filtration to give tert-butyl 4-{[3-bromo-5-(3,5-dimethylphenoxy)phenyl]sulfonyl}-1-piperazinecarboxylate (19.5 mg, 33%): mp 155° C.; HPLC-MS (ESI): Calcd for C₂₃H₂₉BrN₂O₅S [M+H]⁺ 525 and 527, Found: 425 and 427 (−Boc).

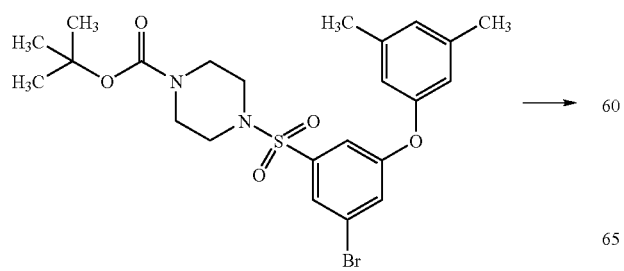

-continued

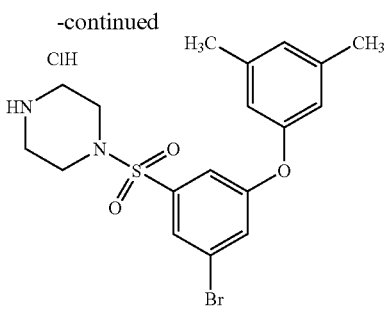

(5) A solution of tert-butyl 4-{[3-bromo-5-(3,5-dimethylphenoxy)phenyl]-sulfonyl}-1-piperazinecarboxylate (17 mg, 0.032 mmol) in 4N HCl solution in 1,4-dioxane (2 ml, 8 mmol) was stirred at room temperature overnight. Solvent was removed by evaporation to give 1-{[3-bromo-5-(3,5-dimethylphenoxy)phenyl]sulfonyl}piperazine hydrochloride (14.9 mg, 99%): mp >84° C. (decomposed); ¹H NMR (500 MHz, DMSO-d₆) δ 2.30 (6H, s), 3.20 (8H, br), 6.79 (2H, s), 6.93 (1H, S), 7.25 (1H, s), 7.60 (1H, d, J=2.0 Hz), 7.66 (1H, s), 8.99 (1H, br); HPLC-MS (ESI): Calcd for C₁₈H₂₁BrN₂O₃S [M+H]+425 and 427, Found: 425 and 427.

Molecular weight: 461.808

Activity grade Ca²⁺:A

Example 25-1

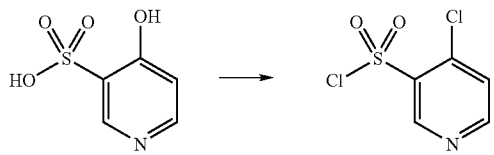

(1) To a mixture of 4-hydroxypyridine-3-sulfonic acid (1.00 g, 5.71 mmol) and phosphorus pentachloride (2.38 g, 11.4 mmol) was added phosphorus oxychloride (1.06 ml, 11.4 mmol) dropwise at 0° C. The mixture was refluxed for 5 hrs. After the mixture was cooled to room temperature, cooled aqueous NaHCO₃ was added to the mixture carefully. The mixture was extracted with CHCl₃. The organic layer was dried over anhydrous MgSO₄. The solvent was evaporated in vacuo to give 4-chloro-3-pyridinesulfonyl chloride as colorless oil (0.97 g, 80.1%).

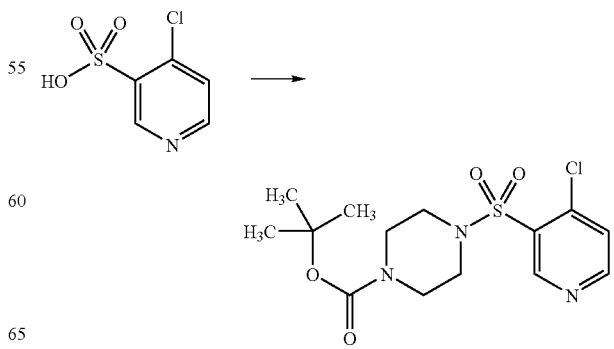

(2) A mixture of 4-chloro-3-pyridinesulfonyl chloride (0.97 g, 4.57 mmol), tert-butyl 1-piperazinecarboxylate (0.94 g, 5.03 mmol), and N,N-diisopropylethylamine (0.88 ml, 5.03 mmol) in THF (50 ml) was stirred at room temperature overnight. The mixture was concentrated in vacuo. The residue was washed with ice water, then was dried in vacuo to give tert-butyl 4-[(4-chloro-3-pyridinyl)sulfonyl]-1-piperazinecarboxylate as a pale yellow solid (1.51 g, 91.3%).

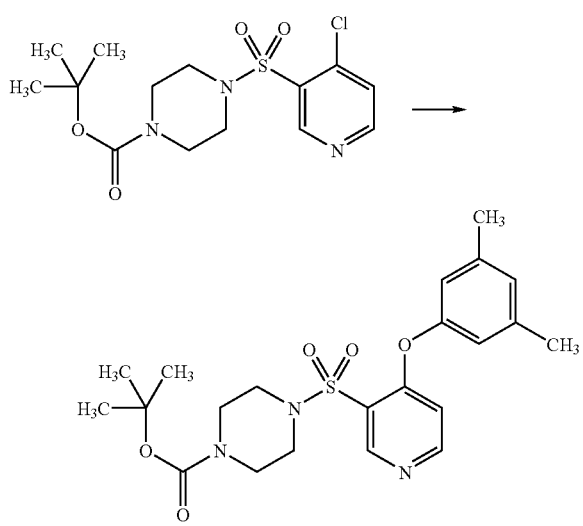

(3) To a solution of 3,5-dimethylphenol (37.1 mg, 0.30 mmol) in 1,4-dioxane (1 ml) was added sodium hydride (60% oil suspension, 13.3 mg, 0.33 mmol) portionwise. The mixture was stirred at room temperature for 30 min. To the mixture was added a solution of tert-butyl 4-[(4-chloro-3-pyridinyl)sulfonyl]-1-piperazinecarboxylate (100 mg, 0.28 mmol) in 1,4-dioxane (1 ml) slowly. The mixture was stirred at 70° C. overnight. After the mixture was cooled to room temperature, the mixture was concentrated in vacuo. The residue was washed with ice water, dried in vacuo to give tert-butyl 4-{[4-(3,5-dimethylphenoxy)-3-pyridinyl]sulfonyl}-1-piperazinecarboxylate (110 mg, 88.9%) as a white solid.

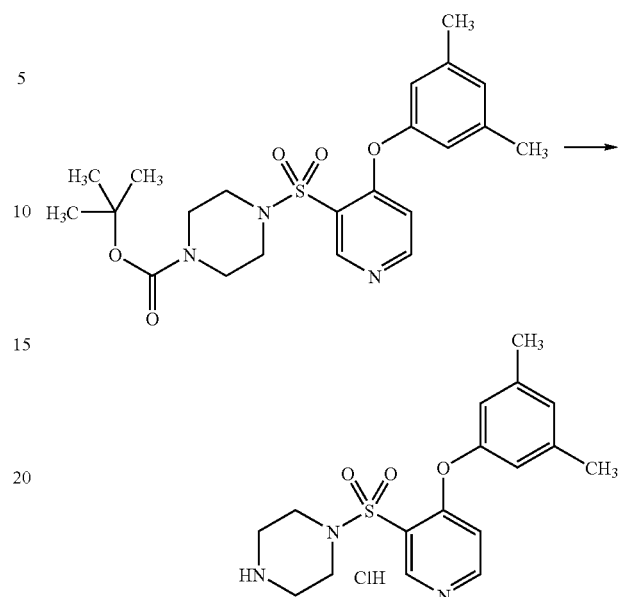

(4) To a solution of tert-butyl 4-{[4-(3,5-dimethylphenoxy)-3-pyridinyl]sulfonyl}-1-piperazinecarboxylate (23.4 mg, 0.0523 mmol) in $CH_2Cl_2$ (1 ml) was added 4N HCl in 1,4-dioxane (0.25 ml). The mixture was stirred at room temperature overnight. The mixture was concentrated in vacuo. The residue was triturated with diethylether, dried in vacuo to give 1-{[4-(3,5-dimethylphenoxy)-3-pyridinyl]sulfonyl}piperazine hydrochloride (17 mg, 76%) as a white solid: mp 220° C.; 1H NMR (300 MHz, DMSO-$d_6$) δ 2.33 (6H, s), 3.19 (4H, m), 3.52 (4H, m), 6.84 (1H, d, J=6 Hz), 7.00 (2H, s), 7.03 (1H, s), 8.65 (1H, d, J=6 Hz), 8.88 (1H, s), 9.35 (2H, br); HPLC-MS (ESI): Calcd for $C_{17}H_{21}N_3O_3S$ $[M+H]^+$ 348, Found: 348.
Molecular weight: 420.361
Activity grade RBA: B
Activity grade $Ca^{2+}$: A In the similar manner as described in Example 25-1 above, compounds in Example 25-2 as shown in Table 25 were synthesized.

TABLE 25

| EX. No. | moistructure | MW | M + 1 | mp | RBA | Ca2+ |
|---|---|---|---|---|---|---|
| 25-2 | | 461.19704 | 388 | 213-215 | A | A |

Example 26-1

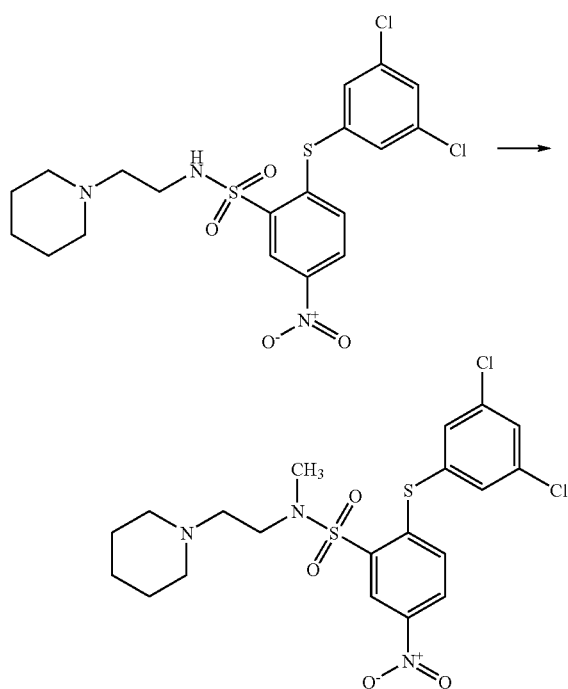

(1) To a suspension of sodium hydride (4.5 mg, 0.11 mmol) in THF (2 ml) was added 2-[(3,5-dichlorophenyl)sulfanyl]-5-nitro-N-[2-(1-piperidinyl)ethyl]benzenesulfonamide (50 mg, 0.10 mmol) at 0° C. The mixture was stirred at 0° C. for 10 min. Methyl iodide (0.01 ml, 0.15 mmol) was added and the mixture was stirred at 0° C. for 30 min then room temperature overnight. The reaction mixture was diluted with EtOAc and washed with aqueous NaHCO$_3$ and brine. The organic layer was dried over anhydrous MgSO$_4$. The solvent was evaporated in vacuo. The residue was purified by preparative TLC on silica gel (CHCl$_3$/MeOH=9/1) to give 2-[(3,5-dichlorophenyl)sulfanyl]-N-methyl-5-nitro-N-[2-(1-piperidinyl)ethyl]benzenesulfonamide (18 mg, 35.0%): mp 113-114° C.; $^1$H NMR (300 MHz, CDCl3) δ 1.42 (2H, m), 1.52 (4H, m), 2.41 (4H, m), 2.57 (2H, t, J=7.0 Hz), 3.03 (3H, s), 3.47 (2H, t, J=7.0 Hz), 7.07 (1H, d, J=8.7 Hz), 7.45 (2H, m), 7.51 (1H, t, J=1.9 Hz), 8.14 (1H, dd, J=2.3, 8.7 Hz), 8.79 (1H, d, J=2.3 Hz); HPLC-MS (ESI): Calcd for C$_{20}$H$_{23}$Cl$_2$N$_3$O$_4$S$_2$ [M+H]$^+$ 504 and 506, Found: 504 and 506.

Molecular weight: 504.458

Activity grade RBA: A

Activity grade Ca$^{2+}$: A

In the similar manner as described in Example 26-1 above, compounds in Example 26-2 and 26-3 as shown in Table 26 were synthesized.

TABLE 26

| EX. No. | moistructure | MW | M + 1 | mp | RBA | Ca2+ |
|---|---|---|---|---|---|---|
| 26-2 | | 490.40935 | 490 | 108-110 | | A |
| 26-3 | | 506.47395 | 506 | 144-145 | | A |

Operative Examples Relating to Pharmaceutical Compositions

The compounds according to the invention can be converted into pharmaceutical preparations as follows:

Tablet

Composition 100 mg of the compound of Example 1-1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension

Composition 1000 mg of the compound of Example 1-1, 1000 mg of ethanol (96%), 400 mg of Rhodigel (xanthan gum from FMC, Pa., USA) and 99 g of water.

A single dose of 100 mg of the compound according to the invention is provided by 10 ml of oral suspension.

Preparation

The Rhodigel is suspended in ethanol and the active component is added to the suspension. The water is added with stirring. Stirring is continued for about 6 h until the swelling of the Rhodigel is complete.

The invention claimed is:

1. A sulfonamide derivative of the formula (I), its tautomeric or stereoisomeric form, or a physiologically acceptable salt thereof:

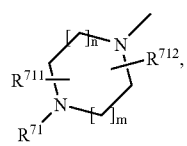

(I)

X represents phenyl, which is substituted by 0 to 5 substituents independently selected from the group consisting of $R^1$, $R^2$, $R^3$, $R^4$ and $R^0$, or pyridine, which is substituted by 0 to 5 substituents independently selected from the group consisting of $R^1$, $R^2$, $R^3$ and $R^4$ wherein $R^1$ is hydrogen, halogen, hydroxy, straight- or branched-$C_{1-6}$ alkyl optionally mono-, di-, or tri-substituted by halogen, or by straight- or branched-$C_{1-6}$ alkoxy, straight- or branched-$C_{1-6}$ alkoxy carbonyl, amino, straight- or branched-$C_{1-6}$ alkylamino, di(straight- or branched-$C_{1-6}$ alkyl)amino, straight- or branched-$C_{1-6}$ alkanoyl, nitro, or phenyl, $R^2$ is hydrogen, halogen, straight- or branched-$C_{1-6}$ alkyl optionally mono-, di-, or tri- substituted by halogen, or by straight- or branched-$C_{1-6}$ alkoxy, or cyano, or $R^1$ and $R^2$ together form benzene ring or $C_{5-8}$ cycloalkyl fused to the adjacent phenyl, $R^3$ is hydrogen, halogen, or straight- or branched-$C_{1-6}$ alkyl, $R^4$ is hydrogen, halogen, or straight- or branched-$C_{1-6}$ alkyl, $R^0$ is hydrogen, halogen, or straight- or branched-$C_{1-6}$ alkyl, Y represents O, NH, NCH$_3$ S, S(O), or SO$_2$;

$Z^1$ represents CH;

$Z^2$ represents CH;

$R^5$ is chloro, iodo, nitro, or cyano;

$R^6$ is hydrogen;

$R^7$ represents

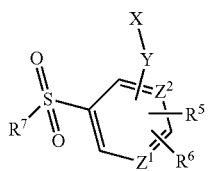

wherein n represents an integer selected from 1 to 3, m represents an integer selected from 0 to 3, $R^{71}$ is hydrogen, $C_{3-8}$ cycloalkyl optionally interrupted by NH, N—CH$_3$ or O, straight- or branched $C_{1-6}$ alkoxycarbonyl, phenyl optionally substituted by straight- or branched $C_{1-6}$ alkyl, benzyl, formyl, or straight- or branched $C_{1-6}$ alkyl wherein the alkyl is optionally substituted by hydroxy, straight- or branched-$C_{1-6}$ alkoxy, hydroxy straight- or branched-$C_{1-6}$ alkoxy, carboxy, straight- or branched-$C_{1-6}$ alkoxycarbonyl, straight- or branched-$C_{1-6}$ alkylthio, di(straight- or branched-$C_{1-6}$ alkyl)amino, from 1 to 3 halogens, or $C_{3-8}$ cycloalkyl optionally interrupted by NH or O, $R^{711}$ and $R^{712}$ are independently selected from the group consisting of hydrogen, halogen, hydroxy, carboxy, cyano, straight- or branched-$C_{1-6}$ alkyl optionally substituted by hydroxy, carboxy, from 1 to 3 halogens, carbamoyl, di(straight-or branched $C_{1-6}$ alkyl)amino carbonyl, and —NR$^{711a}$R$^{711b}$, wherein $R^{711a}$ and $R^{711b}$ are independently selected from the group consisting of hydrogen, straight- or branched-$C_{1-6}$ alkyl, straight- or branched-$C_{1-6}$ alkanoyl, and straight- or branched-$C_{1-6}$ alkylsulfonyl, or $R^{71}$ and $R^{711}$ may form, together with the N atom adjacent to $R^{71}$, a 5 to 8 membered saturated ring.

2. The sulfonamide derivative of the formula (I), its tautomeric or stereoisomeric form, or a physiologically acceptable salt thereof as claimed in claim 1, wherein $R^1$ is halogen, or straight- or branched-$C_{1-6}$ alkyl optionally mono-, di-, or tri-substituted by halogen;

$R^2$ is halogen, or straight- or branched-$C_{1-6}$ alkyl optionally mono-, di-, or tri-substituted by halogen;

$R^3$ is hydrogen;

$R^4$ is hydrogen;

$R^0$ is hydrogen;

Y is O, NH, NCH$_3$, S, S(O), or SO$_2$;

$R^5$ is halogen, nitro, or cyano;

$R^6$ hydrogen; and

R⁷ represents

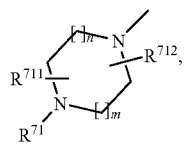

wherein n represents an integer selected from 1 to 3, m represents an integer selected from 0 to 3, R⁷¹ is hydrogen, straight- or branched-$C_{1-6}$ alkyl optionally substituted by hydroxy or hydroxy straight- or branched-$C_{1-6}$ alkoxy, $C_{3-8}$ cycloalkyl, straight- or branched-$C_{1-6}$ alkoxycarbonyl, phenyl optionally substituted by straight- or branched-$C_{1-6}$ alkyl, benzyl, or formyl, R⁷¹¹ and R⁷¹² are independently selected from the group consisting of hydrogen, halogen, carboxy, and straight- or branched $C_{1-6}$ alkyl, or R⁷¹ and R⁷¹¹ may form, together with the N atom adjacent to R⁷¹, a 5 to 8 membered saturated ring.

3. The sulfonamide derivative of the formula (I), its tautomeric or stereoisomeric form, or a physiologically acceptable salt thereof as claimed in claim 1, wherein R¹ and R² are identical or different and represent chloro, or methyl;

R³ is hydrogen or fluoro;

R⁴ is hydrogen;

R⁰ is hydrogen;

Y is O, NH, $NCH_3$, S, S(O), or $SO_2$;

R⁵ is chloro, iodo, nitro, or cyano;

R⁶ is hydrogen; and

R⁷ represents

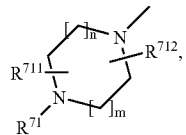

wherein n represents an integer selected from 1 to 3, m represents an integer selected from 0 to 3, R⁷¹ is hydrogen, straight- or branched-$C_{1-6}$ alkyl optionally substituted by hydroxy or hydroxy straight- or branched-$C_{1-6}$ alkoxy, $C_{3-8}$ cycloalkyl, straight- or branched-$C_{1-6}$ alkoxycarbonyl, phenyl optionally substituted by straight- or branched-$C_{1-6}$ alkyl, benzyl, or formyl, R⁷¹¹ and R⁷¹² are independently selected from the group consisting of hydrogen, halogen, carboxy, and straight-or branched-$C_{1-6}$ alkyl, or R⁷¹ and R⁷¹¹ may form, together with the N atom adjacent to R⁷¹, a 5 to 8 membered saturated ring.

4. The sulfonamide derivative of the formula (I), its tautomeric or stereoisomeric form, or a physiologically acceptable salt thereof as claimed in claim 1, wherein R¹ is hydrogen, fluoro, chloro, bromo, methyl, isopropyl, butyl, tert-butyl, trifluoromethyl, methoxy, amino, dimethylamino, acetyl, or nitro;

R² is hydrogen, fluoro, chloro, methyl, isopropyl, tert-butyl, trifluoromethyl, methoxy, or cyano;

R³ is hydrogen or fluoro;

R⁴ is hydrogen;

R⁰ is hydrogen;

Y is O, NH, $NCH_3$, S, S(O), or $SO_2$;

R⁵ is chloro, iodo, nitro, or cyano;

R⁶ is hydrogen; and

R⁷ represents

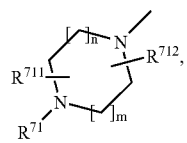

wherein n represents an integer 1, m represents an integer selected from 1 or 2, R⁷¹ represents hydrogen, methyl, ethyl or isopropyl;

R⁷¹¹ represents hydrogen, methyl, or carboxy;

R⁷¹² represents hydrogen or methyl, or

R⁷¹ and R⁷¹¹ may form, together with the N atom adjacent to R⁷¹, a 5 membered saturated ring.

5. The sulfonamide derivative of the formula (I-2), its tautomeric or stereoisomeric form, or a physiologically acceptable salt thereof;

(I-2)

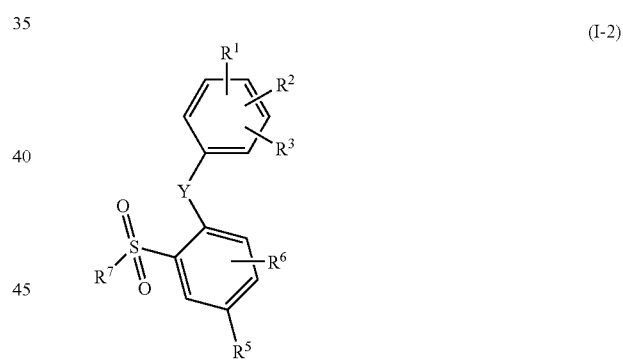

wherein

R¹ is hydrogen, halogen, straight- or branched-$C_{1-6}$ alkyl optionally mono-, di-, or tri-substituted by halogen, straight- or branched-$C_{1-6}$ alkoxy, straight- or branched-$C_{1-6}$ alkoxy carbonyl, amino, straight- or branched -$C_{1-6}$ alkylamino, di(straight- or branched-$C_{1-6}$ alkyl)amino, straight- or branched-$C_{1-6}$ alkanoyl, or nitro, R² is hydrogen, halogen, straight- or branched-$C_{1-6}$ alkyl optionally mono-, di-, or tri-substituted by halogen, straight- or branched-$C_{1-6}$ alkoxy, or cyano, or R¹ and R² may form benzene ring or $C_{5-8}$ cycloalkyl fused to the adjacent phenyl;

R³ is hydrogen or halogen,

Y represents O, NH, $NCH_3$, S, S(O), or $SO_2$;

R⁵ is chloro, iodo, nitro, or cyano;

R⁶ is hydrogen;

R$^7$ represents

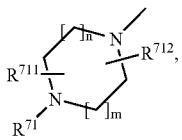

wherein
n represents an integer selected from 1 to 3,
m represents an integer selected from 0 to 3,
R$^{71}$ is hydrogen, straight- or branched-C$_{1-6}$ alkyl optionally substituted by hydroxy or hydroxy straight- or branched-C$_{1-6}$ alkoxy, C$_{3-8}$ cycloalkyl, straight- or branched-C$_{1-6}$ alkoxycarbonyl, phenyl optionally substituted by straight- or branched-C$_{1-6}$ alkyl, benzyl, or formyl,
R$^{711}$ and R$^{712}$ are independently selected from the group consisting of hydrogen, halogen, hydroxy, carboxy, cyano, straight- or branched C$_{1-6}$ alkyl optionally substituted by hydroxy, carboxy, or 1 to 3 halogens, carbamoyl, di (straight- or branched C$_{1-6}$ alkyl) amino carbonyl, or —NR$^{711a}$R$^{711b}$
wherein
R$^{711a}$ and R$^{711b}$ are independently selected from the group consisting of hydrogen, straight- or branched-C$_{1-6}$ alkyl, straight- or branched-C$_{1-6}$ alkanoyl, or straight- or branched-C$_{1-6}$ alkylsulfonyl, or
R$^{71}$ and R$^{711}$ may form, together with the N atom adjacent to R$^{71}$, a 5 to 8 membered saturated ring.

6. The sulfonamide derivative of the formula (I-2), its tautomeric or stereoisomeric form, or a physiologically acceptable salt thereof as claimed in claim 5,
wherein
R$^1$ is hydrogen, halogen, or straight- or branched-C$_{1-6}$ alkyl optionally mono-, di-, or tri-substituted by halogen;
R$^2$ is hydrogen, halogen, or straight- or branched-C$_{1-6}$ alkyl optionally mono-, di-, or tri-substituted by halogen;
R$^3$ is hydrogen or halogen,
Y is O, NH, NCH$_3$, S, S(O), or SO$_2$;
R$^5$ is halogen, nitro, or cyano;
R$^6$ is hydrogen; and
R$^7$ represents

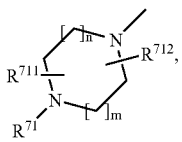

wherein
n represents an integer selected from 1 to 3,
m represents an integer selected from 0 to 3,
R$^{71}$ is hydrogen, straight- or branched-C$_{1-6}$ alkyl optionally substituted by hydroxy or hydroxy straight- or branched-C$_{1-6}$ alkoxy, C$_{3-8}$ cycloalkyl, straight- or branched-C$_{1-6}$ alkoxycarbonyl, phenyl optionally substituted by straight- or branched-C$_{1-6}$ alkyl, benzyl, or formyl,
R$^{711}$ represents hydrogen, methyl, or carboxy,
R$^{712}$ represents hydrogen or methyl, or
R$^{71}$ and R$^{711}$ may form, together with the N atom adjacent to R$^{71}$, a 5 to 8 membered saturated ring.

7. The sulfonamide derivative of the formula (I-2), its tautomeric or stereoisomeric form, or a physiologically acceptable salt thereof as claimed in claim 5,
wherein
R$^1$, R$^2$ and R$^3$ are independently selected from the group consisting of hydrogen, chloro, and methyl;
Y is O, NH, NCH$_3$, S, S(O), or SO$_2$;
R$^5$ is chloro, iodo, nitro, or cyano;
R$^6$ is hydrogen; and
R$^7$ represents

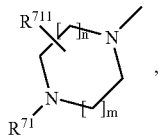

wherein
n represents an integer selected from 1 to 3,
m represents an integer selected from 1 to 3,
R$^{71}$ is hydrogen, straight- or branched-C$_{1-6}$ alkyl optionally substituted by hydroxy or hydroxy straight- or branched-C$_{1-6}$ alkoxy, C$_{3-8}$ cycloalkyl, straight- or branched-C$_{1-6}$ alkoxycarbonyl, phenyl optionally substituted by straight- or branched-C$_{1-6}$ alkyl, benzyl, or formyl,
R$^{711}$ represents hydrogen, methyl, or carboxy or
R$^{71}$ and R$^{711}$ may form, together with the N atom adjacent to R$^{71}$, a 5 to 8 membered saturated ring.
R$^1$ is hydrogen, fluoro, chloro, bromo, methyl, isopropyl, butyl, tert-butyl, trifluoromethyl, methoxy, amino, dimethylamino, acetyl, or nitro;
R$^2$ is hydrogen, fluoro, chloro, methyl, isopropyl, tert-butyl, trifluoromethyl, methoxy, or cyano;
R$^3$ is hydrogen or fluoro;
Y is O, NH, NCH$_3$, S, S(O), or SO$_2$;
R$^5$ is hydrogen, fluoro, chloro, bromo, iodo, trifluoromethyl, hydroxy, methoxy, amino, acetylamino, isobutylcarbonylamino, tert-butylcarbonylamino, benzoylamino, benzylcarbonylamino, phenethylcarbonylamino, methylbenzoylamino, naphthylcarbonylamino, thenoylamino, nitro, cyano, methylsulfonyl, dimethyaminosulfonyl, piperazinosulfonyl, dimethyaminocarbonyl, or piperazinocarbonyl;
R$^6$ is hydrogen, methyl, or methoxy; or
R$^5$ and R$^6$ may form a pyrrole ring fused to adjacent phenyl, and
R$^7$ represents

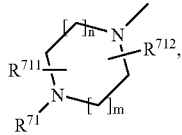

8. The sulfonamide derivative of formula (I-2), its tautomeric or stereoisomeric form, or a physiologically acceptable salt thereof as claimed in claim 5,
wherein
R$^1$ is chloro, bromo, or methyl;
R$^2$ is hydrogen, chloro, bromo, or methyl;
R$^3$ is hydrogen or fluoro;
Y represents O, S, or S(O);
R$^5$ represents hydrogen, chloro, nitro, or cyano;

R⁶ represents hydrogen;
R⁷ represents

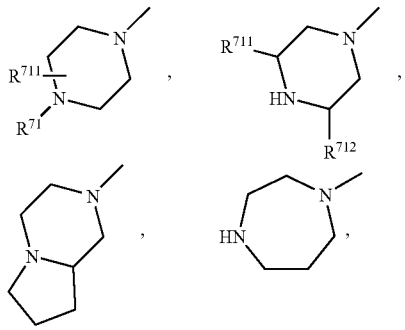

wherein

R⁷¹ represents hydrogen, methyl, ethyl or isopropyl;

R⁷¹¹ represents hydrogen, methyl or carboxy; and

R⁷¹² represents hydrogen or methyl.

9. The sulfonamide derivative, its tautomeric or stereoisomeric form, or a physiologically acceptable salt thereof as claimed in claim 1, wherein said sulfonamide derivative is selected from the group consisting of:

1-{[2-(3,5-dimethylphenoxy)-5-nitrophenyl]sulfonyl}-4-ethylpiperazine,
1-{[2-(3,5-dichlorophenoxy)-5-nitrophenyl]sulfonyl}piperazine,
1-{[2-( 3,5-dimethylphenoxy)-5-nitrophenyl]sulfonyl}-4-isopropylpiperazine,
4-(3,5-dimethylphenoxy)-3-(1-piperazinylsulfonyl)benzonitrile,
1-{[5-chloro-2-(3,5-dimethylphenoxy)phenyl]sulfonyl}-4-ethylpiperazine,
1-{[2-(3,5-dichlorophenoxy)-5-nitrophenyl]sulfonyl}-4-(1-pyrrolidinyl)piperidine,
4-(3,5-dichlorophenoxy)-3-(1-piperazinylsulfonyl)benzonitrile,
4-[(3,5-dichlorophenyl)sulfanyl]-3-(1-piperazinylsulfonyl)benzonitrile,
4-[(3,5-dichlorophenyl)sulfinyl]-3-(1-piperazinylsulfonyl)benzonitrile,
1-{[2-(3,5-dibromophenoxy)-5-nitrophenyl]sulfonyl}piperazine,
1-{[2-(3,5-dichloro-2-fluorophenoxy)-5-nitrophenyl]sulfonyl}piperazine,
1-{[5-cyano-2-(3,5-dichlorophenoxy)phenyl]sulfonyl}-2-piperazinecarboxylic acid,
1-{[2-(3,5-dichlorophenoxy)-5-nitrophenyl]sulfonyl}-2-piperazinecarboxylic acid,
1-{[2-(3,5-dimethylphenoxy)-5-nitrophenyl]sulfonyl}-1,4-diazepane,
1-{[2-(3,5-dichlorophenoxy)-5-nitrophenyl]sulfonyl}-1,4-diazepane,
1-{[2-(3,5-dichlorophenoxy)-5-nitrophenyl]sulfonyl}-3,5-dimethylpiperazine,
3-(1,4-diazepan-1-ylsulfonyl)-4-(3,5-dichlorophenoxy)benzonitrile, and
3-(1,4-diazepan-1-ylsulfonyl)-4-[(3,5-dichlorophenyl)sulfanyl]benzonitrile.

10. A compound of formula (I-2), its tautomeric or stereoisomeric form, or a salt thereof as claimed in claim 5, wherein R¹ is hydrogen, fluoro, chloro, bromo, methyl, isopropyl, butyl, tert-butyl, trifluoromethyl, methoxy, amino, dimethylamino, acetyl, or nitro;

R² is hydrogen, fluoro, chloro, methyl, isopropyl, tert-butyl, trifluoromethyl, methoxy, or cyano; or R³ is hydrogen or flouro;

Y is O, NH, NCH₃, S, S(O), or SO₂;

R⁵ is hydrogen, fluoro, chloro, bromo, iodo, trifluoromethyl, hydroxy, methoxy, amino, acetylamino, isobutylcarbonylamino, tert-butylcarbonylamino, benzoylamino, benzylcarbonylamino, phenethylcarbonylamino, methylbenzoylamino, napthylcarbonylamino, thenoylamino, nitro, cyano, methylsulfonyl, dimethylaminosulfonyl, piperazinosulfonyl, dimethylaminocarbonyl, or piperinocarbonyl;

R⁶ is hydrogen, methyl, or methoxy; or

R⁵ and R⁶ may form a pyrrole ring fused to adjacent phenyl; and

R⁷ represents

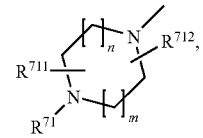

wherein n represents an integer 1;

m represents an integer 1 or 2;

R⁷¹ is hydrogen, methyl, ethyl, isopropyl, sec-butyl, branched pentyl, hydroxyethyl, hydroxyethoxyethyl, cyclopentyl, cyclohexyl, tert-butoxyethyl, phenyl, tolyl, benzyl, or formyl;

R⁷¹¹ is hydrogen methyl, or carboxy;

R⁷¹² is hydrogen or methyl; or

R⁷¹ and R⁷¹¹ may form, together with the N atom adjacent to -R⁷¹, a 5 membered saturated ring.

11. A compound of claim 1, its tautomeric or stereoisomeric form, or a physiologically acceptable salt thereof, wherein the compound is selected from the group consisting of:

1-(2-(3,5-dimethylphenoxy)-5-nitrophenylsulfonyl)piperazine,
1-(2-(3,5-difluorophenoxy)-5-nitrophenylsulfonyl)piperazine,
1-(2-(3,5-dimethoxyphenoxy)-5-nitrophenylsulfonyl)piperazine,
1-(2-(3,5-bis(trifluoromethyl)phenoxy)-5-nitrophenylsulfonyl)piperazine,
1-(2-(3,5-di-tert-butylphenoxy)-5-nitrophenylsulfonyl)piperazine,
1-(2-(3-isopropyl-5-methylphenoxy)-5-nitrophenylsulfonyl)piperazine,
1-(2-(3-isopropyl-5-methylphenoxy)-5-nitrophenylsulfonyl)piperazine,
3-(4-nitro-2-(piperazin-1-ylsulfonyl)phenoxy)benzonitrile,
1-(2-(naphthalen-1-yloxy)-5-nitrophenylsulfonyl)piperazine,
1-(5-nitro-2-(o-tolyloxy)phenylsulfonyl)piperazine,
4-(4-nitro-2-(piperazin-1-ylsulfonyl)phenoxy)aniline, 1-(2-(2-fluorophenoxy)-5-nitrophenylsulfonyl)piperazine,
1-(2-(3-fluorophenoxy)-5-nitrophenylsulfonyl)piperazine,
1-(5-nitro-2-(p-tolyloxy)phenylsulfonyl)piperazine,
1-(5-nitro-2-(m-tolyloxy)phenylsulfonyl)piperazine,
1-(5-nitro-2-phenoxyphenylsulfonyl)piperazine,
1-(2-(4-methoxyphenoxy)-5-nitrophenylsulfonyl)piperazine,
1-(2-(4-fluorophenoxy)-5-nitrophenylsulfonyl)piperazine,
1-(2-(4-tert-butylphenoxy)-5-nitrophenylsulfonyl)piperazine,
1-(2-(4-chlorophenoxy)-5-nitrophenylsulfonyl)piperazine,
4-(4-nitro-2-(piperazin-1-ylsulfonyl)phenoxy)benzonitrile,
1-(5-nitro-2-(m-tolyloxy)phenylsulfonyl)piperazine,
1-(2-(3-fluorophenoxy)-5-nitrophenylsulfonyl)piperazine,
1-(2-(2-methoxyphenoxy)-5-nitrophenylsulfonyl)piperazine,
1-(2-(2-chlorophenoxy)-5-nitrophenylsulfonyl)piperazine,
2-(4-nitro-2-(piperazin-1-ylsulfonyl)phenoxy)benzonitrile,
1-(2-(4-nitro-2-(piperazin-1-ylsulfonyl)phenoxy)phenyl)ethanone,
1-(3-(4-nitro-2-(piperazin-1-ylsulfonyl)phenoxy)phenyl)ethanone,
N,N-dimethyl-3-(4-nitro-2-(piperazin-1-ylsulfonyl)phenoxy)aniline,
1-(2-(3,5-dichlorophenoxy)-5-nitrophenylsulfonyl)piperazine,
1-(5-nitro-2-(3-(trifluoromethyl)phenoxy)phenylsulfonyl)piperazine,
1-(2-(3-tert-butylphenoxy)-5-nitrophenylsulfonyl)piperazine,
1-(2-(3-methoxy-5-methylphenoxy)-5-nitrophenylsulfonyl)piperazine,
1-(5-nitro-2-(3-nitrophenoxy)phenylsulfonyl)piperazine,
1-(2-(3-bromophenoxy)-5-nitrophenylsulfonyl)piperazine,
1-(2-(2-butylphenoxy)-5-nitrophenylsulfonyl)piperazine,
1-(2-(3,5-dichlorophenoxy)-5-fluorophenylsulfonyl)piperazine,
1-(2-(3,5-dimethylphenoxy)-4-methylphenylsulfonyl)piperazine,
methyl 5-(4-nitro-2-(piperazin-1-ylsulfonyl)phenoxy)nicotinate,
1-(2-(3,5-dimethylphenoxy)-5-nitrophenylsulfonyl)-2,5-dimethylpiperazine,
1-(2-(5-chloropyridin-3-yloxy)-5-nitrophenylsulfonyl)piperazine,
1-(5-chloro-2-(3,5-dichlorophenoxy)phenylsulfonyl)piperazine,
1-(5-bromo-2-(3,5-dichlorophenoxy)phenylsulfonyl)piperazine,
1-(2-(3,5-dimethylphenoxy)-6-fluorophenylsulfonyl)piperazine,
1-(2-(4-chloro-3-methylphenoxy)-5-nitrophenylsulfonyl)piperazine,
1-(5-nitro-2-(2,3,6-trimethylphenoxy)phenylsulfonyl)piperazine,
1-(2-(2,3-dimethylphenoxy)-5-nitrophenylsulfonyl)piperazine,
1-(2-(3,4-dimethylphenoxy)-5-nitrophenylsulfonyl)piperazine,
1-(2-(2,5-dimethylphenoxy)-5-nitrophenylsulfonyl)piperazine,
1-(5-nitro-2-(2,3,5-trimethylphenoxy)phenylsulfonyl)piperazine,
1-(2-(2-isopropyl-5-methylphenoxy)-5-nitrophenylsulfonyl)piperazine,
3-(4-nitro-2-(piperazin-1-ylsulfonyl)phenoxy)aniline,
1-(2-(biphenyl-3-yloxy)-5-nitrophenylsulfonyl)piperazine,
1-(5-nitro-2-(3,4,5-trimethylphenoxy)phenylsulfonyl)piperazine,
1-(2-(6-methylpyridin-3-yloxy)-5-nitrophenylsulfonyl)piperazine,
3-methyl-5-(4-nitro-2-(piperazin-1-ylsulfonyl)phenoxy)phenol hydrochloride,
1-(5-nitro-2-(5,6,7,8-tetrahydronaphthalen-2-yloxy)phenylsulfonyl)piperazine,
1-(5-nitro-2-(2,3,4,5,6-pentafluorophenoxy)phenylsulfonyl)piperazine,
1-(5-nitro-2-(2,3,5,6-tetrafluorophenoxy)phenylsulfonyl)piperazine,
1-(2-(5-methyl-2-nitrophenoxy)-5-nitrophenylsulfonyl)piperazine,
1-(2-(4-chloro-3,5-dimethylphenoxy)-5-nitrophenylsulfonyl)piperazine,
1-(2-(2-chloro-5-methylphenoxy)-5-nitrophenylsulfonyl)piperazine,
1-(2-(4-chloro-2-isopropyl-5-methylphenoxy)-5-nitrophenylsulfonyl)piperazine,
1-(2-(2,3-dichlorophenoxy)-5-nitrophenylsulfonyl)piperazine,
1-(2-(2,5-dichlorophenoxy)-5-nitrophenylsulfonyl)piperazine,
1-(2-(3-chloro-4-fluorophenoxy)-5-nitrophenylsulfonyl)piperazine,
1-(5-nitro-2-(2,3,5-trichlorophenoxy)phenylsulfonyl)piperazine,
2-(4-(2-(3,5-dimethylphenoxy)-5-nitrophenylsulfonyl)piperazin-1-yl)ethanol,
2-(2-(4-(2-(3,5-dimethylphenoxy)-5-nitrophenylsulfonyl)piperazin-1-yl)ethoxy)ethanol,
1-(2-(3,5-dimethylphenoxy)-5-nitrophenylsulfonyl)-3,5-dimethylpiperazine,
1-(2-(3,5-dimethylphenoxy)-5-nitrophenylsulfonyl)-2,6-dimethylpiperazine,
1-(2-(3,5-dimethylphenylthio)-5-nitrophenylsulfonyl)piperazine,
1-(2-(3,5-dichlorophenylthio)-5-nitrophenylsulfonyl)-4-((tetrahydrofuran-2-yl)methyl)piperazine,
ethyl 3-(4-(2-(3,5-dichlorophenylthio)-5-nitrophenylsulfonyl)piperazin-1-yl)propanoate,
1-(2-(3,5-dichlorophenylthio)-5-nitrophenylsulfonyl)-4-(3-methoxypropyl)piperazine,
3-(4-(2-(3,5-dichlorophenylthio)-5-nitrophenylsulfonyl)piperazin-1-yl)propanoic acid,
1-(5-nitro-2-(phenylthio)phenylsulfonyl)piperazine,
1-(2-(2,4,6-trimethylphenylthio)-5-nitrophenylsulfonyl)piperazine,
1-(5-nitro-2-(3-methylphenylthio)phenylsulfonyl)piperazine,
1-(2-(3-chlorophenylthio)-5-nitrophenylsulfonyl)piperazine,
1-(2-(3,5-dichlorophenylthio)-5-nitrophenylsulfonyl)piperazine, 1-(2-(3-fluorophenylthio)-5-nitrophenylsulfonyl)piperazine,
1-(2-(3,5-bis(trifluoromethyl)phenylthio)-5-nitrophenylsulfonyl)piperazine,
1-(2-(naphthalen-2-ylthio)-5-nitrophenylsulfonyl)piperazine,
N-(3,5-dimethylphenyl)-4-nitro-2-(piperazin-1-ylsulfonyl)aniline,
N-(3,5-dichlorophenyl)-4-nitro-2-(piperazin-1-ylsulfonyl)aniline,
4-nitro-2-(piperazin-1-ylsulfonyl)-N-2-methylphenylaniline,
4-nitro-2-(piperazin-1-ylsulfonyl)-N-3-methylphenylaniline,
4-nitro-2-(piperazin-1-ylsulfonyl)-N-4-methylphenylaniline,
N-(2-chlorophenyl)-4-nitro-2-(piperazin-1-ylsulfonyl)aniline,
N-(3-chlorophenyl)-4-nitro-2-(piperazin-1-ylsulfonyl)aniline,
N-(4-chlorophenyl)-4-nitro-2-(piperazin-1-ylsulfonyl)aniline,
N-(2-fluorophenyl)-4-nitro-2-(piperazin-1-ylsulfonyl)aniline,
N-(3-fluorophenyl)-4-nitro-2-(piperazin-1-ylsulfonyl)aniline,
N-(4-fluorophenyl)-4-nitro-2-(piperazin-1-ylsulfonyl)aniline,
N-(2-methoxyphenyl)-4-nitro-2-(piperazin-1-ylsulfonyl)aniline,
1-(2-(3,5-dimethylphenoxy)-5-nitrophenylsulfonyl)-4-methylpiperazine,
1-cyclohexyl-4-(2-(3,5-dimethylphenoxy)-5-nitrophenylsulfonyl)piperazine,
1-(2-(3,5-dimethylphenoxy)-5-nitrophenylsulfonyl)-4-phenylpiperazine,
1-(2-(3,5-dimethylphenoxy)-5-nitrophenylsulfonyl)-4-(4-methylphenyl)piperazine,
1-benzyl-4-(2-(3,5-dimethylphenoxy)-5-nitrophenylsulfonyl)piperazine,
4-(2-(3,5-dimethylphenoxy)-5-nitrophenylsulfonyl)piperazine-1-carbaldehyde,
1-(2-(3,5-dimethylphenoxy)-5-nitrophenylsulfonyl)-4-isopropylpiperazine,
1-sec-butyl-4-(2-(3,5-dimethylphenoxy)-5-nitrophenylsulfonyl)piperazine,
1-(2-(3,5-dimethylphenoxy)-5-nitrophenylsulfonyl)-4-(pentan-2-yl)piperazine,
1-(2-(3,5-dimethylphenoxy)-5-nitrophenylsulfonyl)-4-(pentan-3-yl)piperazine,
1-cyclopentyl-4-(2-(3,5-dimethylphenoxy)-5-nitrophenylsulfonyl)piperazine,
1-(2-(3,5-dimethylphenoxy)-5-nitrophenylsulfonyl)-4-((tetrahydrofuran-2-yl)methyl)piperazine,
1-(2-(3,5-dichlorophenoxy)-5-nitrophenylsulfonyl)-4-((tetrahydrofuran-2-yl)methyl)piperazine,
1-(2-(3,5-dimethylphenylthio)-5-nitrophenylsulfonyl)-4-((tetrahydrofuran-2-yl)methyl)piperazine,
2-(4-(2-(3,5-dichlorophenoxy)-5-nitrophenylsulfonyl)piperazin-1-yl)-N,N-diethylethanamine,
2-(4-(2-(3,5-dichlorophenoxy)-5-nitrophenylsulfonyl)piperazin-1-yl)-N,N-dimethylethanamine,
1-(2-(3,5-dichlorophenoxy)-5-nitrophenylsulfonyl)-4-(1-methylpiperidin-4-yl)piperazine,
1-(2-(3,5-dimethylphenoxy)-5-nitrophenylsulfonyl)-4-(3,3,3-trifluoropropyl)piperazine,
1-(2-(3,5-dichlorophenoxy)-5-nitrophenylsulfonyl)-4-(3,3,3-trifluoropropyl)piperazine,
1-(2-(3,5-dichlorophenoxy)-5-nitrophenylsulfonyl)-4-(3-methoxypropyl)piperazine,
ethyl 3-(4-(2-(3,5-dichlorophenoxy)-5-nitrophenylsulfonyl)piperazin-1-yl)propanoate,
1-(5-chloro-2-(3,5-dimethylphenoxy)phenylsulfonyl)piperazine,
1-(2-(3,5-dimethylphenoxy)-5-iodophenylsulfonyl)-4-ethylpiperazine,
1-(2-(3,5-dimethylphenoxy)-5-iodophenylsulfonyl)piperazine,
4-(3,5-dimethylphenoxy)-2-methyl-5-(piperazin-1-ylsulfonyl)aniline,
1-(2-(3,5-dimethylphenoxy)-5-fluorophenylsulfonyl)piperazine,
4-(3,5-dichlorophenoxy)-3-(4-(3-methoxypropyl)piperazin-1-ylsulfonyl)benzonitrile,
4-(3,5-dichlorophenylthio)-3-(piperazin-1-ylsulfonyl)benzonitrile,
4-(3,5-dichlorophenylthio)-3-(4-(3-(methylthio)propyl)piperazin-1-ylsulfonyl)benzonitrile,
3-(1,4-diazepan-1-ylsulfonyl)-4-(3,5-dichlorophenylthio)benzonitrile,
4-(3,5-dichlorophenylsulfonyl)-3-(piperazin-1-ylsulfonyl)benzonitrile,
4-(3,5-dichlorophenylamino)-3-(piperazin-1-ylsulfonyl)benzonitrile,
4-((3,5-dichlorophenyl)(methyl)amino)-3-(piperazin-1-ylsulfonyl)benzonitrile,
N-(3,5-dimethylphenyl)-N-methyl-4-nitro-2-(piperazin-1-ylsulfonyl)aniline, and
1-(2-(3,5-dimethylphenoxy)-4-nitrophenylsulfonyl)piperazine.

12. A compound of claim 11, wherein the salt is a hydrochloride, dihydrochloride, trihydrochloride, or a mono-, di- or tri-trifluoroacetate.

13. A compound of claim 12, wherein the salt is a hydrochloride.

14. A pharmaceutical composition comprising a compound of claim 1 and one or more pharmaceutically acceptable carriers or excipients.

15. The pharmaceutical composition of claim 14, wherein the compound, its tautomeric or stereoisomeric form, or a physiologically acceptable salt thereof is in unit dosage form.

16. A method of treating a CCR3 related disease or disorder comprising administering a compound of claim 1, wherein the disease or disorder is selected from the group consisting of arthritis, asthma, allergic rhinitis, atopic dermatitis, athero sclerosis, Grave's disease, HIV infection, lung granuloma, and Alzheimer's disease.

17. A compound, its tautomeric or stereoisomeric form, or a physiologically acceptable salt thereof, wherein the compound is selected from the group consisting of:
1-(2-(3,5-dimethylphenoxy)-5-(piperazin-1-ylsulfonyl)phenylsulfonyl)piperazine,
1-(2-(3,5-dimethylphenoxy)-5-(methylsulfonyl)phenylsulfonyl)piperazine,
1-(2-(3,5-dimethylphenoxy)phenylsulfonyl)piperazine,
(4(3,5-dimethylphenoxy)-3-(piperazin-1-ylsulfonyl)phenyl)(piperazin-1-yl)methanone,
1-(2-(3,5-dimethylphenoxy)-5-(trifluoromethyl)phenylsulfonyl)piperazine,
1-(2-(3,5-dichlorophenoxy)-4-methyl-5-nitrophenylsulfonyl)piperazine,
1-(2-(3,5-dimethylphenoxy)-4-(trifluoromethyl)phenylsulfonyl)piperazine, 1-(2-(3,5-dimethylphenoxy)-4-methoxy-5-nitrophenylsulfonyl)piperazine,
1-(2-(3,5-dimethylphenoxy)-4-methoxyphenylsulfonyl)piperazine hydrochloride,
1-(2-(3,5-dimethylphenoxy)-4-methoxy-5-nitrophenylsulfonyl)piperazine,
1-(2-(3,5-dimethylphenoxy)-3-(piperazin-1-ylsulfonyl)aniline,
1-(5-chloro-2-(3,5-dimethylphenoxy)-4-methylphenylsulfonyl)piperazine,
4-(3,5-dimethylphenoxy)-3-(piperazin-1-ylsulfonyl)phenol,
1-(2-(3,5-dimethylphenoxy)-5-(methoxyphenylsulfonyl)piperazine,
1-(2-(3,5-dimethylphenoxy)-5-(fluorophenylsulfonyl)piperazine,
N-(4-(3,5-dimethylphenoxy)-3-(piperazin-1-ylsulfonyl)phenyl)acetamide,
N-(4-(3,5-dimethylphenoxy)-3-(piperazin-1-ylsulfonyl)phenyl)pivalamide,
N-(4-(3,5-dimethylphenoxy)-3-(piperazin-1-ylsulfonyl)phenyl)3-methylbutanamide,
N-(4-(3,5-dimethylphenoxy)-3-(piperazin-1-ylsulfonyl)phenyl)benzamide,
N-(4-(3,5-dimethylphenoxy)-3-(piperazin-1-ylsulfonyl)phenyl)-4-methylbenzamide,
N-(4-(3,5-dimethylphenoxy)-3-(piperazin-1-ylsulfonyl)phenyl)a-1-naphthamide,
N-(4-(3,5-dimethylphenoxy)-3-(piperazin-1-ylsulfonyl)phenyl)-3-phenylpropanamide,
N-(4-(3,5-dimethylphenoxy)-3-(piperazin-1-ylsulfonyl)phenyl)thiophene-2-carboxamide,
1-(5-bromo-2-(3,5-dimethylphenoxy)phenylsulfonyl)piperazine,
4-(3,5-dichlorophenoxy)-N,N-dimethyl-3-(piperazin-1-ylsulfonyl)benzamide,
4-(3,5-dimethylphenoxy)-N,N-dimethyl-3-(piperazin-1-ylsulfonyl)benzamide,
5-(3,5-dimethylphenoxy)-6-(piperazin-1-ylsulfonyl)-1H-indole,
2-chloro-4-(3,5-dimethylphenoxy)-5-(piperazin-1-ylsulfonyl)benzonitrile,
2-chloro-4-(3,5-dichlorophenoxy)-5-(piperazin-1-ylsulfonyl)benzonitrile,
4-(3,5-dimethylphenoxy)-3-(piperazin-1-ylsulfonyl)benzoic acid,
3-(4-(tert-butoxycarbonyl)piperazin-1-ylsulfonyl)-4-(3,5-dichlorophenoxy)benzoic acid,
4-(3,5-dichlorophenoxy)-3-(piperazin-1-ylsulfonyl)benzoic acid,
4-(3,5-dichlorophenoxy)-3-(piperazin-1-ylsulfonyl)benzamide,
methyl 4-(3,5-dimethylphenoxy)-3-(piperazine-1-ylsulfonyl)benzoate,
2-chloro-4-(3,5-dimethylphenoxy)-5-(piperazin-1-ylsulfonyl)benzamide,
4-(3,5-dichlorophenoxy)-3-fluoro-5-(piperazin-1-ylsulfonyl)benzamide,
4-(3,5-dimethylphenoxy)-3-(piperazin-1-ylsulfonyl)methanol,
N-(2-cyanoethyl)-4-(3,5-dimethylphenoxy)3-(piperazin-1-ylsulfonyl)benzamide,
N-(3-amino-3-oxopropyl)-4-(3,5-dimethylphenoxy)-3-(piperazin-1-ylsulfonyl)benzamide,
3-(5-3,5-dimethylphenoxy)-3-(piperazin-1-ylsulfonyl)phenyl)-1H-tetrazol-1-yl)propanenitrile,
1-(2-(3,5-dimethylphenoxy)-5-(1H-tetrazol-5-yl)phenylsulfonyl)piperazine, and
1-(4-bromo-2-(3,5-dimethylphenoxy)phenylsulfonyl)piperazine.

18. A pharmaceutical composition comprising a compound of claim 17 and one or more pharmaceutically acceptable carriers or excipients.

19. A method of treating a CCR3 related disease or disorder comprising administering a compound of claim 17, wherein the disease or disorder is selected from the group consisting of arthritis, asthma, allergic rhinitis, atopic dermatitis, athero sclerosis, Grave's disease, HIV infection, lung granuloma, and Alzheimer's disease.

* * * * *